US012649766B2

(12) United States Patent
Strelkova et al.

(10) Patent No.: US 12,649,766 B2
(45) Date of Patent: Jun. 9, 2026

(54) ISOLATED MODIFIED VP1 CAPSID PROTEIN OF AAV5

(71) Applicant: LIMITED LIABILITY COMPANY "ANABION", Saint Petersburg (RU)

(72) Inventors: Anna Nikolaevna Strelkova, g. Yaransk (RU); Aleksandr Vladimirovich Karabelskii, g. Gatchina (RU); Dmitrij Aleksandrovich Madera, Moscow (RU); Mariya Pavlovna Perepelkina, Saint-Petersburg (RU); Elena Victorovna Iurlova, Saint-Petersburg (RU); Pavel Mikhailovich Gershovich, Saint-Petersburg (RU); Alexandr Vladimirovich Prokofyev, Saint-Petersburg (RU); Dmitry Valentinovich Morozov, Saint-Petersburg (RU)

( * ) Notice: Subject to any disclaimer, the term of this patent is extended or adjusted under 35 U.S.C. 154(b) by 1018 days.

(21) Appl. No.: 17/637,099

(22) PCT Filed: Aug. 21, 2020

(86) PCT No.: PCT/RU2020/000445
§ 371 (c)(1),
(2) Date: Feb. 22, 2022

(87) PCT Pub. No.: WO2021/034222
PCT Pub. Date: Feb. 25, 2021

(65) Prior Publication Data
US 2022/0306696 A1     Sep. 29, 2022

(30) Foreign Application Priority Data
Aug. 22, 2019     (RU) ................................ 2019126509

(51) Int. Cl.
| | |
|---|---|
| *C07K 14/005* | (2006.01) |
| *A61K 38/37* | (2006.01) |
| *A61K 38/48* | (2006.01) |
| *A61P 7/04* | (2006.01) |
| *C12N 15/86* | (2006.01) |

(52) U.S. Cl.
CPC ............ *C07K 14/005* (2013.01); *A61K 38/37* (2013.01); *A61K 38/4846* (2013.01); *A61P 7/04* (2018.01); *C12N 15/86* (2013.01); *C12Y 304/21022* (2013.01); *C12N 2750/14122* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 2007/0238684 A1 | 10/2007 | Halek et al. | |
| 2015/0023924 A1 | 1/2015 | High et al. | |
| 2016/0201088 A1 | 7/2016 | Gao et al. | |
| 2016/0289275 A1* | 10/2016 | Chiorini ............. | A61K 48/0008 |
| 2022/0154217 A1* | 5/2022 | Reid .................. | C12N 15/1055 |

FOREIGN PATENT DOCUMENTS

| | | |
|---|---|---|
| WO | 99/67393 A2 | 12/1999 |
| WO | 2012/145601 A2 | 10/2012 |
| WO | 2013/158879 A1 | 10/2013 |
| WO | 2017/058892 A2 | 4/2017 |
| WO | 2017/201121 A1 | 11/2017 |
| WO | 2020/205889 A1 | 10/2020 |

OTHER PUBLICATIONS

Ling, Chen, et al. "Development of optimized AAV serotype vectors for high-efficiency transduction at further reduced doses." Human Gene Therapy Methods 27.4 (2016): 143-149. (Year: 2016).*
Miesbach et al. (Blood, The Journal of the American Society of Hematology 131.9 (2018): 1022-1031., hereinafter "Miesbach") (Year: 2018).*
McClements et al. (The Yale journal of biology and medicine 90.4 (2017): 611., hereinafter "McClements") (Year: 2017).*
Perrin et al. (Blood, The Journal of the American Society of Hematology 133.5 (2019): 407-414., hereinafter "Perrin") (Year: 2019).*
Chen et al. (Human Gene Therapy Methods 27.4 (2016): 143-149.) (Year: 2016).*
Venkatakrishnan et al. (Journal of virology 87.9 (2013): 4974-4984.) (Year: 2013).*
Related Japanese patent application No. 2022-512768 examination report dated Aug. 7, 2024. (Translation provided).
EA Epifanova, et al., Viral Vectors for Delivering Gene Material into Cells and Their Application in Neurobiology (Review). Sovremennye tehnologii v medicine. CTM, 2017. vol. 9, No. 1. pp. 162-173. DOI:10.17691/stm2017.9.1.21.
Dwaipayan Sen et al., Improved adeno-associated virus (AAV) serotype 1 and 5 vectors for gene therapy. Scientific Reports. May 2013, 6 (1):1832. pp. 1-6. DOI:10.1038/srep01832.
Savita Rangarajan, et al., AAV5-Factor VIII Gene Transfer in Severe Hemophilia A. The New England Journal of Medicine. 2017; vol. 377 No. 26. pp. 2519-2530. Dec. 28, 2017. DOI: 10.1056/NEJMoa1708483.
Related Canadian patent application No. 3,148,964 extended European search report dated Jan. 12, 2024.
(Continued)

*Primary Examiner* — Maria G Leavitt
*Assistant Examiner* — Brendan Thomas Tinsley
(74) *Attorney, Agent, or Firm* — Anglehart et al.

(57) ABSTRACT

This application relates to the fields of gene therapy and molecular biology. More specifically, the present invention relates to an isolated altered VP1 protein of adeno-associated virus serotype 5 (AAV5) capsid comprising one or more amino acid substitutions as compared to the VP1 protein of wild-type AAV5 capsid, which increase transduction efficiency, as well as to a capsid and a vector based thereon.

27 Claims, 6 Drawing Sheets

Specification includes a Sequence Listing.

(56)          References Cited

OTHER PUBLICATIONS

Related European application No. 20855760.3 extended European search report dated Aug. 8, 2023.

Qiao et al. Single tyrosine mutation in AAV8 and AAV9 capsids is insufficient to enhance gene delivery to skeletal muscle and heart. Hum Gene Ther Methods. Feb. 2012;23(1):29-37.

International application No. PCT/RU2020/000445 International Search Report dated Dec. 17, 2020.

International application No. PCT/RU2020/000445 Translation of the International Search Report dated Dec. 17, 2020.

International application No. PCT/RU2020/000445 Written Opinion of the International Searching Authority dated Dec. 17, 2020.

International application No. PCT/RU2020/000445 Translation of theWritten Opinion of the International Searching Authority dated Dec. 17, 2020.

Xie Q. et al. The atomic structure of adeno-associated virus (AAV-2), a vector for human gene therapy. Proc Natl Acad Sci USA, 2002; 99:10405-10410).

High KA et al., rAAV human trial experience. Methods in Molecular Biology. 2011; 807:429-457.

Govindasamy L. et al. Structural insights into adeno-associated virus serotype 5. American Society for Microbiology. Journal of Virology. vol. 87, Issue 20, Oct. 15, 2013, pp. 11187-11199.

Mori, S. et al., 2004, Two novel adeno-associated viruses from cynomolgus monkey: pseudotyping characterization of capsid protein. Virology. vol. 330, Issue 2, Dec. 20, 2004, pp. 375-383.

McLaughlin et al., Adeno-associated virus general transduction vectors: analysis of proviral structures. Journal of Virology. (1988) vol. 62, No. 6:1963-1973.

Davidsson M. et al., A novel process of viral vector barcoding and library preparation enables high-diversity library generation and recombination-free paired-end sequencing. Scientific Reports vol. 6, Article No. 37563 (2016):1-18.

* cited by examiner

SEQUENCE LISTING

```
<160> NUMBER OF SEQ ID NOS: 18

<210> SEQ ID NO 1
<211> LENGTH: 724
<212> TYPE: PRT
<213> ORGANISM: Unknown
<220> FEATURE:
<223> OTHER INFORMATION: The natural sequence of the VP1 protein of the
```

-continued wild-type AAV5 capsid

<400> SEQUENCE: 1

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
                100                 105                 110

Leu Gly Lys Ala Val Phe Gln Ala Lys Lys Arg Val Leu Glu Pro Phe
            115                 120                 125

Gly Leu Val Glu Glu Gly Ala Lys Thr Ala Pro Thr Gly Lys Arg Ile
        130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
    275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400
```

-continued

```
Asn Phe Glu Phe Thr Tyr Asn Phe Glu Glu Val Pro Phe His Ser Ser
                405                     410                     415

Phe Ala Pro Ser Gln Asn Leu Phe Lys Leu Ala Asn Pro Leu Val Asp
            420                     425                     430

Gln Tyr Leu Tyr Arg Phe Val Ser Thr Asn Asn Thr Gly Gly Val Gln
        435                     440                     445

Phe Asn Lys Asn Leu Ala Gly Arg Tyr Ala Asn Thr Tyr Lys Asn Trp
    450                     455                     460

Phe Pro Gly Pro Met Gly Arg Thr Gln Gly Trp Asn Leu Gly Ser Gly
465                     470                     475                     480

Val Asn Arg Ala Ser Val Ser Ala Phe Ala Thr Thr Asn Arg Met Glu
                485                     490                     495

Leu Glu Gly Ala Ser Tyr Gln Val Pro Pro Gln Pro Asn Gly Met Thr
            500                     505                     510

Asn Asn Leu Gln Gly Ser Asn Thr Tyr Ala Leu Glu Asn Thr Met Ile
            515                     520                     525

Phe Asn Ser Gln Pro Ala Asn Pro Gly Thr Thr Ala Thr Tyr Leu Glu
    530                     535                     540

Gly Asn Met Leu Ile Thr Ser Glu Ser Glu Thr Gln Pro Val Asn Arg
545                     550                     555                     560

Val Ala Tyr Asn Val Gly Gly Gln Met Ala Thr Asn Asn Gln Ser Ser
                565                     570                     575

Thr Thr Ala Pro Ala Thr Gly Thr Tyr Asn Leu Gln Glu Ile Val Pro
            580                     585                     590

Gly Ser Val Trp Met Glu Arg Asp Val Tyr Leu Gln Gly Pro Ile Trp
            595                     600                     605

Ala Lys Ile Pro Glu Thr Gly Ala His Phe His Pro Ser Pro Ala Met
    610                     615                     620

Gly Gly Phe Gly Leu Lys His Pro Pro Met Met Leu Ile Lys Asn
625                     630                     635                     640

Thr Pro Val Pro Gly Asn Ile Thr Ser Phe Ser Asp Val Pro Val Ser
            645                     650                     655

Ser Phe Ile Thr Gln Tyr Ser Thr Gly Gln Val Thr Val Glu Met Glu
            660                     665                     670

Trp Glu Leu Lys Lys Glu Asn Ser Lys Arg Trp Asn Pro Glu Ile Gln
            675                     680                     685

Tyr Thr Asn Asn Tyr Asn Asp Pro Gln Phe Val Asp Phe Ala Pro Asp
    690                     695                     700

Ser Thr Gly Glu Tyr Arg Thr Thr Arg Pro Ile Gly Thr Arg Tyr Leu
705                     710                     715                     720

Thr Arg Pro Leu
```

```
<210> SEQ ID NO 2
<211> LENGTH: 724
<212> TYPE: PRT
<213> ORGANISM: Artificial sequence
<220> FEATURE:
<223> OTHER INFORMATION: The isolated altered VP1 protein of the AAV5
      capsid, which includes one substitution in S651A position

<400> SEQUENCE: 2
```

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30
```

-continued

```
Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
        50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
                100                 105                 110

Leu Gly Lys Ala Val Phe Gln Ala Lys Lys Arg Val Leu Glu Pro Phe
            115                 120                 125

Gly Leu Val Glu Glu Gly Ala Lys Thr Ala Pro Thr Gly Lys Arg Ile
        130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
```

-continued

```
            450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
                500                 505                 510

Asn Asn Leu Gln Gly Ser Asn Thr Tyr Ala Leu Glu Asn Thr Met Ile
            515                 520                 525

Phe Asn Ser Gln Pro Ala Asn Pro Gly Thr Thr Ala Thr Tyr Leu Glu
            530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
                580                 585                 590

Gly Ser Val Trp Met Glu Arg Asp Val Tyr Leu Gln Gly Pro Ile Trp
            595                 600                 605

Ala Lys Ile Pro Glu Thr Gly Ala His Phe His Pro Ser Pro Ala Met
            610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ala Asp Val Pro Val Ser
                645                 650                 655

Ser Phe Ile Thr Gln Tyr Ser Thr Gly Gln Val Thr Val Glu Met Glu
                660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
            690                 695                 700

Ser Thr Gly Glu Tyr Arg Thr Thr Arg Pro Ile Gly Thr Arg Tyr Leu
705                 710                 715                 720

Thr Arg Pro Leu
```

```
<210> SEQ ID NO 3
<211> LENGTH: 724
<212> TYPE: PRT
<213> ORGANISM: Artificial sequence
<220> FEATURE:
<223> OTHER INFORMATION: The isolated altered VP1 protein of the AAV5
      capsid, which includes S2A and T711S substitutions

<400> SEQUENCE: 3

Met Ala Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
                20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
            50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
```

```
                85                    90                    95

Ala Glu Phe Gln Glu Lys Leu Ala Asp Asp Thr Ser Phe Gly Gly Asn
            100                  105                  110

Leu Gly Lys Ala Val Phe Gln Ala Lys Lys Arg Val Leu Glu Pro Phe
        115                  120                  125

Gly Leu Val Glu Glu Gly Ala Lys Thr Ala Pro Thr Gly Lys Arg Ile
        130                  135                  140

Asp Asp His Phe Pro Lys Arg Lys Lys Ala Arg Thr Glu Glu Asp Ser
145                  150                  155                  160

Lys Pro Ser Thr Ser Ser Asp Ala Glu Ala Gly Pro Ser Gly Ser Gln
                165                  170                  175

Gln Leu Gln Ile Pro Ala Gln Pro Ala Ser Ser Leu Gly Ala Asp Thr
            180                  185                  190

Met Ser Ala Gly Gly Gly Gly Pro Leu Gly Asp Asn Asn Gln Gly Ala
            195                  200                  205

Asp Gly Val Gly Asn Ala Ser Gly Asp Trp His Cys Asp Ser Thr Trp
    210                  215                  220

Met Gly Asp Arg Val Val Thr Lys Ser Thr Arg Thr Trp Val Leu Pro
225                  230                  235                  240

Ser Tyr Asn Asn His Gln Tyr Arg Glu Ile Lys Ser Gly Ser Val Asp
                245                  250                  255

Gly Ser Asn Ala Asn Ala Tyr Phe Gly Tyr Ser Thr Pro Trp Gly Tyr
            260                  265                  270

Phe Asp Phe Asn Arg Phe His Ser His Trp Ser Pro Arg Asp Trp Gln
            275                  280                  285

Arg Leu Ile Asn Asn Tyr Trp Gly Phe Arg Pro Arg Ser Leu Arg Val
    290                  295                  300

Lys Ile Phe Asn Ile Gln Val Lys Glu Val Thr Val Gln Asp Ser Thr
305                  310                  315                  320

Thr Thr Ile Ala Asn Asn Leu Thr Ser Thr Val Gln Val Phe Thr Asp
            325                  330                  335

Asp Asp Tyr Gln Leu Pro Tyr Val Val Gly Asn Gly Thr Glu Gly Cys
        340                  345                  350

Leu Pro Ala Phe Pro Pro Gln Val Phe Thr Leu Pro Gln Tyr Gly Tyr
        355                  360                  365

Ala Thr Leu Asn Arg Asp Asn Thr Glu Asn Pro Thr Glu Arg Ser Ser
    370                  375                  380

Phe Phe Cys Leu Glu Tyr Phe Pro Ser Lys Met Leu Arg Thr Gly Asn
385                  390                  395                  400

Asn Phe Glu Phe Thr Tyr Asn Phe Glu Glu Val Pro Phe His Ser Ser
            405                  410                  415

Phe Ala Pro Ser Gln Asn Leu Phe Lys Leu Ala Asn Pro Leu Val Asp
            420                  425                  430

Gln Tyr Leu Tyr Arg Phe Val Ser Thr Asn Asn Thr Gly Gly Val Gln
        435                  440                  445

Phe Asn Lys Asn Leu Ala Gly Arg Tyr Ala Asn Thr Tyr Lys Asn Trp
    450                  455                  460

Phe Pro Gly Pro Met Gly Arg Thr Gln Gly Trp Asn Leu Gly Ser Gly
465                  470                  475                  480

Val Asn Arg Ala Ser Val Ser Ala Phe Ala Thr Thr Asn Arg Met Glu
            485                  490                  495

Leu Glu Gly Ala Ser Tyr Gln Val Pro Pro Gln Pro Asn Gly Met Thr
        500                  505                  510
```

-continued

```
Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
        530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
        610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
        690                 695                 700

Ser Thr Gly Glu Tyr Arg Ser Thr Arg Pro Ile Gly Thr Arg Tyr Leu
705                 710                 715                 720

Thr Arg Pro Leu

<210> SEQ ID NO 4
<211> LENGTH: 724
<212> TYPE: PRT
<213> ORGANISM: Artificial sequence
<220> FEATURE:
<223> OTHER INFORMATION: The isolated altered VP1 protein of the AAV5
      capsid protein, which includes 2A, S651A and T711S substitutions

<400> SEQUENCE: 4

Met Ala Phe Val Asp His Pro Pro Asp Trp Leu Glu Glu Val Gly Glu
1                   5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
        50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
        130                 135                 140
```

-continued

```
Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
            195                 200                 205

Asp Gly Val Gly Asn Ala Ser Gly Asp Trp His Cys Asp Ser Thr Trp
        210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
            275                 280                 285

Arg Leu Ile Asn Asn Tyr Trp Gly Phe Arg Pro Arg Ser Leu Arg Val
        290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
        370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
            435                 440                 445

Phe Asn Lys Asn Leu Ala Gly Arg Tyr Ala Asn Thr Tyr Lys Asn Trp
        450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
            515                 520                 525

Phe Asn Ser Gln Pro Ala Asn Pro Gly Thr Thr Ala Thr Tyr Leu Glu
        530                 535                 540

Gly Asn Met Leu Ile Thr Ser Glu Ser Glu Thr Gln Pro Val Asn Arg
545                 550                 555                 560
```

```
Val Ala Tyr Asn Val Gly Gly Gln Met Ala Thr Asn Asn Gln Ser Ser
                565             570             575

Thr Thr Ala Pro Ala Thr Gly Thr Tyr Asn Leu Gln Glu Ile Val Pro
            580             585             590

Gly Ser Val Trp Met Glu Arg Asp Val Tyr Leu Gln Gly Pro Ile Trp
        595             600             605

Ala Lys Ile Pro Glu Thr Gly Ala His Phe His Pro Ser Pro Ala Met
    610             615             620

Gly Gly Phe Gly Leu Lys His Pro Pro Pro Met Met Leu Ile Lys Asn
625             630             635             640

Thr Pro Val Pro Gly Asn Ile Thr Ser Phe Ala Asp Val Pro Val Ser
                645             650             655

Ser Phe Ile Thr Gln Tyr Ser Thr Gly Gln Val Thr Val Glu Met Glu
            660             665             670

Trp Glu Leu Lys Lys Glu Asn Ser Lys Arg Trp Asn Pro Glu Ile Gln
        675             680             685

Tyr Thr Asn Asn Tyr Asn Asp Pro Gln Phe Val Asp Phe Ala Pro Asp
    690             695             700

Ser Thr Gly Glu Tyr Arg Ser Thr Arg Pro Ile Gly Thr Arg Tyr Leu
705             710             715             720

Thr Arg Pro Leu
```

```
<210> SEQ ID NO 5
<211> LENGTH: 2175
<212> TYPE: DNA
<213> ORGANISM: Artificial sequence
<220> FEATURE:
<223> OTHER INFORMATION: The nucleic acid encoding the altered capsid
      protein of adeno-associated virus serotype 5 (AAV5) with S651A
      amino acid substitution

<400> SEQUENCE: 5 atgtctttg ttgatcaccc tccagattgg ttggaagaag ttggtgaagg tcttcgcgag      60
tttttgggcc ttgaagcggg cccaccgaaa ccaaaaccca atcagcagca tcaagatcaa     120
gcccgtggtc ttgtgctgcc tggttataac tatctcggac ccggaaacgg tctcgatcga     180
ggagagcctg tcaacagggc agacgaggtc gcgcgagagc acgacatctc gtacaacgag     240
cagcttgagg cgggagacaa cccctacctc aagtacaacc acgcggacgc cgagtttcag     300
gagaagctcg ccgacgacac atccttcggg ggaaacctcg aaaggcagt ctttcaggcc      360 aagaaaaggt ttctcgaacc ttttggcctg gttgaagagg gtgctaagac ggcccctacc     420
ggaaagcgga tagacgacca ctttccaaaa agaaagaagg ctcggaccga agaggactcc     480
aagccttcca cctcgtcaga cgccgaagct ggacccagcg atccagca gctgcaaatc      540 ccagcccaac cagcctcaag tttgggagct gatacaatgt ctgcgggagg tggcggccca     600
ttgggcgaca ataaccaagg tgccgatgga gtgggcaatg cctcgggaga ttggcattgc     660
gattccacgt ggatggggga cagagtcgtc accaagtcca cccgaacctg ggtgctgccc     720
agctacaaca ccaccagta ccgagagatc aaaagcggct ccgtcgacgg aagcaacgcc      780
aacgcctact ttggatacag cacccctgg gggtactttg actttaaccg cttccacagc      840
cactggagcc cccgagactg gcaaagactc atcaacaact actggggctt cagaccccgg     900
tccctcagag tcaaaatctt caacattcaa gtcaaagagg tcacggtgca ggactccacc     960
accaccatcg ccaacaacct cacctccacc gtccaagtgt ttacggacga cgactaccag    1020
ctgccctacg tcgtcggcaa cgggaccgag ggatgcctgc cggccttccc tccgcaggtc    1080
```

-continued

```
tttacgctgc cgcagtacgg ttacgcgacg ctgaaccgcg acaacacaga aaatcccacc      1140
gagaggagca gcttcttctg cctagagtac tttcccagca agatgctgag aacgggcaac      1200
aactttgagt ttacctacaa ctttgaggag gtgcccttcc actccagctt cgctcccagt      1260
cagaacctgt tcaagctggc caacccgctg gtggaccagt acttgtaccg cttcgtgagc      1320
acaaataaca ctggcggagt ccagttcaac aagaacctgg ccgggagata cgccaacacc      1380
tacaaaaact ggttcccggg gcccatgggc cgaacccagg ctggaacct gggctccggg        1440 gtcaaccgcg ccagtgtcag cgccttcgcc acgaccaata ggatggagct cgagggcgcg      1500
agttaccagg tgcccccgca gccgaacggc atgaccaaca acctccaggg cagcaacacc      1560
tatgccctgg agaacactat gatcttcaac agccagccgg cgaacccggg caccaccgcc      1620
acgtacctcg agggcaacat gctcatcacc agcgagagcg agacgcagcc ggtgaaccgc      1680
gtggcgtaca acgtcggcgg gcagatggcc accaacaacc agagctccac cactgccccc      1740
gcgaccggca cgtacaacct ccaggaaatc gtgcccggca cgtgtggat ggagagggac        1800 gtgtacctcc aaggacccat ctgggccaag atcccagaga cggggggcgca ctttcacccc      1860 tctccggcca tgggcggatt cggactcaaa cacccaccgc ccatgatgct catcaagaac      1920
acgcctgtgc ccggaaatat caccagcttc gcggacgtgc ccgtcagcag cttcatcacc      1980
cagtacagca ccgggcaggt caccgtggag atggagtggg agctcaagaa ggaaaactcc      2040
aagaggtgga acccagagat ccagtacaca aacaactaca acgaccccca gtttgtggac      2100
tttgccccgg acagcaccgg ggaatacaga accaccagac ctatcggaac ccgatacctt      2160
acccgacccc tttaa                                                         2175
```

<210> SEQ ID NO 6
<211> LENGTH: 2175
<212> TYPE: DNA
<213> ORGANISM: Artificial sequence
<220> FEATURE:
<223> OTHER INFORMATION: The nucleic acid encoding the altered capsid
      protein of adeno-associated virus serotype 5 (AAV5) with S2A and
      T711S amino acid substitutions

<400> SEQUENCE: 6

```
atggctttg ttgatcaccc tccagattgg ttggaagaag ttggtgaagg tcttcgcgag         60 ttttgggcc ttgaagcggg cccaccgaaa ccaaaaccca atcagcagca tcaagatcaa        120
gcccgtggtc ttgtgctgcc tggttataac tatctcggac ccggaaacgg tctcgatcga       180
ggagagcctg tcaacagggc agacgaggtc gcgcgagagc acgacatctc gtacaacgag       240
cagcttgagg cgggagacaa ccccttacctc aagtacaacc acgcggacgc cgagtttcag      300
gagaagctcg ccgacgacac atccttcggg ggaaacctcg aaaggcagt ctttcaggcc         360 aagaaaaggg ttctcgaacc ttttggcctg gttgaagagg gtgctaagac ggcccctacc       420
ggaaagcgga tagacgacca cttttccaaaa agaaagaagg ctcggaccga agaggactcc      480
aagccttcca cctcgtcaga cgccgaagct ggacccagcg gatcccagca gctgcaaatc       540
ccagcccaac cagcctcaag tttgggagct gatacaatgt ctgcgggagg tggcggccca       600
ttgggcgaca ataaccaagg tgccgatgga gtgggcaatg cctcgggaga ttggcattgc       660
gattccacgt ggatggggga cagagtcgtc accaagtcca cccgaacctg ggtgctgccc       720
agctacaaca accaccagta ccgagagatc aaaagcggct ccgtcgacgg aagcaacgcc       780
aacgcctact ttggatacag caccccctgg gggtactttg actttaaccg cttccacagc       840
```

-continued

```
cactggagcc cccgagactg gcaaagactc atcaacaact actgggggctt cagacccggg    900 tccctcagag tcaaaatctt caacattcaa gtcaaagagg tcacggtgca ggactccacc    960
accaccatcg ccaacaacct cacctccacc gtccaagtgt ttacggacga cgactaccag   1020
ctgccctacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca agatgctgag aacgggcaac   1200
aactttgagt ttacctacaa cttttgaggag gtgcccttcc actccagctt cgctcccagt   1260
cagaacctct tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg ctggaacct gggctccggg    1440 gtcaaccgcg ccagtgtcag cgccttcgcc acgaccaata ggatggagct cgagggcgcg   1500
agttaccagg tgcccccgca gccgaacggc atgaccaaca acctccaggg cagcaacacc   1560
tatgccctgg agaacactat gatcttcaac agccagccgg cgaacccggg caccaccgcc   1620
acgtacctcg agggcaacat gctcatcacc agcgagagcg agacgcagcc ggtgaaccgc   1680
gtggcgtaca cgtcggcgg gcagatggcc accaacaacc agagctccac cactgccccc    1740
gcgaccggca cgtacaacct ccaggaaatc gtgcccggca gcgtgtggat ggagagggac   1800
gtgtacctcc aaggacccat ctgggccaag atcccagaga cggggggcgca ctttcacccc   1860 tctccggcca tgggcggatt cggactcaaa cacccaccgc ccatgatgct catcaagaac   1920
acgcctgtgc ccgaaatat caccagcttc tcggacgtgc ccgtcagcag cttcatcacc    1980
cagtacagca ccgggcaggt caccgtggag atggagtggg agctcaagaa ggaaaactcc    2040
aagaggtgga acccagagat ccagtacaca aacaactaca cgaccccca gtttgtggac    2100 tttgccccgg acagcaccgg ggaatacaga agcaccagac ctatcggaac ccgatacctt    2160
acccgacccc tttaa                                                     2175
```

<210> SEQ ID NO 7
<211> LENGTH: 2175
<212> TYPE: DNA
<213> ORGANISM: Artificial sequence
<220> FEATURE:
<223> OTHER INFORMATION: The nucleic acid encoding the altered capsid
      protein of adeno-associated virus serotype 5 (AAV5) with S2A,
      S651A and T711S amino acid substitutions

<400> SEQUENCE: 7

```
atggctttg ttgatcaccc tccagattgg ttggaagaag ttggtgaagg tcttcgcgag     60 ttttttgggcc ttgaagcggg cccaccgaaa ccaaaaccca atcagcagca tcaagatcaa    120
gcccgtggtc ttgtgctgcc tggttataac tatctcggac ccggaaacgg tctcgatcga    180
ggagagcctg tcaacagggc agacgaggtc gcgcgagagc acgacatctc gtacaacgag    240
cagcttgagg cgggagacaa cccctacctc aagtacaacc acgcggacgc cgagtttcag    300
gagaagctcg ccgacgacac atccttcggg ggaaacctcg aaaggcagt ctttcaggcc     360 aagaaaaggg ttctcgaacc ttttggcctg gttgaagagg gtgctaagac ggcccctacc    420
ggaaagcgga tagacgacca ctttccaaaa agaaagaagg ctcggaccga gaggactcc     480 aagccttcca cctcgtcaga cgccgaagct ggacccagcg atccagcca gctgcaaatc     540 ccagcccaac cagcctcaag tttggagct gatacaatgt ctgcggggagg tggcggccca    600 ttgggcgaca ataaccaagg tgccgatgga gtgggcaatg cctcgggaga ttggcattgc    660
```

-continued

```
gattccacgt ggatggggga cagagtcgtc accaagtcca cccgaacctg ggtgctgccc    720
agctacaaca accaccagta ccgagagatc aaaagcggct ccgtcgacgg aagcaacgcc    780
aacgcctact ttggatacag cacccctgg gggtactttg actttaaccg cttccacagc     840
cactggagcc cccgagactg gcaaagactc atcaacaact actggggctt cagaccccgg    900
tccctcagag tcaaaatctt caacattcaa gtcaaagagg tcacggtgca ggactccacc    960
accaccatcg ccaacaacct cacctccacc gtccaagtgt ttacggacga cgactaccag   1020
ctgccctacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca agatgctgag aacgggcaac   1200
aactttgagt ttacctacaa ctttgaggag gtgcccttcc actccagctt cgctcccagt   1260
cagaacctct tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg ctggaacct gggctccggg    1440 gtcaaccgcg ccagtgtcag cgccttcgcc acgaccaata ggatggagct cgagggcgcg   1500
agttaccagg tgcccccgca gccgaacggc atgaccaaca acctccaggg cagcaacacc   1560
tatgccctgg agaacactat gatcttcaac agccagccgg cgaacccggg caccaccgcc   1620
acgtacctcg agggcaacat gctcatcacc agcgagagcg agacgcagcc ggtgaaccgc   1680
gtggcgtaca cgtcggcgg gcagatggcc accaacaacc agagctccac cactgccccc   1740
gcgaccggca cgtacaacct ccaggaaatc gtgcccggca gcgtgtggat ggagagggac   1800
gtgtacctcc aaggacccat ctgggccaag atcccagaga cggggggcgca ctttcacccc   1860 tctccggcca tgggcggatt cggactcaaa cacccaccgc ccatgatgct catcaagaac   1920
acgcctgtgc ccggaaatat caccagcttc gcggacgtgc ccgtcagcag cttcatcacc   1980
cagtacagca ccgggcaggt caccgtggag atggagtggg agctcaagaa ggaaaactcc   2040
aagaggtgga acccagagat ccagtacaca aacaactaca cgaccccca gtttgtggac    2100 tttgccccgg acagcaccgg ggaatacaga agcaccagac tatcggaac ccgatacctt    2160 acccgacccc tttaa                                                    2175
```

<210> SEQ ID NO 8
<211> LENGTH: 588
<212> TYPE: PRT
<213> ORGANISM: Unknown
<220> FEATURE:
<223> OTHER INFORMATION: The isolated amino acid sequence of the VP2
      protein of the wild-type AAV5 capsid

<400> SEQUENCE: 8

```
Thr Ala Pro Thr Gly Lys Arg Ile Asp Asp His Phe Pro Lys Arg Lys
1               5                   10                  15

Lys Ala Arg Thr Glu Glu Asp Ser Lys Pro Ser Thr Ser Ser Asp Ala
            20                  25                  30

Glu Ala Gly Pro Ser Gly Ser Gln Gln Leu Gln Ile Pro Ala Gln Pro
        35                  40                  45

Ala Ser Ser Leu Gly Ala Asp Thr Met Ser Ala Gly Gly Gly Gly Pro
    50                  55                  60

Leu Gly Asp Asn Asn Gln Gly Ala Asp Gly Val Gly Asn Ala Ser Gly
65                  70                  75                  80
```

```
Asp Trp His Cys Asp Ser Thr Trp Met Gly Asp Arg Val Val Thr Lys
            85              90              95

Ser Thr Arg Thr Trp Val Leu Pro Ser Tyr Asn Asn His Gln Tyr Arg
            100             105             110

Glu Ile Lys Ser Gly Ser Val Asp Gly Ser Asn Ala Asn Ala Tyr Phe
            115             120             125

Gly Tyr Ser Thr Pro Trp Gly Tyr Phe Asp Phe Asn Arg Phe His Ser
    130             135             140

His Trp Ser Pro Arg Asp Trp Gln Arg Leu Ile Asn Asn Tyr Trp Gly
145             150             155             160

Phe Arg Pro Arg Ser Leu Arg Val Lys Ile Phe Asn Ile Gln Val Lys
                165             170             175

Glu Val Thr Val Gln Asp Ser Thr Thr Thr Ile Ala Asn Asn Leu Thr
            180             185             190

Ser Thr Val Gln Val Phe Thr Asp Asp Asp Tyr Gln Leu Pro Tyr Val
            195             200             205

Val Gly Asn Gly Thr Glu Gly Cys Leu Pro Ala Phe Pro Pro Gln Val
    210             215             220

Phe Thr Leu Pro Gln Tyr Gly Tyr Ala Thr Leu Asn Arg Asp Asn Thr
225             230             235             240

Glu Asn Pro Thr Glu Arg Ser Ser Phe Phe Cys Leu Glu Tyr Phe Pro
            245             250             255

Ser Lys Met Leu Arg Thr Gly Asn Asn Phe Glu Phe Thr Tyr Asn Phe
            260             265             270

Glu Glu Val Pro Phe His Ser Ser Phe Ala Pro Ser Gln Asn Leu Phe
            275             280             285

Lys Leu Ala Asn Pro Leu Val Asp Gln Tyr Leu Tyr Arg Phe Val Ser
    290             295             300

Thr Asn Asn Thr Gly Gly Val Gln Phe Asn Lys Asn Leu Ala Gly Arg
305             310             315             320

Tyr Ala Asn Thr Tyr Lys Asn Trp Phe Pro Gly Pro Met Gly Arg Thr
                325             330             335

Gln Gly Trp Asn Leu Gly Ser Gly Val Asn Arg Ala Ser Val Ser Ala
            340             345             350

Phe Ala Thr Thr Asn Arg Met Glu Leu Glu Gly Ala Ser Tyr Gln Val
            355             360             365

Pro Pro Gln Pro Asn Gly Met Thr Asn Asn Leu Gln Gly Ser Asn Thr
    370             375             380

Tyr Ala Leu Glu Asn Thr Met Ile Phe Asn Ser Gln Pro Ala Asn Pro
385             390             395             400

Gly Thr Thr Ala Thr Tyr Leu Glu Gly Asn Met Leu Ile Thr Ser Glu
                405             410             415

Ser Glu Thr Gln Pro Val Asn Arg Val Ala Tyr Asn Val Gly Gly Gln
            420             425             430

Met Ala Thr Asn Asn Gln Ser Ser Thr Thr Ala Pro Ala Thr Gly Thr
            435             440             445

Tyr Asn Leu Gln Glu Ile Val Pro Gly Ser Val Trp Met Glu Arg Asp
    450             455             460

Val Tyr Leu Gln Gly Pro Ile Trp Ala Lys Ile Pro Glu Thr Gly Ala
465             470             475             480

His Phe His Pro Ser Pro Ala Met Gly Gly Phe Gly Leu Lys His Pro
                485             490             495

Pro Pro Met Met Leu Ile Lys Asn Thr Pro Val Pro Gly Asn Ile Thr
```

-continued

```
               500              505              510

Ser Phe Ser Asp Val Pro Val Ser Ser Phe Ile Thr Gln Tyr Ser Thr
        515              520              525

Gly Gln Val Thr Val Glu Met Glu Trp Glu Leu Lys Lys Glu Asn Ser
    530              535              540

Lys Arg Trp Asn Pro Glu Ile Gln Tyr Thr Asn Asn Tyr Asn Asp Pro
545              550              555              560

Gln Phe Val Asp Phe Ala Pro Asp Ser Thr Gly Glu Tyr Arg Thr Thr
            565              570              575

Arg Pro Ile Gly Thr Arg Tyr Leu Thr Arg Pro Leu
            580              585

<210> SEQ ID NO 9
<211> LENGTH: 588
<212> TYPE: PRT
<213> ORGANISM: Artificial sequence
<220> FEATURE:
<223> OTHER INFORMATION: The isolated altered VP2 protein of the AAV5
      capsid, which includes T575S substitution

<400> SEQUENCE: 9

Thr Ala Pro Thr Gly Lys Arg Ile Asp Asp His Phe Pro Lys Arg Lys
1               5               10              15

Lys Ala Arg Thr Glu Glu Asp Ser Lys Pro Ser Thr Ser Ser Asp Ala
            20              25              30

Glu Ala Gly Pro Ser Gly Ser Gln Gln Leu Gln Ile Pro Ala Gln Pro
        35              40              45

Ala Ser Ser Leu Gly Ala Asp Thr Met Ser Ala Gly Gly Gly Gly Pro
    50              55              60

Leu Gly Asp Asn Asn Gln Gly Ala Asp Gly Val Gly Asn Ala Ser Gly
65              70              75              80

Asp Trp His Cys Asp Ser Thr Trp Met Gly Asp Arg Val Val Thr Lys
            85              90              95

Ser Thr Arg Thr Trp Val Leu Pro Ser Tyr Asn Asn His Gln Tyr Arg
            100             105             110

Glu Ile Lys Ser Gly Ser Val Asp Gly Ser Asn Ala Asn Ala Tyr Phe
        115             120             125

Gly Tyr Ser Thr Pro Trp Gly Tyr Phe Asp Phe Asn Arg Phe His Ser
    130             135             140

His Trp Ser Pro Arg Asp Trp Gln Arg Leu Ile Asn Asn Tyr Trp Gly
145             150             155             160

Phe Arg Pro Arg Ser Leu Arg Val Lys Ile Phe Asn Ile Gln Val Lys
            165             170             175

Glu Val Thr Val Gln Asp Ser Thr Thr Thr Ile Ala Asn Asn Leu Thr
            180             185             190

Ser Thr Val Gln Val Phe Thr Asp Asp Asp Tyr Gln Leu Pro Tyr Val
        195             200             205

Val Gly Asn Gly Thr Glu Gly Cys Leu Pro Ala Phe Pro Pro Gln Val
    210             215             220

Phe Thr Leu Pro Gln Tyr Gly Tyr Ala Thr Leu Asn Arg Asp Asn Thr
225             230             235             240

Glu Asn Pro Thr Glu Arg Ser Ser Phe Phe Cys Leu Glu Tyr Phe Pro
            245             250             255

Ser Lys Met Leu Arg Thr Gly Asn Asn Phe Glu Phe Thr Tyr Asn Phe
            260             265             270
```

-continued

```
Glu Glu Val Pro Phe His Ser Ser Phe Ala Pro Ser Gln Asn Leu Phe
        275             280             285

Lys Leu Ala Asn Pro Leu Val Asp Gln Tyr Leu Tyr Arg Phe Val Ser
    290             295             300

Thr Asn Asn Thr Gly Gly Val Gln Phe Asn Lys Asn Leu Ala Gly Arg
305             310             315             320

Tyr Ala Asn Thr Tyr Lys Asn Trp Phe Pro Gly Pro Met Gly Arg Thr
            325             330             335

Gln Gly Trp Asn Leu Gly Ser Gly Val Asn Arg Ala Ser Val Ser Ala
            340             345             350

Phe Ala Thr Thr Asn Arg Met Glu Leu Glu Gly Ala Ser Tyr Gln Val
            355             360             365

Pro Pro Gln Pro Asn Gly Met Thr Asn Asn Leu Gln Gly Ser Asn Thr
    370             375             380

Tyr Ala Leu Glu Asn Thr Met Ile Phe Asn Ser Gln Pro Ala Asn Pro
385             390             395             400

Gly Thr Thr Ala Thr Tyr Leu Glu Gly Asn Met Leu Ile Thr Ser Glu
            405             410             415

Ser Glu Thr Gln Pro Val Asn Arg Val Ala Tyr Asn Val Gly Gly Gln
            420             425             430

Met Ala Thr Asn Asn Gln Ser Ser Thr Thr Ala Pro Ala Thr Gly Thr
            435             440             445

Tyr Asn Leu Gln Glu Ile Val Pro Gly Ser Val Trp Met Glu Arg Asp
    450             455             460

Val Tyr Leu Gln Gly Pro Ile Trp Ala Lys Ile Pro Glu Thr Gly Ala
465             470             475             480

His Phe His Pro Ser Pro Ala Met Gly Gly Phe Gly Leu Lys His Pro
            485             490             495

Pro Pro Met Met Leu Ile Lys Asn Thr Pro Val Pro Gly Asn Ile Thr
            500             505             510

Ser Phe Ser Asp Val Pro Val Ser Ser Phe Ile Thr Gln Tyr Ser Thr
            515             520             525

Gly Gln Val Thr Val Glu Met Glu Trp Glu Leu Lys Lys Glu Asn Ser
    530             535             540

Lys Arg Trp Asn Pro Glu Ile Gln Tyr Thr Asn Asn Tyr Asn Asp Pro
545             550             555             560

Gln Phe Val Asp Phe Ala Pro Asp Ser Thr Gly Glu Tyr Arg Ser Thr
            565             570             575

Arg Pro Ile Gly Thr Arg Tyr Leu Thr Arg Pro Leu
            580             585
```

<210> SEQ ID NO 10
<211> LENGTH: 588
<212> TYPE: PRT
<213> ORGANISM: Artificial sequence
<220> FEATURE:
<223> OTHER INFORMATION: The isolated altered VP2 protein of the AAV5
      capsid, which includes S515A and T575S substitutions

<400> SEQUENCE: 10

```
Thr Ala Pro Thr Gly Lys Arg Ile Asp Asp His Phe Pro Lys Arg Lys
1               5               10              15

Lys Ala Arg Thr Glu Glu Asp Ser Lys Pro Ser Thr Ser Ser Asp Ala
            20              25              30

Glu Ala Gly Pro Ser Gly Ser Gln Gln Leu Gln Ile Pro Ala Gln Pro
            35              40              45
```

-continued

```
Ala Ser Ser Leu Gly Ala Asp Thr Met Ser Ala Gly Gly Gly Gly Pro
    50              55              60

Leu Gly Asp Asn Asn Gln Gly Ala Asp Gly Val Gly Asn Ala Ser Gly
65              70              75              80

Asp Trp His Cys Asp Ser Thr Trp Met Gly Asp Arg Val Val Thr Lys
            85              90              95

Ser Thr Arg Thr Trp Val Leu Pro Ser Tyr Asn Asn His Gln Tyr Arg
        100             105             110

Glu Ile Lys Ser Gly Ser Val Asp Gly Ser Asn Ala Asn Ala Tyr Phe
        115             120             125

Gly Tyr Ser Thr Pro Trp Gly Tyr Phe Asp Phe Asn Arg Phe His Ser
    130             135             140

His Trp Ser Pro Arg Asp Trp Gln Arg Leu Ile Asn Asn Tyr Trp Gly
145             150             155             160

Phe Arg Pro Arg Ser Leu Arg Val Lys Ile Phe Asn Ile Gln Val Lys
                165             170             175

Glu Val Thr Val Gln Asp Ser Thr Thr Thr Ile Ala Asn Asn Leu Thr
            180             185             190

Ser Thr Val Gln Val Phe Thr Asp Asp Asp Tyr Gln Leu Pro Tyr Val
        195             200             205

Val Gly Asn Gly Thr Glu Gly Cys Leu Pro Ala Phe Pro Pro Gln Val
    210             215             220

Phe Thr Leu Pro Gln Tyr Gly Tyr Ala Thr Leu Asn Arg Asp Asn Thr
225             230             235             240

Glu Asn Pro Thr Glu Arg Ser Ser Phe Phe Cys Leu Glu Tyr Phe Pro
            245             250             255

Ser Lys Met Leu Arg Thr Gly Asn Asn Phe Glu Phe Thr Tyr Asn Phe
            260             265             270

Glu Glu Val Pro Phe His Ser Ser Phe Ala Pro Ser Gln Asn Leu Phe
        275             280             285

Lys Leu Ala Asn Pro Leu Val Asp Gln Tyr Leu Tyr Arg Phe Val Ser
    290             295             300

Thr Asn Asn Thr Gly Gly Val Gln Phe Asn Lys Asn Leu Ala Gly Arg
305             310             315             320

Tyr Ala Asn Thr Tyr Lys Asn Trp Phe Pro Gly Pro Met Gly Arg Thr
            325             330             335

Gln Gly Trp Asn Leu Gly Ser Gly Val Asn Arg Ala Ser Val Ser Ala
            340             345             350

Phe Ala Thr Thr Asn Arg Met Glu Leu Glu Gly Ala Ser Tyr Gln Val
            355             360             365

Pro Pro Gln Pro Asn Gly Met Thr Asn Asn Leu Gln Gly Ser Asn Thr
    370             375             380

Tyr Ala Leu Glu Asn Thr Met Ile Phe Asn Ser Gln Pro Ala Asn Pro
385             390             395             400

Gly Thr Thr Ala Thr Tyr Leu Glu Gly Asn Met Leu Ile Thr Ser Glu
                405             410             415

Ser Glu Thr Gln Pro Val Asn Arg Val Ala Tyr Asn Val Gly Gly Gln
            420             425             430

Met Ala Thr Asn Asn Gln Ser Ser Thr Thr Ala Pro Ala Thr Gly Thr
            435             440             445

Tyr Asn Leu Gln Glu Ile Val Pro Gly Ser Val Trp Met Glu Arg Asp
    450             455             460
```

-continued

```
Val Tyr Leu Gln Gly Pro Ile Trp Ala Lys Ile Pro Glu Thr Gly Ala
465             470             475             480

His Phe His Pro Ser Pro Ala Met Gly Gly Phe Gly Leu Lys His Pro
                485             490             495

Pro Pro Met Met Leu Ile Lys Asn Thr Pro Val Pro Gly Asn Ile Thr
            500             505             510

Ser Phe Ala Asp Val Pro Val Ser Ser Phe Ile Thr Gln Tyr Ser Thr
            515             520             525

Gly Gln Val Thr Val Glu Met Glu Trp Glu Leu Lys Lys Glu Asn Ser
            530             535             540

Lys Arg Trp Asn Pro Glu Ile Gln Tyr Thr Asn Asn Tyr Asn Asp Pro
545             550             555             560

Gln Phe Val Asp Phe Ala Pro Asp Ser Thr Gly Glu Tyr Arg Ser Thr
                565             570             575

Arg Pro Ile Gly Thr Arg Tyr Leu Thr Arg Pro Leu
                580             585
```

```
<210> SEQ ID NO 11
<211> LENGTH: 532
<212> TYPE: PRT
<213> ORGANISM: Unknown
<220> FEATURE:
<223> OTHER INFORMATION: The amino acid sequence of the VP3 protein of
      the wild-type AAV5 capsid

<400> SEQUENCE: 11

Met Ser Ala Gly Gly Gly Gly Pro Leu Gly Asp Asn Asn Gln Gly Ala
1               5               10              15

Asp Gly Val Gly Asn Ala Ser Gly Asp Trp His Cys Asp Ser Thr Trp
                20              25              30

Met Gly Asp Arg Val Val Thr Lys Ser Thr Arg Thr Trp Val Leu Pro
            35              40              45

Ser Tyr Asn Asn His Gln Tyr Arg Glu Ile Lys Ser Gly Ser Val Asp
    50              55              60

Gly Ser Asn Ala Asn Ala Tyr Phe Gly Tyr Ser Thr Pro Trp Gly Tyr
65              70              75              80

Phe Asp Phe Asn Arg Phe His Ser His Trp Ser Pro Arg Asp Trp Gln
                85              90              95

Arg Leu Ile Asn Asn Tyr Trp Gly Phe Arg Pro Arg Ser Leu Arg Val
            100             105             110

Lys Ile Phe Asn Ile Gln Val Lys Glu Val Thr Val Gln Asp Ser Thr
            115             120             125

Thr Thr Ile Ala Asn Asn Leu Thr Ser Thr Val Gln Val Phe Thr Asp
            130             135             140

Asp Asp Tyr Gln Leu Pro Tyr Val Val Gly Asn Gly Thr Glu Gly Cys
145             150             155             160

Leu Pro Ala Phe Pro Pro Gln Val Phe Thr Leu Pro Gln Tyr Gly Tyr
                165             170             175

Ala Thr Leu Asn Arg Asp Asn Thr Glu Asn Pro Thr Glu Arg Ser Ser
            180             185             190

Phe Phe Cys Leu Glu Tyr Phe Pro Ser Lys Met Leu Arg Thr Gly Asn
            195             200             205

Asn Phe Glu Phe Thr Tyr Asn Phe Glu Glu Val Pro Phe His Ser Ser
    210             215             220

Phe Ala Pro Ser Gln Asn Leu Phe Lys Leu Ala Asn Pro Leu Val Asp
225             230             235             240
```

```
Gln Tyr Leu Tyr Arg Phe Val Ser Thr Asn Asn Thr Gly Gly Val Gln
                245                 250                 255

Phe Asn Lys Asn Leu Ala Gly Arg Tyr Ala Asn Thr Tyr Lys Asn Trp
                260                 265                 270

Phe Pro Gly Pro Met Gly Arg Thr Gln Gly Trp Asn Leu Gly Ser Gly
                275                 280                 285

Val Asn Arg Ala Ser Val Ser Ala Phe Ala Thr Thr Asn Arg Met Glu
                290                 295                 300

Leu Glu Gly Ala Ser Tyr Gln Val Pro Pro Gln Pro Asn Gly Met Thr
305                 310                 315                 320

Asn Asn Leu Gln Gly Ser Asn Thr Tyr Ala Leu Glu Asn Thr Met Ile
                325                 330                 335

Phe Asn Ser Gln Pro Ala Asn Pro Gly Thr Thr Ala Thr Tyr Leu Glu
                340                 345                 350

Gly Asn Met Leu Ile Thr Ser Glu Ser Glu Thr Gln Pro Val Asn Arg
                355                 360                 365

Val Ala Tyr Asn Val Gly Gly Gln Met Ala Thr Asn Asn Gln Ser Ser
                370                 375                 380

Thr Thr Ala Pro Ala Thr Gly Thr Tyr Asn Leu Gln Glu Ile Val Pro
385                 390                 395                 400

Gly Ser Val Trp Met Glu Arg Asp Val Tyr Leu Gln Gly Pro Ile Trp
                405                 410                 415

Ala Lys Ile Pro Glu Thr Gly Ala His Phe His Pro Ser Pro Ala Met
                420                 425                 430

Gly Gly Phe Gly Leu Lys His Pro Pro Pro Met Met Leu Ile Lys Asn
                435                 440                 445

Thr Pro Val Pro Gly Asn Ile Thr Ser Phe Ser Asp Val Pro Val Ser
                450                 455                 460

Ser Phe Ile Thr Gln Tyr Ser Thr Gly Gln Val Thr Val Glu Met Glu
465                 470                 475                 480

Trp Glu Leu Lys Lys Glu Asn Ser Lys Arg Trp Asn Pro Glu Ile Gln
                485                 490                 495

Tyr Thr Asn Asn Tyr Asn Asp Pro Gln Phe Val Asp Phe Ala Pro Asp
                500                 505                 510

Ser Thr Gly Glu Tyr Arg Thr Thr Arg Pro Ile Gly Thr Arg Tyr Leu
                515                 520                 525

Thr Arg Pro Leu
    530
```

```
<210> SEQ ID NO 12
<211> LENGTH: 532
<212> TYPE: PRT
<213> ORGANISM: Artificial sequence
<220> FEATURE:
<223> OTHER INFORMATION: The isolated altered VP3 protein of the AAV5
      capsid, which includes T519S substitution

<400> SEQUENCE: 12

Met Ser Ala Gly Gly Gly Gly Pro Leu Gly Asp Asn Asn Gln Gly Ala
1               5                   10                  15

Asp Gly Val Gly Asn Ala Ser Gly Asp Trp His Cys Asp Ser Thr Trp
                20                  25                  30

Met Gly Asp Arg Val Val Thr Lys Ser Thr Arg Thr Trp Val Leu Pro
                35                  40                  45

Ser Tyr Asn Asn His Gln Tyr Arg Glu Ile Lys Ser Gly Ser Val Asp
```

-continued

```
          50                    55                    60

Gly Ser Asn Ala Asn Ala Tyr Phe Gly Tyr Ser Thr Pro Trp Gly Tyr
65                  70                  75                  80

Phe Asp Phe Asn Arg Phe His Ser His Trp Ser Pro Arg Asp Trp Gln
                85                  90                  95

Arg Leu Ile Asn Asn Tyr Trp Gly Phe Arg Pro Arg Ser Leu Arg Val
                100                 105                 110

Lys Ile Phe Asn Ile Gln Val Lys Glu Val Thr Val Gln Asp Ser Thr
            115                 120                 125

Thr Thr Ile Ala Asn Asn Leu Thr Ser Thr Val Gln Val Phe Thr Asp
        130                 135                 140

Asp Asp Tyr Gln Leu Pro Tyr Val Val Gly Asn Gly Thr Glu Gly Cys
145                 150                 155                 160

Leu Pro Ala Phe Pro Pro Gln Val Phe Thr Leu Pro Gln Tyr Gly Tyr
                165                 170                 175

Ala Thr Leu Asn Arg Asp Asn Thr Glu Asn Pro Thr Glu Arg Ser Ser
            180                 185                 190

Phe Phe Cys Leu Glu Tyr Phe Pro Ser Lys Met Leu Arg Thr Gly Asn
        195                 200                 205

Asn Phe Glu Phe Thr Tyr Asn Phe Glu Glu Val Pro Phe His Ser Ser
    210                 215                 220

Phe Ala Pro Ser Gln Asn Leu Phe Lys Leu Ala Asn Pro Leu Val Asp
225                 230                 235                 240

Gln Tyr Leu Tyr Arg Phe Val Ser Thr Asn Asn Thr Gly Gly Val Gln
                245                 250                 255

Phe Asn Lys Asn Leu Ala Gly Arg Tyr Ala Asn Thr Tyr Lys Asn Trp
            260                 265                 270

Phe Pro Gly Pro Met Gly Arg Thr Gln Gly Trp Asn Leu Gly Ser Gly
        275                 280                 285

Val Asn Arg Ala Ser Val Ser Ala Phe Ala Thr Thr Asn Arg Met Glu
    290                 295                 300

Leu Glu Gly Ala Ser Tyr Gln Val Pro Pro Gln Pro Asn Gly Met Thr
305                 310                 315                 320

Asn Asn Leu Gln Gly Ser Asn Thr Tyr Ala Leu Glu Asn Thr Met Ile
            325                 330                 335

Phe Asn Ser Gln Pro Ala Asn Pro Gly Thr Thr Ala Thr Tyr Leu Glu
            340                 345                 350

Gly Asn Met Leu Ile Thr Ser Glu Ser Glu Thr Gln Pro Val Asn Arg
        355                 360                 365

Val Ala Tyr Asn Val Gly Gly Gln Met Ala Thr Asn Asn Gln Ser Ser
    370                 375                 380

Thr Thr Ala Pro Ala Thr Gly Thr Tyr Asn Leu Gln Glu Ile Val Pro
385                 390                 395                 400

Gly Ser Val Trp Met Glu Arg Asp Val Tyr Leu Gln Gly Pro Ile Trp
                405                 410                 415

Ala Lys Ile Pro Glu Thr Gly Ala His Phe His Pro Ser Pro Ala Met
            420                 425                 430

Gly Gly Phe Gly Leu Lys His Pro Pro Pro Met Met Leu Ile Lys Asn
        435                 440                 445

Thr Pro Val Pro Gly Asn Ile Thr Ser Phe Ser Asp Val Pro Val Ser
    450                 455                 460

Ser Phe Ile Thr Gln Tyr Ser Thr Gly Gln Val Thr Val Glu Met Glu
465                 470                 475                 480
```

-continued

Trp Glu Leu Lys Lys Glu Asn Ser Lys Arg Trp Asn Pro Glu Ile Gln
                485                 490                 495

Tyr Thr Asn Asn Tyr Asn Asp Pro Gln Phe Val Asp Phe Ala Pro Asp
            500                 505                 510

Ser Thr Gly Glu Tyr Arg Ser Thr Arg Pro Ile Gly Thr Arg Tyr Leu
        515                 520                 525

Thr Arg Pro Leu
    530

<210> SEQ ID NO 13
<211> LENGTH: 532
<212> TYPE: PRT
<213> ORGANISM: Artificial sequence
<220> FEATURE:
<223> OTHER INFORMATION: The isolated altered VP3 protein of the AAV5
      capsid, which includes S459A and T519S substitutions

<400> SEQUENCE: 13

Met Ser Ala Gly Gly Gly Pro Leu Gly Asp Asn Asn Gln Gly Ala
1               5                   10                  15

Asp Gly Val Gly Asn Ala Ser Gly Asp Trp His Cys Asp Ser Thr Trp
            20                  25                  30

Met Gly Asp Arg Val Val Thr Lys Ser Thr Arg Thr Trp Val Leu Pro
        35                  40                  45

Ser Tyr Asn Asn His Gln Tyr Arg Glu Ile Lys Ser Gly Ser Val Asp
    50                  55                  60

Gly Ser Asn Ala Asn Ala Tyr Phe Gly Tyr Ser Thr Pro Trp Gly Tyr
65                  70                  75                  80

Phe Asp Phe Asn Arg Phe His Ser His Trp Ser Pro Arg Asp Trp Gln
                85                  90                  95

Arg Leu Ile Asn Asn Tyr Trp Gly Phe Arg Pro Arg Ser Leu Arg Val
            100                 105                 110

Lys Ile Phe Asn Ile Gln Val Lys Glu Val Thr Val Gln Asp Ser Thr
        115                 120                 125

Thr Thr Ile Ala Asn Asn Leu Thr Ser Thr Val Gln Val Phe Thr Asp
    130                 135                 140

Asp Asp Tyr Gln Leu Pro Tyr Val Val Gly Asn Gly Thr Glu Gly Cys
145                 150                 155                 160

Leu Pro Ala Phe Pro Pro Gln Val Phe Thr Leu Pro Gln Tyr Gly Tyr
                165                 170                 175

Ala Thr Leu Asn Arg Asp Asn Thr Glu Asn Pro Thr Glu Arg Ser Ser
            180                 185                 190

Phe Phe Cys Leu Glu Tyr Phe Pro Ser Lys Met Leu Arg Thr Gly Asn
        195                 200                 205

Asn Phe Glu Phe Thr Tyr Asn Phe Glu Glu Val Pro Phe His Ser Ser
    210                 215                 220

Phe Ala Pro Ser Gln Asn Leu Phe Lys Leu Ala Asn Pro Leu Val Asp
225                 230                 235                 240

Gln Tyr Leu Tyr Arg Phe Val Ser Thr Asn Asn Thr Gly Gly Val Gln
                245                 250                 255

Phe Asn Lys Asn Leu Ala Gly Arg Tyr Ala Asn Thr Tyr Lys Asn Trp
            260                 265                 270

Phe Pro Gly Pro Met Gly Arg Thr Gln Gly Trp Asn Leu Gly Ser Gly
        275                 280                 285

Val Asn Arg Ala Ser Val Ser Ala Phe Ala Thr Thr Asn Arg Met Glu

-continued

```
            290               295               300
Leu Glu Gly Ala Ser Tyr Gln Val Pro Pro Gln Pro Asn Gly Met Thr
305                 310               315               320

Asn Asn Leu Gln Gly Ser Asn Thr Tyr Ala Leu Glu Asn Thr Met Ile
                325               330               335

Phe Asn Ser Gln Pro Ala Asn Pro Gly Thr Thr Ala Thr Tyr Leu Glu
                340               345               350

Gly Asn Met Leu Ile Thr Ser Glu Ser Glu Thr Gln Pro Val Asn Arg
            355               360               365

Val Ala Tyr Asn Val Gly Gly Gln Met Ala Thr Asn Asn Gln Ser Ser
        370               375               380

Thr Thr Ala Pro Ala Thr Gly Thr Tyr Asn Leu Gln Glu Ile Val Pro
385                 390               395               400

Gly Ser Val Trp Met Glu Arg Asp Val Tyr Leu Gln Gly Pro Ile Trp
                405               410               415

Ala Lys Ile Pro Glu Thr Gly Ala His Phe His Pro Ser Pro Ala Met
                420               425               430

Gly Gly Phe Gly Leu Lys His Pro Pro Pro Met Met Leu Ile Lys Asn
            435               440               445

Thr Pro Val Pro Gly Asn Ile Thr Ser Phe Ala Asp Val Pro Val Ser
        450               455               460

Ser Phe Ile Thr Gln Tyr Ser Thr Gly Gln Val Thr Val Glu Met Glu
465                 470               475               480

Trp Glu Leu Lys Lys Glu Asn Ser Lys Arg Trp Asn Pro Glu Ile Gln
                485               490               495

Tyr Thr Asn Asn Tyr Asn Asp Pro Gln Phe Val Asp Phe Ala Pro Asp
                500               505               510

Ser Thr Gly Glu Tyr Arg Ser Thr Arg Pro Ile Gly Thr Arg Tyr Leu
            515               520               525

Thr Arg Pro Leu
    530
```

```
<210> SEQ ID NO 14
<211> LENGTH: 2175
<212> TYPE: DNA
<213> ORGANISM: Artificial sequence
<220> FEATURE:
<223> OTHER INFORMATION: The isolated nucleic acid encoding
      aforementioned VP1 of the capsid of the wild-type adeno-associated
      virus serotype 5 (AAV5)

<400> SEQUENCE: 14
atgtcttttg ttgatcaccc tccagattgg ttggaagaag ttggtgaagg tcttcgcgag      60
tttttgggcc ttgaagcggg cccaccgaaa ccaaaaccca atcagcagca tcaagatcaa     120
gcccgtggtc ttgtgctgcc tggttataac tatctcggac ccggaaacgg tctcgatcga     180
ggagagcctg tcaacagggc agacgaggtc gcgcgagagc acgacatctc gtacaacgag     240
cagcttgagg cgggagacaa ccectacctc aagtacaacc acgcggacgc cgagtttcag     300
gagaagctcg ccgacgacac atccttcggg ggaaacctcg gaaaggcagt ctttcaggcc     360
aagaaaaggg ttctcgaacc ttttggcctg gttgaagagg gtgctaagac ggcccctacc     420
ggaaagcgga tagacgacca ctttccaaaa agaaagaagg ctcggaccga gaggactcc      480 aagccttcca cctcgtcaga cgccgaagct ggacccagcg gatcccagca gctgcaaatc     540
ccagcccaac cagcctcaag tttgggagct gatacaatgt ctgcgggagg tggcggccca     600
```

-continued

```
ttgggcgaca ataaccaagg tgccgatgga gtgggcaatg cctcgggaga ttggcattgc    660
gattccacgt ggatggggga cagagtcgtc accaagtcca cccgaacctg ggtgctgccc    720
agctacaaca accaccagta ccgagagatc aaaagcggct ccgtcgacgg aagcaacgcc    780
aacgcctact ttggatacag caccccctgg gggtactttg actttaaccg cttccacagc    840
cactggagcc cccgagactg gcaaagactc atcaacaact actggggctt cagacccngg    900
tccctcagag tcaaaatctt caacattcaa gtcaaagagg tcacggtgca ggactccacc    960
accaccatcg ccaacaacct cacctccacc gtccaagtgt ttacggacga cgactaccag   1020 ctgcccctacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca agatgctgag aacgggcaac   1200
aactttgagt ttacctacaa ctttgaggag gtgcccttcc actccagctt cgctcccagt   1260
cagaacctct tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg ctggaacct gggctccggg   1440 gtcaaccgcg ccagtgtcag cgccttcgcc acgaccaata ggatggagct cgagggcgcg   1500
agttaccagg tgcccccgca gccgaacggc atgaccaaca acctccaggg cagcaacacc   1560
tatgccctgg agaacactat gatcttcaac agccagccgg cgaaccccgg caccaccgcc   1620
acgtacctcg agggcaacat gctcatcacc agcgagagcg agacgcagcc ggtgaaccgc   1680
gtggcgtaca acgtcggcgg gcagatggcc accaacaacc agagctccac cactgccccc   1740
gcgaccggca cgtacaacct ccaggaaatc gtgcccggca gcgtgtggat ggagagggac   1800
gtgtacctcc aaggacccat ctgggccaag atcccagaga cggggcgca ctttcacccc   1860 tctccggcca tgggcggatt cggactcaaa cacccaccgc ccatgatgct catcaagaac   1920
acgcctgtgc ccggaaatat caccagcttc tcggacgtgc ccgtcagcag cttcatcacc   1980
cagtacagca ccgggcaggt caccgtggag atggagtggg agctcaagaa ggaaaactcc   2040
aagaggtgga acccagagat ccagtacaca aacaactaca cgaccccca gtttgtggac   2100 tttgccccgg acagcaccgg ggaatacaga accaccagac ctatcggaac ccgatacctt   2160
acccgacccc tttaa                                                   2175
```

```
<210> SEQ ID NO 15
<211> LENGTH: 1767
<212> TYPE: DNA
<213> ORGANISM: Artificial sequence
<220> FEATURE:
<223> OTHER INFORMATION: The isolated nucleic acid encoding altered VP2
      protein of the adeno-associated virus serotype 5 (AAV5) capsid
      with amino acid T575S substitution

<400> SEQUENCE: 15
```

```
acggcccta ccggaaagcg gatagacgac cactttccaa aaagaaagaa ggctcggacc     60
gaagaggact ccaagccttc cacctcgtca gacgccgaag ctggacccag cggatcccag    120
cagctgcaaa tcccagccca accagcctca agtttgggag ctgatacaat gtctgcggga    180
ggtggcggcc cattgggcga caataaccaa ggtgccgatg gagtgggcaa tgcctcggga    240
gattggcatt gcgattccac gtggatgggg gacagagtcg tcaccaagtc caccgaacc     300 tgggtgctgc cagctacaa caaccaccag taccgagaga tcaaaagcgg ctccgtcgac     360
ggaagcaacg ccaacgccta cttggatac agcacccct gggggtactt tgactttaac     420
```

-continued

```
cgcttccaca gccactggag cccccgagac tggcaaagac tcatcaacaa ctactggggc        480
ttcagacccc ggtccctcag agtcaaaatc ttcaacattc aagtcaaaga ggtcacggtg        540
caggactcca ccaccaccat cgccaacaac ctcacctcca ccgtccaagt gtttacggac        600
gacgactacc agctgcccta cgtcgtcggc aacgggaccg agggatgcct gccggccttc        660
cctccgcagg tctttacgct gccgcagtac ggttacgcga cgctgaaccg cgacaacaca        720
gaaaatccca ccgagaggag cagcttcttc tgcctagagt actttcccag caagatgctg        780
agaacgggca caactttga gtttacctac aactttgagg aggtgccctt ccactccagc        840
ttcgctccca gtcagaacct cttcaagctg gccaacccgc tggtggacca gtacttgtac        900
cgcttcgtga gcacaaataa cactggcgga gtccagttca caagaacct ggccgggaga        960 tacgccaaca cctacaaaaa ctggttcccg gggcccatgg gccgaaccca gggctggaac       1020
ctgggctccg gggtcaaccg cgccagtgtc agcgccttcg ccacgaccaa taggatggag       1080
ctcgagggcg cgagttacca ggtgccccg cagccgaacg gcatgaccaa caacctccag       1140
ggcagcaaca cctatgccct ggagaacact atgatcttca cagccagcc ggcgaacccg       1200 ggcaccaccg ccacgtacct cgagggcaac atgctcatca ccagcgagag cgagacgcag       1260
ccggtgaacc gcgtggcgta caacgtcggc gggcagatgg ccaccaacaa ccagagctcc       1320
accactgccc ccgcgaccgg cacgtacaac ctccaggaaa tcgtgcccgg cagcgtgtgg       1380
atggagaggg acgtgtacct ccaaggaccc atctgggcca agatcccaga gacggggggcg       1440 cactttcacc cctctccggc catgggcgga ttcggactca aacacccacc gcccatgatg       1500
ctcatcaaga acacgcctgt gcccggaaat atcaccagct tctcggacgt gcccgtcagc       1560
agcttcatca cccagtacag caccgggcag gtcaccgtgg agatggagtg ggagctcaag       1620
aaggaaaact ccaagaggtg gaacccagag atccagtaca caaacaacta caacgacccc       1680
cagtttgtgg actttgcccc ggacagcacc ggggaataca gaagcaccag acctatcgga       1740
acccgatacc ttacccgacc cctttaa                                         1767
```

```
<210> SEQ ID NO 16
<211> LENGTH: 1767
<212> TYPE: DNA
<213> ORGANISM: Artificial sequence
<220> FEATURE:
<223> OTHER INFORMATION: The isolated nucleic acid encoding altered
      aforementioned VP2 of the adeno-associated virus serotype 5 (AAV5)
      capsid of the wild-type

<400> SEQUENCE: 16
```

```
acggccccta ccggaaagcg gatagacgac cactttccaa aaagaaagaa ggctcggacc         60
gaagaggact ccaagccttc cacctcgtca gacgccgaag ctggaccag cggatcccag        120 cagctgcaaa tcccagccca accagcctca agtttgggag ctgatacaat gtctgcggga        180
ggtggcggcc cattgggcga caataaccaa ggtgccgatg gagtgggcaa tgcctcggga        240
gattggcatt gcgattccac gtggatgggg gacagagtcg tcaccaagtc caccgaacc        300 tgggtgctgc ccagctacaa caaccaccag taccgagaga tcaaaagcgg ctccgtcgac        360
ggaagcaacg ccaacgccta ctttggatac agcacccct gggggtactt tgactttaac        420
cgcttccaca gccactggag cccccgagac tggcaaagac tcatcaacaa ctactggggc        480
ttcagacccc ggtccctcag agtcaaaatc ttcaacattc aagtcaaaga ggtcacggtg        540
caggactcca ccaccaccat cgccaacaac ctcacctcca ccgtccaagt gtttacggac        600
```

-continued

```
gacgactacc agctgcccta cgtcgtcggc aacgggaccg agggatgcct gccggccttc     660
cctccgcagg tctttacgct gccgcagtac ggttacgcga cgctgaaccg cgacaacaca     720
gaaaatccca ccgagaggag cagcttcttc tgcctagagt actttcccag caagatgctg     780
agaacgggca acaactttga gtttacctac aactttgagg aggtgccctt ccactccagc     840
ttcgctccca gtcagaacct cttcaagctg gccaacccgc tggtggacca gtacttgtac     900
cgcttcgtga gcacaaataa cactggcgga gtccagttca acaagaacct ggccgggaga     960
tacgccaaca cctacaaaaa ctggttcccg gggcccatgg gccgaaccca gggctggaac    1020
ctgggctccg gggtcaaccg cgccagtgtc agcgccttcg ccacgaccaa taggatggag    1080
ctcgagggcg cgagttacca ggtgcccccg cagccgaacg gcatgaccaa caacctccag    1140
ggcagcaaca cctatgccct ggagaacact atgatcttca cagccagcc ggcgaacccg    1200 ggcaccaccg ccacgtacct cgagggcaac atgctcatca ccagcgagag cgagacgcag    1260
ccggtgaacc gcgtggcgta caacgtcggc gggcagatgg ccaccaacaa ccagagctcc    1320
accactgccc ccgcgaccgg cacgtacaac ctccaggaaa tcgtgcccgg cagcgtgtgg    1380
atggagaggg acgtgtacct ccaaggaccc atctgggcca agatcccaga cacgggggcg    1440
cactttcacc cctctccggc catgggcgga ttcggactca aacacccacc gcccatgatg    1500
ctcatcaaga acacgcctgt gcccggaaat atcaccagct ctcggacgt gcccgtcagc    1560 agcttcatca cccagtacag caccgggcag gtcaccgtgg agatggagtg ggagctcaag    1620
aaggaaaact ccaagaggtg gaacccagag atccagtaca caaacaacta caacgacccc    1680
cagtttgtgg actttgcccc ggacagcacc ggggaataca gaaccaccag acctatcgga    1740
acccgatacc ttacccgacc cctttaa                                        1767
```

```
<210> SEQ ID NO 17
<211> LENGTH: 1599
<212> TYPE: DNA
<213> ORGANISM: Artificial sequence
<220> FEATURE:
<223> OTHER INFORMATION: The isolated nucleic acid encoding altered VP3
      protein of the adeno-associated virus serotype 5 (AAV5) capsid
      with amino acid T519S substitution

<400> SEQUENCE: 17
atgtctgcgg gaggtggcgg cccattgggc gacaataacc aaggtgccga tggagtgggc      60
aatgcctcgg gagattggca ttgcgattcc acgtggatgg gggacagagt cgtcaccaag     120
tccacccgaa cctgggtgct gcccagctac aacaaccacc agtaccgaga gatcaaaagc     180
ggctccgtcg acggaagcaa cgccaacgcc tactttggat acagcacccc ctgggggtac     240
tttgacttta accgcttcca cagccactgg agccccgag actggcaaag actcatcaac     300
aactactggg gcttcagacc ccggtccctc agagtcaaaa tcttcaacat tcaagtcaaa     360
gaggtcacgg tgcaggactc caccaccacc atcgccaaca acctcacctc caccgtccaa     420
gtgtttacgg acgacgacta ccagctgccc tacgtcgtcg caacgggac cgagggatgc     480 ctgccggcct ccctccgca ggtctttacg ctgccgcagt acggttacgc gacgctgaac     540
cgcgacaaca cagaaaatcc caccgagagg agcagcttct tctgcctaga gtactttccc     600
agcaagatgc tgagaacggg caacaacttt gagtttacct acaactttga ggaggtgccc     660
ttccactcca gcttcgctcc cagtcagaac ctcttcaagc tggccaaccc gctggtggac     720
cagtacttgt accgcttcgt gagcacaaat aacactggcg gagtccagtt caacaagaac     780
ctggccggga gatacgccaa cacctacaaa aactggttcc cggggcccat gggccgaacc     840
```

-continued

```
cagggctgga acctgggctc cggggtcaac cgcgccagtg tcagcgcctt cgccacgacc      900
aataggatgg agctcgaggg cgcgagttac caggtgcccc cgcagccgaa cggcatgacc      960
aacaacctcc agggcagcaa cacctatgcc ctggagaaca ctatgatctt caacagccag     1020
ccggcgaacc cgggcaccac cgccacgtac ctcgagggca catgctcat caccagcgag      1080 agcgagacgc agccggtgaa ccgcgtggcg tacaacgtcg gcgggcagat ggccaccaac     1140
aaccagagct ccaccactgc ccccgcgacc ggcacgtaca acctccagga aatcgtgccc     1200
ggcagcgtgt ggatggagag ggacgtgtac ctccaaggac ccatctgggc caagatccca     1260
gagacggggg cgcactttca cccctctccg gccatgggcg gattcggact caaacaccca     1320
ccgcccatga tgctcatcaa gaacacgcct gtgcccggaa atatcaccag cttctcggac     1380
gtgcccgtca gcagcttcat cacccagtac agcaccgggc aggtcaccgt ggagatggag     1440
tgggagctca gaaggaaaa ctccaagagg tggaacccag agatccagta cacaaacaac     1500
tacaacgacc cccagtttgt ggactttgcc ccggacagca ccgggaata cagaagcacc     1560 agacctatcg gaacccgata ccttacccga ccccttaa                            1599
```

```
<210> SEQ ID NO 18
<211> LENGTH: 1599
<212> TYPE: DNA
<213> ORGANISM: Artificial sequence
<220> FEATURE:
<223> OTHER INFORMATION: The isolated nucleic acid encoding altered
      aforementioned VP3 of the adeno-associated virus serotype 5 (AAV5)
      capsid of the wild-type

<400> SEQUENCE: 18
```

```
atgtctgcgg gaggtggcgg cccattgggc gacaataacc aaggtgccga tggagtgggc       60
aatgcctcgg gagattggca ttgcgattcc acgtggatgg gggacagagt cgtcaccaag      120
tccacccgaa cctgggtgct gcccagctac aacaaccacc agtaccgaga gatcaaaagc      180
ggctccgtcg acggaagcaa cgccaacgcc tactttggat acagcacccc ctggggggtac      240 tttgacttta accgcttcca cagccactgg agccccgag actggcaaag actcatcaac       300
aactactggg gcttcagacc ccggtccctc agagtcaaaa tcttcaacat tcaagtcaaa      360
gaggtcacgg tgcaggactc caccaccacc atcgccaaca acctcacctc caccgtccaa      420
gtgtttacgg acgacgacta ccagctgccc tacgtcgtcg caacgggac cgagggatgc      480 ctgccggcct ccctccgca ggtctttacg ctgccgcagt acggttacgc gacgctgaac      540
cgcgacaaca cagaaaatcc caccgagagg agcagcttct tctgcctaga gtactttccc      600
agcaagatgc tgagaacggg caacaacttt gagtttacct acaactttga ggaggtgccc      660
ttccactcca gcttcgctcc cagtcagaac ctcttcaagc tggccaaccc gctggtggac      720
cagtacttgt accgcttcgt gagcacaaat aacactggcg gagtccagtt caacaagaac      780
ctggccggga gatacgccaa cacctacaaa aactggttcc cggggcccat gggccgaacc      840
cagggctgga acctgggctc cggggtcaac cgcgccagtg tcagcgcctt cgccacgacc      900
aataggatgg agctcgaggg cgcgagttac caggtgcccc cgcagccgaa cggcatgacc      960
aacaacctcc agggcagcaa cacctatgcc ctggagaaca ctatgatctt caacagccag     1020
ccggcgaacc cgggcaccac cgccacgtac ctcgagggca catgctcat caccagcgag      1080 agcgagacgc agccggtgaa ccgcgtggcg tacaacgtcg gcgggcagat ggccaccaac     1140
aaccagagct ccaccactgc ccccgcgacc ggcacgtaca acctccagga aatcgtgccc     1200
```

-continued

```
ggcagcgtgt ggatggagag ggacgtgtac ctccaaggac ccatctgggc caagatccca   1260
gagacggggg cgcactttca cccctctccg gccatgggcg gattcggact caaacaccca   1320
ccgcccatga tgctcatcaa gaacacgcct gtgcccggaa atatcaccag cttctcggac   1380
gtgcccgtca gcagcttcat cacccagtac agcaccgggc aggtcaccgt ggagatggag   1440
tgggagctca agaaggaaaa ctccaagagg tggaacccag agatccagta cacaaacaac   1500
tacaacgacc cccagtttgt ggactttgcc ccggacagca ccggggaata cagaaccacc   1560
agacctatcg gaacccgata ccttacccga cccctttaa                          1599
```

ISOLATED MODIFIED VP1 CAPSID PROTEIN OF AAV5

REFERENCE TO A SEQUENCE LISTING SUBMITTED VIA EFS-WEB

The content of the ASCII text file of the sequence listing named "P2385US00-Sequence-listing-EN-ANB-002_EN_Sequence-ANSI_11-03-2022" which is 73.9 kb in size was created on Mar. 29, 2022 and electronically submitted herewith via EFS-Web is incorporated herein by reference.

FIELD OF INVENTION

This application relates to the fields of gene therapy and molecular biology. More specifically, the present invention relates to an isolated altered VP1 protein of adeno-associated virus serotype 5 (AAV5) capsid, which comprises one or more amino acid substitutions as compared to the VP1 protein of a wild-type AAV5 capsid, which improve transduction efficiency, as well as to a capsid and a vector based thereon.

BACKGROUND OF THE INVENTION

Adeno-associated virus (AAV) is a small (20 nm), independent replication-defective, nonenveloped virus. Many different AAV serotypes have been described in human and primates. The adeno-associated virus genome is composed of (+ or −) single-stranded DNA (ssDNA) being about 4,700 nucleotide long. The genomic DNA has terminal inverted repeats (ITRs) at the ends. The genome comprises two open reading frames (ORFs), Rep and Cap comprising several alternative reading frames encoding various protein products. The rep products are essential for AAV replication, whereas three capsid proteins (the VP1, VP2, and VP3), along with other alternative products, are encoded by the Cap gene. The VP1, VP2 and VP3 proteins are at 1:1:10 ratio to form an icosahedral capsid (Xie Q. et al. The atomic structure of adeno-associated virus (AAV-2), a vector for human gene therapy. Proc Natl Acad Sci USA, 2002; 99:10405-10410). During recombinant AAV (rAAV) vector production, an expression cassette flanked by ITRs is packaged into an AAV capsid. The genes required for AAV replication are not included in the cassette. Recombinant AAV is considered to be one of the safest and most widely used viral vectors for in vivo gene transfer. Vectors can infect cells of multiple tissue types to provide strong and sustained transgene expression. They are also non-pathogenic, and have a low immunogenicity profile (High KA et al., "rAAV human trial experience" Methods Mol Biol. 2011; 807:429-57).

One of the essential goals of trials in the field of development of effective gene therapy is to optimize the vector to maximize tissue transduction while minimizing vector dosage.

It is known that, the various AAV serotypes are characterized by affinity for distinct host cell surface receptors, toward which they have tropism. Thus, the primary known receptor for AAV2 is heparan sulfate proteoglycan, the coreceptors are integrin heterodimer aVβ5, fibroblast growth factor receptor type 1, and hepatocyte growth factor receptor, c-Met. AAV12 binds to heparan sulfate proteoglycans and sialic acid. AAV4 and AAV5 bind to N- and O-linked sialic acids, respectively. AAV5 activates the platelet-derived growth factor receptor. At the same time, a binding has been established between the amino acid sequence of AAV capsid proteins and the process of assembly thereof, encapsidation of the genome, affinity for different types of receptors represented on the surface of host cells (Govindasamy L. et. al. Structural insights into adeno-associated virus serotype 5. J Virol. 2013 October;87(20): 11187-99).

International application WO 2012145601 discloses adeno-associated virus (AAV) virions with variant capsid protein, wherein the AAV virions exhibit greater infectivity of a retinal cell, when administered via intravitreal injection, compared to a wild-type AAV.

International application WO 2013158879 discloses an adeno-associated virus (AAV) vector delivering to a subject a heterologous nucleic acid sequence, comprising a VP1 capsid protein, which comprises one or more lysine substitutions, wherein one lysine substitution is K137R, wherein said lysine substitution is effective to inhibit ubiquitination of said capsid protein, thereby increasing transduction of said AAV vector in a target cell.

There is currently a need for AAVs with improved transduction ability, which include in structure thereof various transgenes, including clinically important transgenes, for patients in need thereof. Improved tissue transduction enables to minimize the dose of vector being administered to a subject.

The inventors have surprisingly found that the presence of one or more amino acid substitutions in the VP1 protein of the wild-type AAV5 capsid, which are selected from the group comprising:

S651A,

S2A and T711S or

S2A, S651A, and T711S, caused an increase in the efficiency of transduction of target cells using the AAV serotype 5 vector with this/these modification(s) and a significant increase in the efficiency of transgene delivery by the rAAV vectors with the above mutations.

BRIEF DESCRIPTION OF INVENTION

In one aspect, the present invention relates to an isolated altered VP1 protein of adeno-associated virus serotype 5 (AAV5) capsid for highly-efficient transduction of target cells, comprising the amino acid sequence of the VP1 protein of the wild-type AAV5 capsid, which is encoded by the Cap gene, with one or more substitutions selected from the group comprising:

S651A,

S2A and T711S,

S2A, S651A, and T711S.

In some embodiments, the amino acid sequence of the VP1 protein of the wild-type AAV5 capsid has the amino acid sequence represented by SEQ ID NO: 1.

In some embodiments, the isolated altered VP1 protein of AAV5 capsid includes one substitution at S651A position.

In some embodiments, the isolated altered VP1 protein of AAV5 capsid has the amino acid sequence represented by SEQ ID NO: 2.

In some embodiments, the isolated altered VP1 protein of AAV5 capsid includes the S2A and T711S substitutions.

In some embodiments, the isolated altered VP1 protein of AAV5 capsid has the amino acid sequence represented by SEQ ID NO: 3.

In some embodiments, the isolated altered VP1 protein of AAV5 capsid includes the S2A, S651A, and T711S substitutions.

In some embodiments, the isolated altered VP1 protein of AAV5 capsid has the amino acid sequence represented by SEQ ID NO: 4.

In one aspect, the present invention relates to an isolated nucleic acid encoding the above altered VP1 protein of adeno-associated virus serotype 5 (AAV5) capsid, which is used for highly-efficient transduction of target cells.

In some embodiments, the isolated nucleic acid encoding the altered VP1 protein of adeno-associated virus serotype 5 (AAV5) capsid with the amino acid S651A substitution is represented by the nucleic acid sequence with SEQ ID NO: 5 or any other sequence encoding the corresponding amino acid sequence of the altered protein of adeno-associated virus serotype 5 (AAV5) capsid with the amino acid S651A substitution.

In some embodiments, the isolated nucleic acid encoding the altered VP1 protein of adeno-associated virus serotype 5 (AAV5) capsid with the amino acid S2A and T711S substitutions is represented by the nucleic acid sequence with SEQ ID NO: 6 or any other sequence encoding the corresponding amino acid sequence of the altered protein of adeno-associated virus serotype 5 (AAV5) capsid with the amino acid S2A and T711S substitutions.

In some embodiments, the isolated nucleic acid encoding the altered VP1 protein of adeno-associated virus serotype 5 (AAV5) capsid with the amino acid S2A, S651A, and T711S substitutions is represented by the nucleic acid sequence with SEQ ID NO: 7 or any other sequence encoding the corresponding amino acid sequence of the altered protein of adeno-associated virus serotype 5 (AAV5) capsid with the amino acid S2A, S651A, and T711S substitutions.

In one aspect, the present invention relates to an isolated capsid for highly-efficient transduction of target cells, which includes the above altered VP1 protein of adeno-associated virus serotype 5 (AAV5) capsid.

In some embodiments, the isolated capsid includes the above altered VP1 protein of adeno-associated virus serotype 5 (AAV5) capsid, a VP2 protein of AAV5 capsid or an altered variant thereof, and a VP3 protein of AAV5 capsid or an altered variant thereof.

In some embodiments, the isolated capsid includes a VP2 protein of the wild-type AAV5 capsid.

In some embodiments, the isolated capsid includes a VP1 protein of the wild-type AAV5 capsid, which has the amino acid sequence represented by SEQ ID NO: 8.

In some embodiments, the isolated capsid includes an altered VP2 protein of adeno-associated virus serotype 5 (AAV5) capsid.

In some embodiments, the isolated capsid includes an altered VP2 protein of AAV5 capsid, which comprises the T575S substitution.

In some embodiments, the isolated capsid includes an altered VP2 protein of AAV5 capsid, which comprises the T575S substitution, and has the amino acid sequence represented by SEQ ID NO: 9.

In some embodiments, the isolated capsid includes an altered VP2 protein of AAV5 capsid, which comprises the S515A and T575S substitutions.

In some embodiments, the isolated capsid includes an altered VP2 protein of AAV5 capsid, which comprises the S515A and T575S substitutions, and has the amino acid sequence represented by SEQ ID NO: 10.

In some embodiments, the isolated capsid includes a VP3 protein of the wild-type AAV5 capsid.

In some embodiments, the isolated capsid includes the VP3 protein of the wild-type AAV5 capsid, which has the amino acid sequence represented by SEQ ID NO: 11.

In some embodiments, the isolated capsid includes an altered VP3 protein of adeno-associated virus serotype 5 (AAV5) capsid.

In some embodiments, the isolated capsid includes the altered VP3 protein of AAV5 capsid, which comprises the T519S substitution.

In some embodiments, the isolated capsid includes the altered VP3 protein of AAV5 capsid, which comprises the T519S substitution, and has the amino acid sequence represented by SEQ ID NO: 12.

In some embodiments, the isolated capsid includes the altered VP3 protein of AAV5 capsid, which comprises the S459A and T519S substitutions.

In some embodiments, the isolated capsid includes the altered VP3 protein of AAV5 capsid, which comprises the S459A and T519S substitutions, and has the amino acid sequence represented by SEQ ID NO: 13.

In one aspect, the present invention relates to an isolated nucleic acid encoding the above capsid, which is used for highly-efficient transduction of target cells.

In one aspect, the present invention relates to a vector based on recombinant adeno-associated virus serotype 5 (rAAV5) for delivery to a subject of a heterologous nucleic acid sequence, which includes:

1) the above capsid, and
2) a heterologous nucleic acid sequence comprising regulatory sequences that promote the expression of a product encoded by the heterologous nucleic acid sequence, in target cells.

In some embodiments, the vector based on rAAV5 comprises a heterologous nucleic acid sequence encoding a product that is a therapeutic polypeptide or a reporter polypeptide.

In some embodiments, the vector based on rAAV5 comprises a heterologous nucleic acid sequence encoding a product that is a therapeutic polypeptide, wherein the therapeutic polypeptide is a coagulation factor selected from the group consisting of Factor VIII, Factor IX, or a functional variant thereof.

In some embodiments, the vector based on rAAV5 comprises a heterologous nucleic acid sequence encoding a product that is Factor VIII or a functional variant thereof.

In some embodiments, the vector based on rAAV5 comprises a heterologous nucleic acid sequence encoding a product that is Factor IX or a functional variant thereof.

In one aspect, the present invention relates to a pharmaceutical composition for the delivery of a gene product to a subject in need thereof, which comprises:

a) the above vector based on rAAV5; and
b) a pharmaceutically acceptable excipient.

In some embodiments, the pharmaceutical composition is used for the delivery of a gene product to a human in need thereof.

In one aspect, the present invention relates to a method for the delivery of a gene product to a subject in need thereof, which comprises administering to the subject the above vector based on rAAV5 or the above pharmaceutical composition.

In some embodiments, the method for the delivery of a gene product is used for the delivery of a gene product to a human in need thereof.

In one aspect, the present invention relates to the use of the above vector based on rAAV5 or the above pharmaceutical composition for the treatment of a disease in a subject in need thereof.

In some embodiments, the use is used for the treatment of a disease in a human in need thereof.

In some embodiments of the use, the disease is selected from the group comprising: blood diseases; central nervous system diseases; metabolic diseases; muscle diseases; hereditary diseases.

In some embodiments of the use, the disease is a blood disease.

In some embodiments of the use, the expression product of the heterologous nucleic acid sequence is Factor IX or a functional variant thereof.

In some embodiments of the use, the expression product of the heterologous nucleic acid sequence is Factor VIII or a functional variant thereof.

In some embodiments of the use, the disease is a muscle disease.

In some embodiments of the use, the disease is a hereditary disease.

In one aspect, the present invention relates to a method for the production of the above the vector based on rAAV5, which comprises the transfection of producer cells with the above nucleic acid encoding the above capsid.

AmpR is a beta-lactamase gene that provides resistance to ampicillin, pUC origin is a pUC replication origin in bacteria, ITR is inverted terminal repeats, CMV-Promoter is the promoter of cytomegalovirus early genes, Poly A is a polyadenylation signal sequence, for increasing mRNA stability, HBG Intron is human beta globine intron, GFP is a green fluorescent protein gene, T2A is a 2A self-cleaving peptide that allows co-expression of a target protein and reporter protein.

Figure 2:
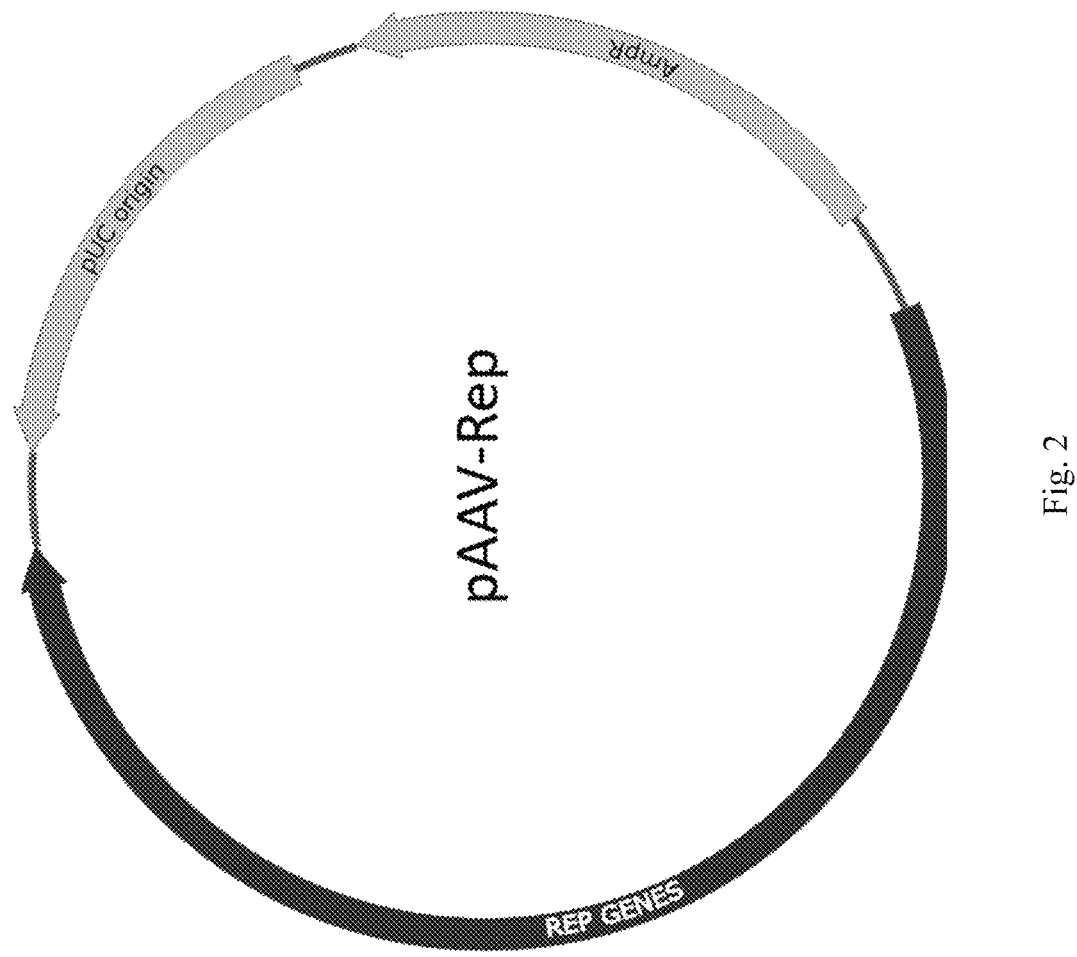

FIG. 2. Circular scheme of plasmid pAAV-Rep intended for producing recombinant viral products of wild-type AAV serotype 5 from the library of random variants.

AmpR is a beta-lactamase gene that provides resistance to ampicillin, pUC origin is a pUC replication origin in bacteria, Rep genes is a Rep gene sequence encoding AAV replication proteins.

Figure 3:
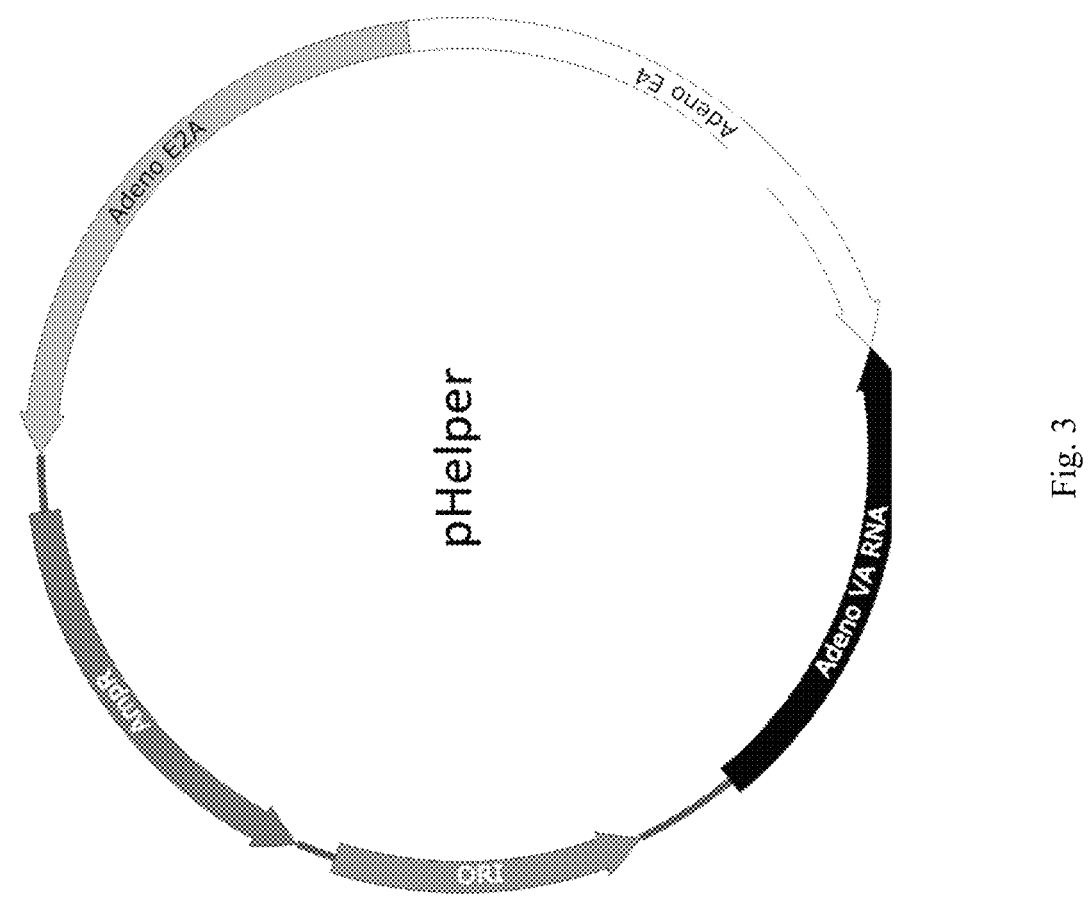

FIG. 3. Circular scheme of plasmid pHelper intended for producing recombinant viral products of wild-type AAV serotype 5 from the library of random variants.

AmpR is a beta-lactamase gene that provides resistance to ampicillin,

Ori is a replication origin in bacteria,

Adeno E2A is a helper adenovirus gene sequence involved in viral DNA replication, Adeno E4 is a helper adenovirus gene sequence involved in viral DNA replication, Adeno VARNA is a helper adenovirus gene sequence responsible for the translation of both early and late viral genes.

Figure 4:
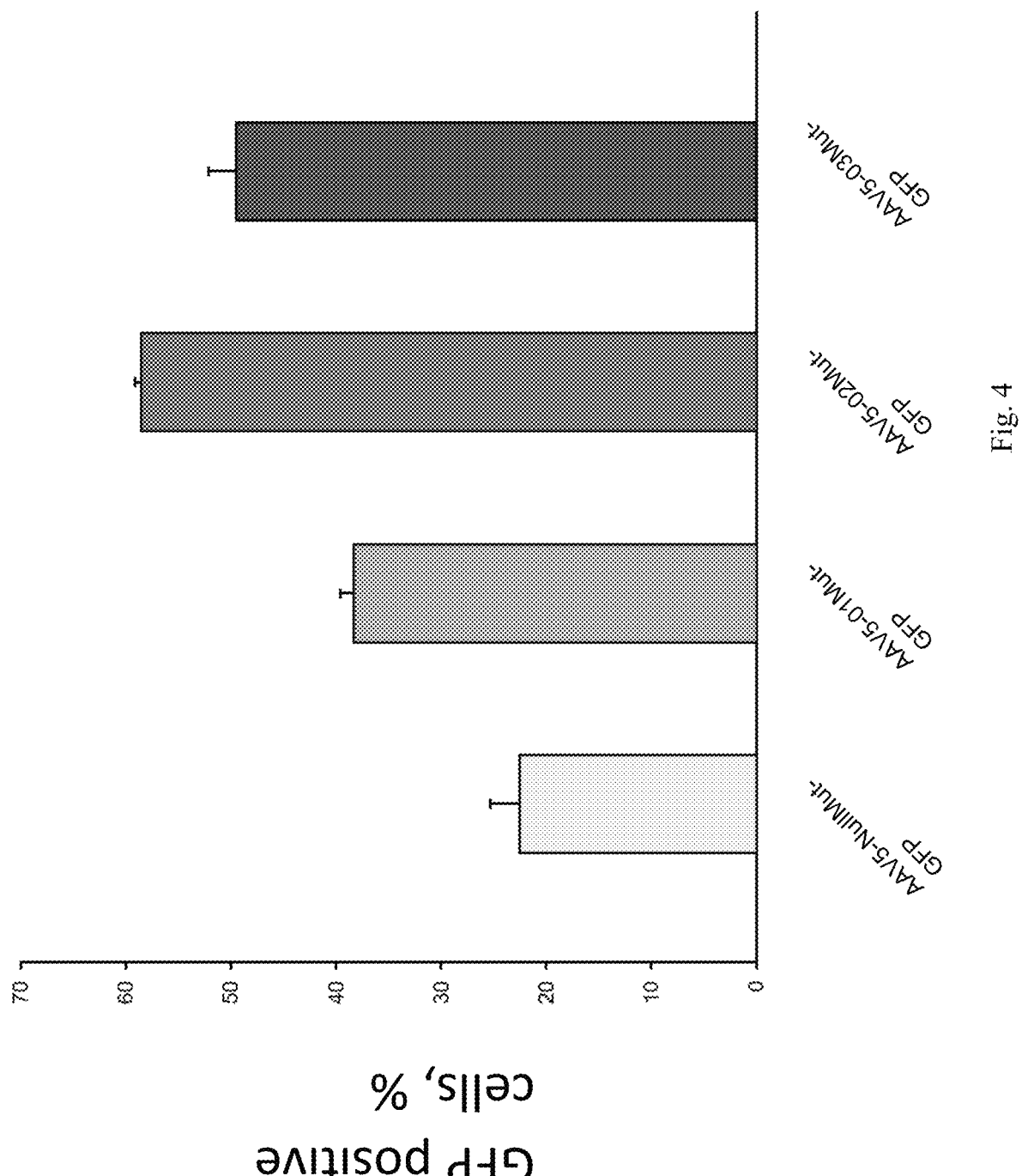

FIG. 4. Analysis of efficiency of CHO-K1-S cell transduction with AAV5-GFP-based viral products, wherein VP1 protein of the wild-type AAV5 capsid includes one or more amino acid substitutions.

Figure 5:
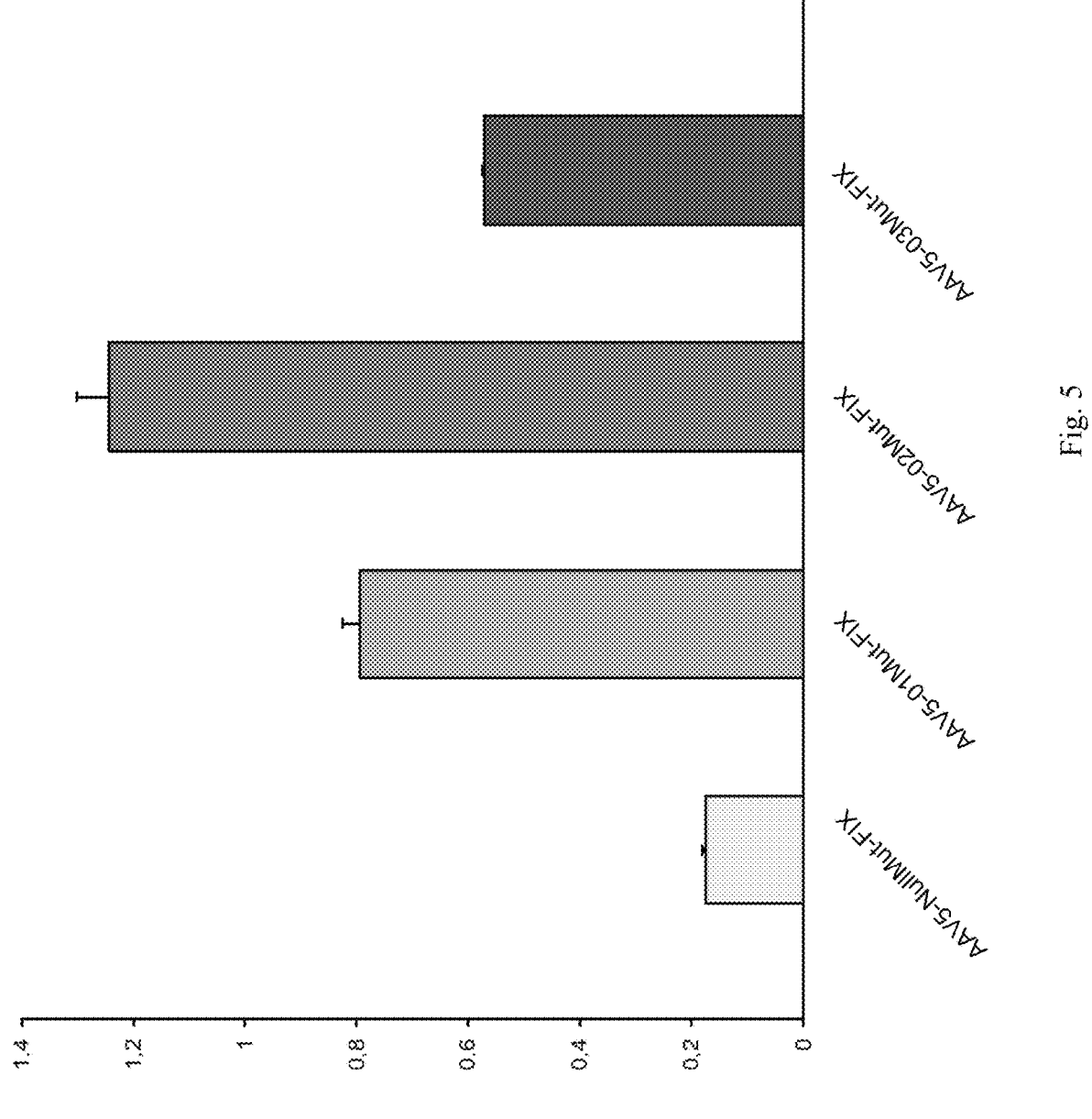

FIG. 5. Analysis of concentration of hFIX protein in the medium harvested from the CHO-K1-S cells 7 days post transduction with the AAV5-hFIX-based viral products, wherein VP1 protein of the wild-type AAV5 capsid includes one or more amino acid substitutions.

Figure 6:
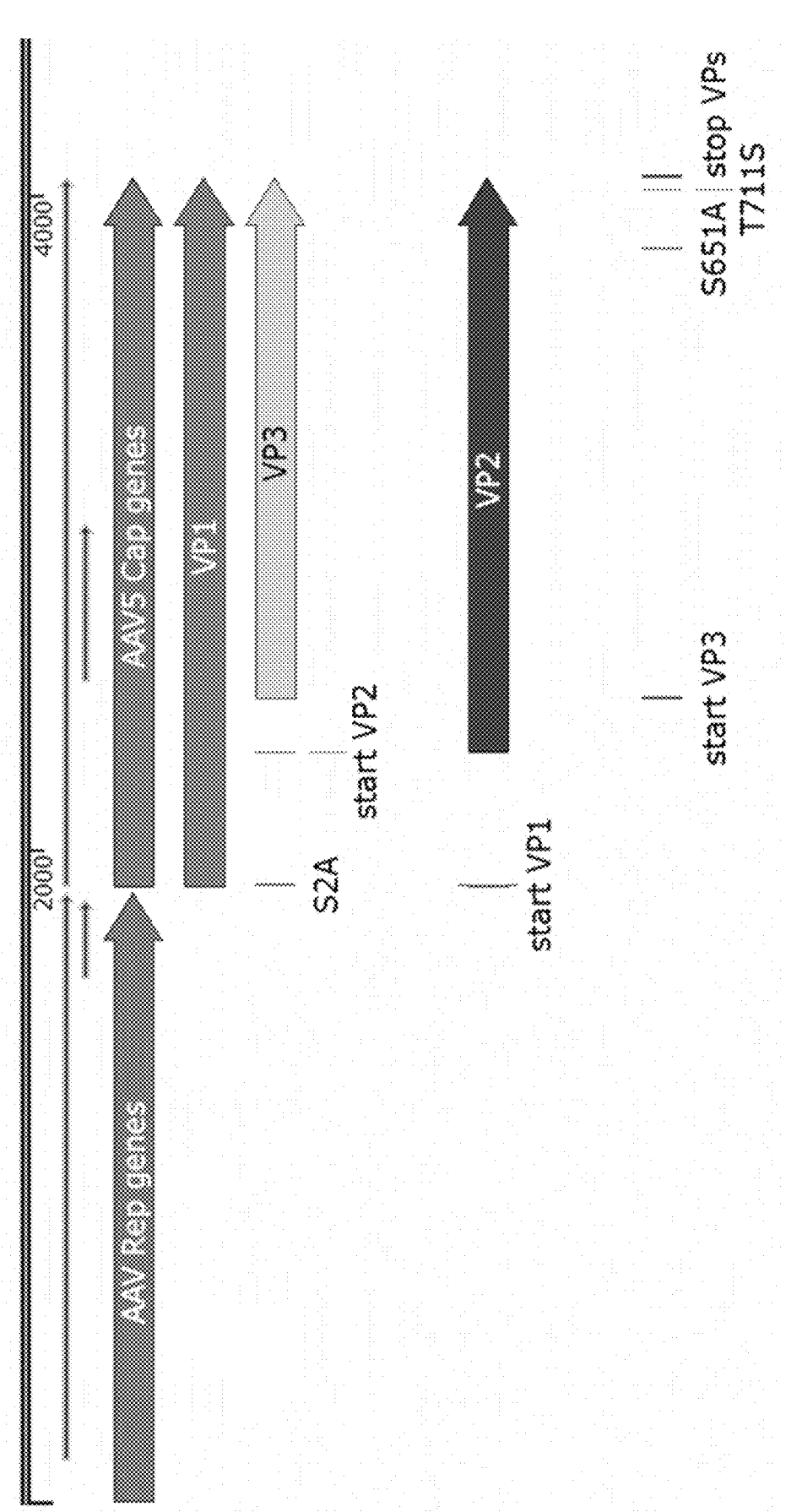

FIG. 6. Position of AAV5 capsid proteins in the genome.

2087-4258 bp— VP1
2495-4258 bp— VP2
2663-4258 bp— VP3

DESCRIPTION OF INVENTION

Definitions and General Methods

Unless defined otherwise, all technical and scientific terms used herein have the same meaning as is commonly understood by one of ordinary skill in the art.

Further, unless otherwise required by context, singular terms shall include pluralities and plural terms shall include the singular. Typically, the classification and methods of cell culture, molecular biology, immunology, microbiology, genetics, analytical chemistry, organic synthesis chemistry, medical and pharmaceutical chemistry, as well as hybridization and chemistry of protein and nucleic acids described herein are well known and widely used by those skilled in the art. Enzyme reactions and purification methods are performed according to the manufacturer's guidelines, as is common in the art, or as described herein.

"Isolated" means altered or removed from the natural state. For example, a nucleic acid or a peptide naturally present in an animal is not "isolated", but the same nucleic acid or peptide partially or completely separated from the coexisting materials of its natural state is "isolated". An isolated nucleic acid or protein can exist in substantially purified form, or can exist in a non-native environment such as, for example, a genetically modified cell.

The terms "naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

The term "genome" refers to the complete genetic material of an organism.

As used in the present description and claims that follow, unless otherwise dictated by the context, the words "include" and "comprise," or variations thereof such as "having," "includes", "including", "comprises," or "comprising," will be understood to imply the inclusion of a stated integer or group of integers but not the exclusion of any other integer or group of integers.

Protein (Peptide)

As used in the present description, the terms "peptide", "polypeptide" and "protein" are used interchangeably, and they refer to a compound consisting of amino acid residues that are covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used in the present description, the term refers to both short chains, which also commonly are referred to in the art, for example, as peptides, oligopeptides and oligomers, and to longer chains, which generally are referred to in the art as proteins, of which there are many types. "Polypeptides" include, inter alia, for example, biologically active fragments, substantially homologous polypeptides, oligopeptides, homodimers, heterodimers, variants of polypeptides, modified polypeptides, derivatives, analogs, fusion proteins. The polypeptides include natural peptides, recombinant peptides, synthetic peptides, or a combination thereof.

The terms "transformation," "transfection," and "transduction" refer to any method or means by which a nucleic acid is introduced into a cell or host organism, and may be used interchangeably to convey the same meaning. Such methods include, but are not limited to, transfection, electroporation, microinjection, infection, PEG-fusion, and the like.

Nucleic Acid Molecules

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, determining a fragment or a region of a nucleic acid, containing unnatural nucleotides or not, and being either a double-stranded DNA or RNA, a single-stranded DNA or RNA, or transcription products of said DNAs.

One skilled in the art has the general knowledge that nucleic acids are polynucleotides that can be hydrolyzed to monomeric "nucleotides". Monomeric nucleotides can be hydrolyzed into nucleosides. As used in the present description, polynucleotides include, as non-limiting examples, all nucleic acid sequences which are obtained by any means available in the art, including, as non-limiting examples, recombinant means, i.e. the cloning of nucleic acid sequences from a recombinant library or a cell genome, using ordinary cloning technology and PCR and the like, and by synthetic means.

It should also be noted here that the present invention does not relate to nucleotide sequences in their natural chromosomal environment, i.e. in a natural state. The sequences of the present invention have been isolated and/or purified, i.e. they were sampled directly or indirectly, for example by a copy, their environment having been at least partially modified. Thus, isolated nucleic acids obtained by recombinant genetics, by means, for example, of host cells, or obtained by chemical synthesis should also be mentioned here.

An "isolated" nucleic acid molecule is one which is identified and separated from at least one nucleic acid molecule-impurity, which the former is typically bound to in the natural source of nuclease nucleic acid. An isolated nucleic acid molecule is different from the form or set in which it is found under natural conditions. Thus, an isolated nucleic acid molecule is different from a nucleic acid molecule that exists in cells under natural conditions. An isolated nucleic acid molecule however includes a nucleic acid molecule located in cells in which the nuclease is normally expressed, for example, if the nucleic acid molecule has a chromosomal localization that is different from its localization in cells under natural conditions.

Unless otherwise indicated, the term nucleotide sequence encompasses its complement. Thus, a nucleic acid having a particular sequence should be understood as one which encompasses the complementary strand thereof with complementary sequence thereof.

Adeno-Associated Virus (AAV)

Viruses of the Parvoviridae family are small DNA-containing animal viruses. The Parvoviridae family may be divided into two subfamilies: the Parvovirinae, which members infect vertebrates, and the Densovirinae, which members infect insects. By 2006, there have been 11 serotypes of adeno-associated virus described (Mori, S. ET AL., 2004, "Two novel adeno-associated viruses from cynomolgus monkey: pseudotyping characterization of capsid protein", Virology, T. 330 (2): 375-83). All of the known serotypes can infect cells from multiple tissue types. Tissue specificity is determined by the capsid protein serotype; therefore, the adeno-associated virus-based vectors are constructed by assigning the desired serotype. Further information on parvoviruses and other members of the Parvoviridae is described in the literature (Kenneth I. Berns, "Parvoviridae: The Viruses and Their Replication", Chapter 69 in Fields Virology (3d Ed. 1996)).

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences of replication of non-structural proteins (Rep) and structural proteins (Cap). The Cap gene encodes the VP proteins (the VP1, VP2, and VP3) which form the capsid. The terminal 145 nucleotides are self-complementary and are organized such that an energetically stable intramolecular duplex forming a T-shaped hairpin may be formed. Such hairpin structures function as an origin for virus DNA replication, serving as primers for the cellular DNA polymerase complex. Following wild-type AAV (wtAAV) infection in mammalian cells, the Rep genes (e.g. Rep78 and Rep52) are expressed using the P5 promoter and the P19 promoter, respectively, and the both Rep proteins have a certain function in the replication of the viral genome. A splicing event in the Rep open reading frame (Rep ORF) results in the expression of actually four Rep proteins (e.g. Rep78, Rep68, Rep52, and Rep40). However, it has been shown that the unspliced mRNA encoding Rep78 and Rep52 proteins is sufficient for AAV vector production in mammalian cells.

Recombinant Adeno-Associated Virus (rAAV)-Based Vector

The term "vector" as used herein means a nucleic acid molecule capable of transporting another nucleic acid to which it has been linked.

The term "recombinant AAV vector" (or "rAAV vector") as used in the present description refers to a vector comprising one or more polynucleotide sequences of interest, genes of interest or "transgenes" that are flanked by parvoviral or inverted terminal repeat sequences (ITRs)

The terms "infection unit (iu)," "infectious particle," or "replication unit," as used in reference to a viral titer, refer to the number of infectious recombinant AAV vector particles as measured by the infectious center assay, also known as replication center assay, as described, for example, in McLaughlin et al., J. Virol. (1988) 62:1963-1973.

The term "heterologous" as it relates to nucleic acid sequences such as coding sequences and regulatory sequences, denotes sequences that are not normally joined together, and/or are not normally associated with a particular cell. Thus, a "heterologous" region of a nucleic acid construct or a vector is a fragment of nucleic acid within or attached to another nucleic acid molecule that is not found in association with the other molecule in nature. For example, a heterologous region of a nucleic acid construct may include a coding sequence flanked by sequences not found in association with the coding sequence in nature. Another example of a heterologous coding sequence is a construct where the coding sequence itself is not found in nature (e.g. synthetic sequences having codons different from the native gene).

As used herein, the term "operably linked" refers to a linkage of polynucleotide (or polypeptide) elements in a functional relationship. A nucleic acid is "operably linked" when it is present in functional relationship conditions with another nucleic acid sequence. For example, a transcription regulatory sequence is operably linked to a coding sequence if it affects the transcription of said coding sequence. The term "operably linked" means that the DNA sequences being linked are typically contiguous and, where it is necessary to join two protein coding regions, are also contiguous and are present in the reading frame.

As used in the present description, the term "promoter" or "transcription regulatory sequence" or "regulatory sequence" refers to a nucleic acid fragment that controls the transcription of one or more coding sequences, and that is located upstream with respect to the direction of reading relative to the direction of transcription from the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art that directly or indirectly regulate the level of transcription with said promoter. A "constitutive" promoter is a promoter that is active in most tissues under typical physiological and developmental conditions. An "inducible" promoter is a promoter that is physiologically or developmentally regulated, e.g. under the influence of a chemical inducer. A "tissue specific" promoter is only active in specific types of tissues or cells.

The terms "enhancers" or "enhancer" as used herein can refer to a DNA sequence that is located adjacent to the DNA sequence that encodes a recombinant product. Enhancer elements are typically located in a 5' direction from a promoter element or can be located downstream of or within a coding DNA sequence (e.g. a DNA sequence transcribed or translated into a recombinant product or products). Hence, an enhancer element can be located 100 base pairs, 200 base pairs, or 300 or more base pairs upstream of a DNA sequence that encodes a recombinant product, or downstream of said sequence. Enhancer elements can increase the amount of a recombinant product being expressed from a DNA sequence above the level of expression associated with a single promoter element. Multiple enhancer elements are readily available to those of ordinary skill in the art.

The term "selectable marker gene" refers to a gene that when expressed confers a selectable phenotype, for example, antibiotic resistance, on a transformed cell.

As used in the present description, the term "expression" is defined as the transcription and/or translation of a particular nucleotide sequence driven by its promoter.

Use for Treatment

"Gene therapy" is the insertion of genes into subject's cells and/or tissues to treat a disease, typically hereditary diseases, in which a defective mutant allele is replaced with a functional one.

"Treat", "treatment" and "therapy" refer to a method of alleviating or abrogating a biological disorder and/or at least one of attendant symptoms thereof. As used herein, to "alleviate" a disease, disorder or condition means reducing the severity and/or occurrence frequency of the symptoms of a disease, disorder, or condition. Further, references herein to "treatment" include references to curative, palliative and prophylactic treatment.

In one aspect, the subject of treatment, or patient, is a mammal, preferably a human subject. Said subject may be either male or female, of any age.

The term "disorder" means any condition that would benefit from treatment according to the present invention. This includes chronic and acute disorders or diseases including those pathological conditions that predispose the mammal to the disorder in question.

"Disease" is a state of health of an animal where the animal cannot maintain homeostasis, and where if the disease is not ameliorated then the animal's health continues to deteriorate.

The terms "subject," "patient," "individual," and the like are used interchangeably in the present description, and they refer to any animal amenable to the methods described in the present description. In certain non-limiting embodiments, the subject, patient or individual is a human.

"Therapeutically effective amount" refers to that amount of the therapeutic agent being administered during treatment which will relieve to some extent one or more of the symptoms of the disease being treated.

The term "chronic" use refers to continued (uninterrupted) use of agent(s) as opposed to acute (transient) route of administration so as to sustain the initial therapeutic effect (activity) for a long period of time.

"Intermittent" use refers to treatment that is not carried out consistently without interruptions, but which is rather periodic in nature.

DETAILED DESCRIPTION OF INVENTION

Isolated Altered VP1 Protein of Adeno-Associated Virus Serotype 5 (AAV5) Capsid

In one aspect, the present invention relates to an isolated altered VP1 protein of adeno-associated virus serotype 5 (AAV5) capsid for highly-efficient transduction of target cells, comprising the amino acid sequence of a VP1 protein of the wild-type AAV5 capsid, which is encoded by the Cap gene, with one or more substitutions selected from the group comprising:

S651A,
S2A and T711S,
S2A, S651A, and T711S.

The amino acid S2A substitution is understood to mean the substitution of Serine (Ser, S) at position 2 of the VP1 protein of wild-type adeno-associated virus serotype 5 capsid for Alanine (Ala, A).

The amino acid S651A substitution is understood to mean the substitution of Serine (Ser, S) at position 651 of the VP1 protein of wild-type adeno-associated virus serotype 5 capsid for Alanine (Ala, A).

The amino acid T711S substitution is understood to mean the substitution of Threonine (Thr, T) at position 711 of the VP1 protein of wild-type adeno-associated virus serotype 5 capsid for Serine (Ser, S).

In some embodiments, the amino acid sequence of a VP1 protein of the wild-type AAV5 capsid has the amino acid sequence represented by (SEQ ID NO: 1)
MSFVDHPPDWLEEVGEGLREFLGLEAGPPKPKPNQQHQDQARGLVLPGYN

YLGPGNGLDRGEPVNRADEVAREHDISYNEQLEAGDNPYLKYNHADAEFQ

EKLADDTSFGGNLGKAVFQAKKRVLEPFGLVEEGAKTAPTGKRIDDHFPK

RKKARTEEDSKPSTSSDAEAGPSGSQQLQIPAQPASSLGADTMSAGGGGP

LGDNNQGADGVGNASGDWHCDSTWMGDRVVTKSTRTWVLPSYNNHQYREI

KSGSVDGSNANAYFGYSTPWGYFDFNRFHSHWSPRDWQRLINNYWGFRPR

SLRVKIFNIQVKEVTVQDSTTTIANNLTSTVQVFTDDDYQLPYVVGNGTE

-continued

```
GCLPAFPPQVFTLPQYGYATLNRDNTENPTERSSFFCLEYFPSKMLRTGN

NFEFTYNFEEVPFHSSFAPSQNLFKLANPLVDQYLYRFVSTNNTGGVQFN

KNLAGRYANTYKNWFPGPMGRTQGWNLGSGVNRASVSAFATTNRMELEGA

SYQVPPQPNGMTNNLQGSNTYALENTMIFNSQPANPGTTATYLEGNMLIT

SESETQPVNRVAYNVGGQMATNNQSSTTAPATGTYNLQEIVPGSVWMERD

VYLQGPIWAKIPETGAHFHPSPAMGGFGLKEIPPPMMLIKNTPVPGNITS

FSDVPVSSFITQYSTGQVTVEMEWELKKENSKRWNPEIQYTNNYNDPQFV

DFAPDSTGEYRTTRPIGTRYLTRPL.
```

In some embodiments, the isolated altered VP1 protein of the AAV5 capsid includes one substitution at S651A position.

In some embodiments, the isolated altered VP1 protein of the AAV5 capsid has the amino acid sequence represented by

```
                                            (SEQ ID NO: 2)
MSFVDHPPDWLEEVGEGLREFLGLEAGPPKPKPNQQHQDQARGLVLPGYN

YLGPGNGLDRGEPVNRADEVAREHDISYNEQLEAGDNPYLKYNHADAEFQ

EKLADDTSFGGNLGKAVFQAKKRVLEPFGLVEEGAKTAPTGKRIDDHFPK

RKKARTEEDSKPSTSSDAEAGPSGSQQLQIPAQPASSLGADTMSAGGGGP

LGDNNQGADGVGNASGDWHCDSTWMGDRVVTKSTRTWVLPSYNNHQYREI

KSGSVDGSNANAYFGYSTPWGYFDFNRFHSHWSPRDWQRLINNYWGFRPR

SLRVKIFNIQVKEVTVQDSTTTIANNLTSTVQVFTDDDYQLPYVVGNGTE

GCLPAFPPQVFTLPQYGYATLNRDNTENPTERSSFFCLEYFPSKMLRTGN

NFEFTYNFEEVPFHSSFAPSQNLFKLANPLVDQYLYRFVSTNNTGGVQFN

KNLAGRYANTYKNWFPGPMGRTQGWNLGSGVNRASVSAFATTNRMELEGA

SYQVPPQPNGMTNNLQGSNTYALENTMIFNSQPANPGTTATYLEGNMLIT

SESETQPVNRVAYNVGGQMATNNQSSTTAPATGTYNLQEIVPGSVWMERD

VYLQGPIWAKIPETGAHFHPSPAMGGFGLKEIPPPMMLIKNTPVPGNITS

FADVPVSSFITQYSTGQVTVEMEWELKKENSKRWNPEIQYTNNYNDPQFV

DFAPDSTGEYRTTRPIGTRYLTRPL.
```

In some embodiments, the isolated altered VP1 protein of the AAV5 capsid includes the S2A and T711S substitutions.

In some embodiments, the isolated altered VP1 protein of the AAV5 capsid has the amino acid sequence represented by

```
                                            (SEQ ID NO: 3)
MAFVDHPPDWLEEVGEGLREFLGLEAGPPKPKPNQQHQDQARGLVLPGYN

YLGPGNGLDRGEPVNRADEVAREHDISYNEQLEAGDNPYLKYNHADAEFQ

EKLADDTSFGGNLGKAVFQAKKRVLEPFGLVEEGAKTAPTGKRIDDHFPK

RKKARTEEDSKPSTSSDAEAGPSGSQQLQIPAQPASSLGADTMSAGGGGP

LGDNNQGADGVGNASGDWHCDSTWMGDRVVTKSTRTWVLPSYNNHQYREI

KSGSVDGSNANAYFGYSTPWGYFDFNRFHSHWSPRDWQRLINNYWGFRPR

SLRVKIFNIQVKEVTVQDSTTTIANNLTSTVQVFTDDDYQLPYVVGNGTE

GCLPAFPPQVFTLPQYGYATLNRDNTENPTERSSFFCLEYFPSKMLRTGN
```

-continued

```
NFEFTYNFEEVPFHSSFAPSQNLFKLANPLVDQYLYRFVSTNNTGGVQFN

KNLAGRYANTYKNWFPGPMGRTQGWNLGSGVNRASVSAFATTNRMELEGA

SYQVPPQPNGMTNNLQGSNTYALENTMIFNSQPANPGTTATYLEGNMLIT

SESETQPVNRVAYNVGGQMATNNQSSTTAPATGTYNLQEIVPGSVWMERD

VYLQGPIWAKIPETGAHFHPSPAMGGFGLKHPPPMMLIKNTPVPGNITSF

SDVPVSSFITQYSTGQVTVEMEWELKKENSKRWNPEIQYTNNYNDPQFVD

FAPDSTGEYRSTRPIGTRYLTRPL.
```

In some embodiments, the isolated altered VP1 protein of the AAV5 capsid includes the S2A, S651A, and T711S substitutions.

In some embodiments, the isolated altered VP1 protein of the AAV5 capsid has the amino acid sequence represented by

```
                                            (SEQ ID NO: 4)
MAFVDHPPDWLEEVGEGLREFLGLEAGPPKPKPNQQHQDQARGLVLPGYN

YLGPGNGLDRGEPVNRADEVAREHDISYNEQLEAGDNPYLKYNHADAEFQ

EKLADDTSFGGNLGKAVFQAKKRVLEPFGLVEEGAKTAPTGKRIDDHFPK

RKKARTEEDSKPSTSSDAEAGPSGSQQLQIPAQPASSLGADTMSAGGGGP

LGDNNQGADGVGNASGDWHCDSTWMGDRVVTKSTRTWVLPSYNNHQYREI

KSGSVDGSNANAYFGYSTPWGYFDFNRFHSHWSPRDWQRLINNYWGFRPR

SLRVKIFNIQVKEVTVQDSTTTIANNLTSTVQVFTDDDYQLPYVVGNGTE

GCLPAFPPQVFTLPQYGYATLNRDNTENPTERSSFFCLEYFPSKMLRTGN

NFEFTYNFEEVPFHSSFAPSQNLFKLANPLVDQYLYRFVSTNNTGGVQFN

KNLAGRYANTYKNWFPGPMGRTQGWNLGSGVNRASVSAFATTNRMELEGA

SYQVPPQPNGMTNNLQGSNTYALENTMIFNSQPANPGTTATYLEGNMLIT

SESETQPVNRVAYNVGGQMATNNQSSTTAPATGTYNLQEIVPGSVWMERD

VYLQGPIWAKIPETGAHFHPSPAMGGFGLKHPPPMMLIKNTPVPGNITSF

ADVPVSSFITQYSTGQVTVEMEWELKKENSKRWNPEIQYTNNYNDPQFVD

FAPDSTGEYRSTRPIGTRYLTRPL.
```

Isolated Altered VP2 and VP3 Proteins of Adeno-Associated Virus Serotype 5 (AAV5) Capsid The "right side" of a (+)-chain of genomic DNA of adeno-associated virus comprises overlapping sequences encoding three capsid proteins, VP1, VP2 and VP3. Transcription of these genes starts from one promoter, p40. The molecular weights of the corresponding proteins are 87, 72, and 62 kDa, respectively. All of the three proteins are translated from a single mRNA. After transcription, pre-mRNA can be spliced in two different manners, where either longer or shorter intron is excised to form mRNAs of 2300 or 2600 nucleotide long.

Thus, the introduction of mutations into the Cas gene will affect not only the VP1 protein of AAV5 capsid, but also the VP2 and VP3 proteins of AAV5 capsid.

FIG. 6 is a schematic representation of the position of the AAV5 capsid proteins in AAV genome:

2087-4258 bp— VP1
    2495-4258 bp— VP2
    2663-4258 bp— VP3.

It follows from the above that a mutation similar to the mutation S2A in VP1 will be absent in VP2 and VP3, whereas mutations similar to the mutations S651A and/or T711S in VP1 will be present in both VP2 and VP3.

With the consideration of an overlapping sequence encoding the three capsid proteins, VP1, VP2 and VP3, the amino acid substitution S651A in VP1 will correspond to:

the amino acid substitution at position S515A in VP2;

the amino acid substitution at position S459A in VP3.

With the consideration of an overlapping sequence encoding the three capsid proteins, VP1, VP2 and VP3, the amino acid T711S substitution will correspond to:

the amino acid substitution at position T575S in VP2;

the amino acid substitution at position T519S in VP3.

Further, the applicant considers it appropriate to specify the environment of the mutations that have been found, by indicating a short amino acid sequence including said mutations in VP1/VP2/VP3:

For S2A in VP1 (not present in VP2 and VP3)—MSFVDHP;

For S651A in VP1 (S515A in VP2/S459A in VP3)—TSFSDVP;

For T711S in VP1 (T575S in VP2/T519S in VP3)—EYRTTRP.

In some embodiments, the amino acid sequence of the VP2 protein of the wild-type AAV5 capsid has the amino acid sequence represented by

```
                                            (SEQ ID NO: 8)
TAPTGKRIDDHFPKRKKARTEEDSKPSTSSDAEAGPSGSQQLQIPAQPAS

SLGADTMSAGGGGPLGDNNQGADGVGNASGDWHCDSTWMGDRVVTKSTRT

WVLPSYNNHQYREIKSGSVDGSNANAYFGYSTPWGYFDFNRFHSHWSPRD

WQRLINNYWGFRPRSLRVKIFNIQVKEVTVQDSTTTIANNLTSTVQVFTD

DDYQLPYVVGNGTEGCLPAFPPQVFTLPQYGYATLNRDNTENPTERSSFF

CLEYFPSKMLRTGNNFEFTYNFEEVPFHSSFAPSQNLFKLANPLVDQYLY

RFVSTNNTGGVQFNKNLAGRYANTYKNWFPGPMGRTQGWNLGSGVNRASV

SAFATTNRMELEGASYQVPPQPNGMTNNLQGSNTYALENTMIFNSQPANP

GTTATYLEGNMLITSESETQPVNRVAYNVGGQMATNNQSSTTAPATGTYN

LQEIVPGSVWMERDVYLQGPIWAKIPETGAHFHPSPAMGGFGLKHPPPMM

LIKNTPVPGNITSFSDVPVSSFITQYSTGQVTVEMEWELKKENSKRWNPE

IQYTNNYNDPQFVDFAPDSTGEYRTTRPIGTRYLTRPL
```

In some embodiments, the isolated altered VP2 protein of the AAV5 capsid includes the T575S substitution.

In some embodiments, the isolated altered VP2 protein of the AAV5 capsid has the amino acid sequence represented by

```
                                            (SEQ ID NO: 9)
TAPTGKRIDDHFPKRKKARTEEDSKPSTSSDAEAGPSGSQQLQIPAQPAS

SLGADTMSAGGGGPLGDNNQGADGVGNASGDWHCDSTWMGDRVVTKSTRT

WVLPSYNNHQYREIKSGSVDGSNANAYFGYSTPWGYFDFNRFHSHWSPRD

WQRLINNYWGFRPRSLRVKIFNIQVKEVTVQDSTTTIANNLTSTVQVFTD

DDYQLPYVVGNGTEGCLPAFPPQVFTLPQYGYATLNRDNTENPTERSSFF

CLEYFPSKMLRTGNNFEFTYNFEEVPFHSSFAPSQNLFKLANPLVDQYLY

RFVSTNNTGGVQFNKNLAGRYANTYKNWFPGPMGRTQGWNLGSGVNRASV
```

```
-continued
SAFATTNRMELEGASYQVPPQPNGMTNNLQGSNTYALENTMIFNSQPANP

GTTATYLEGNMLITSESETQPVNRVAYNVGGQMATNNQSSTTAPATGTYN

LQEIVPGSVWMERDVYLQGPIWAKIPETGAHFHPSPAMGGFGLKHPPPMM

LIKNTPVPGNITSFSDVPVSSFITQYSTGQVTVEMEWELKKENSKRWNPE

IQYTNNYNDPQFVDFAPDSTGEYRSTRPIGTRYLTRPL
```

In some embodiments, the isolated altered VP2 protein of the AAV5 capsid includes the S515A and T575S substitutions.

In some embodiments, the isolated altered VP2 protein of the AAV5 capsid has the amino acid sequence represented by

```
                                           (SEQ ID NO: 10)
TAPTGKRIDDHFPKRKKARTEEDSKPSTSSDAEAGPSGSQQLQIPAQPAS

SLGADTMSAGGGGPLGDNNQGADGVGNASGDWHCDSTWMGDRVVTKSTRT

WVLPSYNNHQYREIKSGSVDGSNANAYFGYSTPWGYFDFNRFHSHWSPRD

WQRLINNYWGFRPRSLRVKIFNIQVKEVTVQDSTTTIANNLTSTVQVFTD

DDYQLPYVVGNGTEGCLPAFPPQVFTLPQYGYATLNRDNTENPTERSSFF

CLEYFPSKMLRTGNNFEFTYNFEEVPFHSSFAPSQNLFKLANPLVDQYLY

RFVSTNNTGGVQFNKNLAGRYANTYKNWFPGPMGRTQGWNLGSGVNRASV

SAFATTNRMELEGASYQVPPQPNGMTNNLQGSNTYALENTMIFNSQPANP

GTTATYLEGNMLITSESETQPVNRVAYNVGGQMATNNQSSTTAPATGTYN

LQEIVPGSVWMERDVYLQGPIWAKIPETGAHFHPSPAMGGFGLKHPPPMM

LIKNTPVPGNITSFADVPVSSFITQYSTGQVTVEMEWELKKENSKRWNPE

IQYTNNYNDPQFVDFAPDSTGEYRSTRPIGTRYLTRPL
```

In some embodiments, the amino acid sequence of the VP3 protein of the wild-type AAV5 capsid has the amino acid sequence represented by

```
                                           (SEQ ID NO: 11)
MSAGGGGPLGDNNQGADGVGNASGDWHCDSTWMGDRVVTKSTRTWVLPSY

NNHQYREIKSGSVDGSNANAYFGYSTPWGYFDFNRFHSHWSPRDWQRLIN

NYWGFRPRSLRVKIFNIQVKEVTVQDSTTTIANNLTSTVQVFTDDDYQLP

YVVGNGTEGCLPAFPPQVFTLPQYGYATLNRDNTENPTERSSFFCLEYFP

SKMLRTGNNFEFTYNFEEVPFHSSFAPSQNLFKLANPLVDQYLYRFVSTN

NTGGVQFNKNLAGRYANTYKNWFPGPMGRTQGWNLGSGVNRASVSAFATT

NRMELEGASYQVPPQPNGMTNNLQGSNTYALENTMIFNSQPANPGTTATY

LEGNMLITSESETQPVNRVAYNVGGQMATNNQSSTTAPATGTYNLQEIVP

GSVWMERDVYLQGPIWAKIPETGAHFHPSPAMGGFGLKHPPPMMLIKNTP

VPGNITSFSDVPVSSFITQYSTGQVTVEMEWELKKENSKRWNPEIQYTNN

YNDPQFVDFAPDSTGEYRTTRPIGTRYLTRPL
```

In some embodiments, the isolated altered VP3 protein of the AAV5 capsid includes the T519S substitution.

In some embodiments, the isolated altered VP3 protein of the AAV5 capsid has the amino acid sequence represented by

```
                                    (SEQ ID NO: 12)
MSAGGGGPLGDNNQGADGVGNASGDWHCDSTWMGDRVVTKSTRTWVLPSY

NNHQYREIKSGSVDGSNANAYFGYSTPWGYFDFNRFHSHWSPRDWQRLIN

NYWGFRPRSLRVKIFNIQVKEVTVQDSTTTIANNLTSTVQVFTDDDYQLP

YVVGNGTEGCLPAFPPQVFTLPQYGYATLNRDNTENPTERSSFFCLEYFP

SKMLRTGNNFEFTYNFEEVPFHSSFAPSQNLFKLANPLVDQYLYRFVSTN

NTGGVQFNKNLAGRYANTYKNWFPGPMGRTQGWNLGSGVNRASVSAFATT

NRMELEGASYQVPPQPNGMTNNLQGSNTYALENTMIFNSQPANPGTTATY

LEGNMLITSESETQPVNRVAYNVGGQMATNNQSSTTAPATGTYNLQEIVP

GSVWMERDVYLQGPIWAKIPETGAHFHPSPAMGGFGLKHPPPMMLIKNTP

VPGNITSFSDVPVSSFITQYSTGQVTVEMEWELKKENSKRWNPEIQYTNN

YNDPQFVDFAPDSTGEYRSTRPIGTRYLTRPL
```

In some embodiments, the isolated altered VP3 protein of the AAV5 capsid includes the S459A and T519S substitutions.

In some embodiments, the isolated altered VP3 protein of the AAV5 capsid has the amino acid sequence represented by

```
                                    (SEQ ID NO: 13)
MSAGGGGPLGDNNQGADGVGNASGDWHCDSTWMGDRVVTKSTRTWVLPSY

NNHQYREIKSGSVDGSNANAYFGYSTPWGYFDFNRFHSHWSPRDWQRLIN

NYWGFRPRSLRVKIFNIQVKEVTVQDSTTTIANNLTSTVQVFTDDDYQLP

YVVGNGTEGCLPAFPPQVFTLPQYGYATLNRDNTENPTERSSFFCLEYFP

SKMLRTGNNFEFTYNFEEVPFHSSFAPSQNLFKLANPLVDQYLYRFVSTN

NTGGVQFNKNLAGRYANTYKNWFPGPMGRTQGWNLGSGVNRASVSAFATT

NRMELEGASYQVPPQPNGMTNNLQGSNTYALENTMIFNSQPANPGTTATY

LEGNMLITSESETQPVNRVAYNVGGQMATNNQSSTTAPATGTYNLQEIVP

GSVWMERDVYLQGPIWAKIPETGAHFHPSPAMGGFGLKHPPPMMLIKNTP

VPGNITSFADVPVSSFITQYSTGQVTVEMEWELKKENSKRWNPEIQYTNN

YNDPQFVDFAPDSTGEYRSTRPIGTRYLTRPL
```

Capsid

In one aspect, the present invention relates to an isolated capsid for highly-efficient transduction of target cells, which includes the above altered VP1 protein of adeno-associated virus serotype 5 (AAV5) capsid.

In one embodiment, the isolated capsid includes the above altered VP1 protein of adeno-associated virus serotype 5 (AAV5) capsid, a VP2 protein of AAV5 capsid or an altered variant thereof, and a VP3 protein of AAV5 capsid or an altered variant thereof.

Particularly preferred embodiments include substitutions that are conservative in nature, i.e. substitutions which that take place within a family of amino acids that are joined in their side chains. In particular, amino acids are typically divided into four families: (1) acidic amino acids are aspartate and glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. Phenylalanine, tryptophan, and tyrosine are sometimes classified as aromatic amino acids. For example, it is reasonably predictable that an isolated substitution of leucine for isoleucine or valine, an aspartate for a glutamate, a threonine for a serine, or a similar conservative substitution of an amino acid for a structurally related amino acid, will not have a major effect on the biological activity. For example, the polypeptide of interest may include up to about 5-10 conservative or non-conservative amino acid substitutions, or even up to about 15-25 or 50 conservative or non-conservative amino acid substitutions, or any integer between 5-50, so long as the desired function of the molecule remains intact.

In one embodiment, the isolated capsid includes a VP2 protein of the wild-type AAV5 capsid.

In one embodiment, the isolated capsid includes the VP2 protein of the wild-type AAV5 capsid, which has the amino acid sequence represented by SEQ ID NO: 8.

In one embodiment, the isolated capsid includes the altered VP2 protein of adeno-associated virus serotype 5 (AAV5) capsid.

In one embodiment, the isolated capsid includes the altered VP2 protein of AAV5 capsid, which comprises the T575S substitution.

In one embodiment, the isolated capsid includes the altered VP2 protein of AAV5 capsid, which comprises the T575S substitution, and has the amino acid sequence represented by SEQ ID NO: 9.

In one embodiment, the isolated capsid includes the altered VP2 protein of AAV5 capsid, which comprises the S515A and T575S substitutions.

In one embodiment, the isolated capsid includes the altered VP2 protein of AAV5 capsid, which comprises the S515A and T575S substitutions, and has the amino acid sequence represented by SEQ ID NO: 10.

In one embodiment, the isolated capsid includes a VP3 protein of the wild-type AAV5 capsid.

In one embodiment, the isolated capsid includes the VP3 protein of the wild-type AAV5 capsid, which has the amino acid sequence represented by SEQ ID NO: 11.

In one embodiment, the isolated capsid includes an altered VP3 protein of adeno-associated virus serotype 5 (AAV5) capsid.

In one embodiment, the isolated capsid includes an altered VP3 protein of AAV5 capsid, which comprises the T519S substitution.

In one embodiment, the isolated capsid includes an altered VP3 protein of AAV5 capsid, which comprises the T519S substitution, and has the amino acid sequence represented by SEQ ID NO: 12.

In one embodiment, the isolated capsid includes an altered VP3 protein of AAV5 capsid, which comprises the S459A and T519S substitutions.

In one embodiment, the isolated capsid includes an altered VP3 protein of AAV5 capsid, which comprises the S459A and T519S substitutions, and has the amino acid sequence represented by SEQ ID NO: 13.

Isolated Nucleic Acid

In one aspect, the present invention relates to an isolated nucleic acid encoding the above altered VP1 protein of adeno-associated virus serotype 5 (AAV5) capsid, which is used for highly efficient transduction of target cells.

In some embodiments, the isolated nucleic acid encoding the altered VP1 protein of adeno-associated virus serotype 5 (AAV5) capsid with the amino acid S651A substitution is represented by the nucleic sequence ATGTCTTTTGTT-GATCACCCTCCAGATTGGTTGGAAGAAGTTGGT-GAAGGTCTTCGCGA GTTTTTGGGCCTT- GAAGCGGGCCCACCGAAACCAAAACCCAATCAGC-
AGCATCAAGAT
CAAGCCCGTGGTCTTGTGCTGCCTGGTTATAAC-
TATCTCGGACCCGGAAACGGTCTCGA TCGAG-
GAGAGCCTGTCAACAGGGCA-
GACGAGGTCGCGCGAGAGCACGACATCTCGTAC
AACGAGCAGCTTGAGGCGGGAGACAACCCC-
TACCTCAAGTACAACCACGCGGACGCCG
AGTTTCAGGAGAAGCTCGCCGACGACA-
CATCCTTCGGGGGAAACCTCGGAAAGGCAGT
CTTTCAGGC-
CAAGAAAAGGGTTCTCGAACCTTTTGGCCTGGTT-
GAAGAGGGTGCTAAGA CGGCCCCTACCG-
GAAAGCGGATAGACGACCACTTTCCAAAAAGAAA-
GAAGGCTCGGAC CGAAGAGGACTCCAAGCCTTC-
CACCTCGTCAGACGCCGAAGCTGGACCCAGCG-
GATCC CAGCAGCTGCAAATCCCAGCC-
CAACCAGCCTCAAGTTTGGGAGCTGATACAATGTC-
TGC GGGAGGTGGCGGCCCATTGGGCGACAATAAC-
CAAGGTGCCGATGGAGTGGGCAATGCC TCGG-
GAGATTGGCATTGCGATTCCACGTG-
GATGGGGGACAGAGTCGTCACCAAGTCCA
CCCGAACCTGGGTGCTGCCCAGCTACAACAAC-
CACCAGTACCGAGAGATCAAAAGCGG
CTCCGTCGACGGAAGCAACGCCAACGCC-
TACTTTGGATACAGCACCCCCTGGGGGTACT
TTGACTTTAACCGCTTCCACAGCCACTG-
GAGCCCCCGAGACTGGCAAAGACTCATCAAC AAC-
TACTGGGGCTTCAGACCCCGGTCCCTCAGAGT-
CAAAATCTTCAACATTCAAGTCAA
AGAGGTCACGGTGCAGGACTCCACCACCAC-
CATCGCCAACAACCTCACCTCCACCGTCC
AAGTGTTTACGGACGACGACTACCAGCTGCCC-
TACGTCGTCGGCAACGGGACCGAGGG
ATGCCTGCCGGCCTTCCCTCCGCAGGTCTT-
TACGCTGCCGCAGTACGGTTACGCGACGC
TGAACCGCGACAACACAGAAAATCCCACCGAGAG-
GAGCAGCTTCTTCTGCCTAGAGTA
CTTTCCCAGCAAGATGCT-
GAGAACGGGCAACAACTTTGAGTTTACCTA-
CAACTTTGAGG AGGTGCCCTTC-
CACTCCAAGCTTCGCTCCCAGTCAGAACCTGTTCAA-
GCTGGCCAACCCG
CTGGTGGACCAGTACTTGTACCGCTTCGT-
GAGCACAAATAACACTGGCGGAGTCCAGTT
CAACAAGAACCTGGCCGGGAGATACGCCAACACC-
TACAAAAACTGGTTCCCGGGGCCC
ATGGGCCGAACCCAGGGCTG-
GAACCTGGGCTCCGGGGT-
CAACCGCGCCAGTGTCAGCG CCTTCGCCACGAC-
CAATAGGATGGAGCTCGAGGGCGCGAGTTACCAG-
GTGCCCCCGCA GCCGAACGGCATGAC-
CAACAACCTCCAGGGCAGCAACACCTATGCCCTG-
GAGAACACT ATGATCTT-
CAACAGCCAGCCGGCGAACCCGGGCACCACCGCC-
ACGTACCTCGAGGGCA ACATGCTCAT-
CACCAGCGAGAGCGAGACGCAGCCGGT-
GAACCGCGTGGCGTACAACGT CGGCGGGCA-
GATGGCCACCAACAACCAGAGCTCCACCACTGCC-
CCCGCGACCGGCACG TACAACCTCCAG-
GAAATCGTGCCCGGCAGCGTGTGGATG-
GAGAGGGACGTGTACCTCC AAGGACC-
CATCTGGGCCAAGATCCCAGAGACGGGGGCGCAC-
TTTCACCCCTCTCCGGC CATGGGCGGATTCGGACT-
CAAACACCCACCGCCCATGATGCTCAT-
CAAGAACACGCCT GTGCCCGGAAATAT-
CACCAGCTTCgCGGACGTGCCCGTCAGCAGCTTCA- TCACCCAGTA CAGCACCGGGCAGGTCACCGTG-
GAGATGGAGTGGGAGCTCAAGAAGGAAAACTC-
CAA GAGGTGGAACCCAGAGATCCAGTA-
CACAAACAACTACAACGACCCCCAGTTTGTGGAC
TTTGCCCCGGACAGCACCGGGGAATACAGAAC-
CACCAGACCTATCGGAACCCGATACC
TTACCCGACCCCTTTAA (SEQ ID NO: 5) or by any other
sequence encoding the corresponding amino acid sequence
of the altered protein of adeno-associated virus serotype 5
(AAV5) capsid with the amino acid S651A substitution.

"Other sequence encoding the corresponding amino acid
sequence of the altered VP1 protein of adeno-associated
virus serotype 5 (AAV5) capsid with the amino acid S651A
substitution" means a nucleic sequence that is alternative to
the nucleic sequence with SEQ ID NO: 5, as, due to the
degeneracy of genetic code, a wide range of different DNA
sequences can encode the amino acid sequence disclosed
herein as SEQ ID NO: 2. It is well within the skill of a person
trained in the art to create these alternative DNA sequences
encoding the same amino acid sequences. Such variant DNA
sequences are within the scope of the present invention.

In some embodiments, the isolated nucleic acid encoding
the altered VP1 protein of adeno-associated virus serotype 5
(AAV5) capsid with the amino acid S2A and T711S substi-
tutions, which is represented by the nucleic sequence
ATGGCTTTTGTTGATCACCCTCCAGATTGGTTG-
GAAGAAGTTGGTGAAGGTCTTCGCGA
GTTTTTGGGCCTTGAAGCGGGCCCACCGAAAC-
CAAAACCCAATCAGCAGCATCAAGAT
CAAGCCCGTGGTCTTGTGCTGCCTGGTTATAAC-
TATCTCGGACCCGGAAACGGTCTCGA TCGAG-
GAGAGCCTGTCAACAGGGCA-
GACGAGGTCGCGCGAGAGCACGACATCTCGTAC
AACGAGCAGCTTGAGGCGGGAGACAACCCC-
TACCTCAAGTACAACCACGCGGACGCCG
AGTTTCAGGAGAAGCTCGCCGACGACA-
CATCCTTCGGGGGAAACCTCGGAAAGGCAGT
CTTTCAGGC-
CAAGAAAAGGGTTCTCGAACCTTTTGGCCTGGTT-
GAAGAGGGTGCTAAGA CGGCCCCTACCG-
GAAAGCGGATAGACGACCACTTTCCAAAAAGAAA-
GAAGGCTCGGAC CGAAGAGGACTCCAAGCCTTC-
CACCTCGTCAGACGCCGAAGCTGGACCCAGCG-
GATCC CAGCAGCTGCAAATCCCAGCC-
CAACCAGCCTCAAGTTTGGGAGCTGATACAATGTC-
TGC GGGAGGTGGCGGCCCATTGGGCGACAATAAC-
CAAGGTGCCGATGGAGTGGGCAATGCC TCGG-
GAGATTGGCATTGCGATTCCACGTG-
GATGGGGGACAGAGTCGTCACCAAGTCCA
CCCGAACCTGGGTGCTGCCCAGCTACAACAAC-
CACCAGTACCGAGAGATCAAAAGCGG
CTCCGTCGACGGAAGCAACGCCAACGCC-
TACTTTGGATACAGCACCCCCTGGGGGTACT
TTGACTTTAACCGCTTCCACAGCCACTG-
GAGCCCCCGAGACTGGCAAAGACTCATCAAC AAC-
TACTGGGGCTTCAGACCCCGGTCCCTCAGAGT-
CAAAATCTTCAACATTCAAGTCAA
AGAGGTCACGGTGCAGGACTCCACCACCAC-
CATCGCCAACAACCTCACCTCCACCGTCC
AAGTGTTTACGGACGACGACTACCAGCTGCCC-
TACGTCGTCGGCAACGGGACCGAGGG
ATGCCTGCCGGCCTTCCCTCCGCAGGTCTT-
TACGCTGCCGCAGTACGGTTACGCGACGC
TGAACCGCGACAACACAGAAAATCCCACCGAGAG-
GAGCAGCTTCTTCTGCCTAGAGTA CTTTCCCAGCAAGATGCT-GAGAACGGGCAACAACTTTGAGTTTACCTA-CAACTTTGAGG AGGTGCCCTTC-CACTCCAGCTTCGCTCCCAGTCAGAACCTCTTCAA-GCTGGCCAACCCG CTGGTGGACCAGTACTTGTACCGCTTCGT-GAGCACAAATAACACTGGCGGAGTCCAGTT CAACAAGAACCTGGCCGGGAGATACGCCAACACC-TACAAAAACTGGTTCCCGGGGCCC ATGGGCCGAACCCAGGGCTG-GAACCTGGGCTCCGGGGT-CAACCGCGCCAGTGTCAGCG CCTTCGCCACGAC-CAATAGGATGGAGCTCGAGGGCGCGAGTTACCAG-GTGCCCCCGCA GCCGAACGGCATGAC-CAACAACCTCCAGGGCAGCAACACCTATGCCCTG-GAGAACACT ATGATCTT-CAACAGCCAGCCGGCGAACCCGGGCACCACCGCC-ACGTACCTCGAGGGCA ACATGCTCAT-CACCAGCGAGAGCGAGACGCAGCCGGT-GAACCGCGTGGCGTACAACGT CGGCGGGCA-GATGGCCACCAACAACCAGAGCTCCACCACTGCC-CCCGCGACCGGCACG TACAACCTCCAG-GAAATCGTGCCCGGCAGCGTGTGGATG-GAGAGGGACGTGTACCTCC AAGGACC-CATCTGGGCCAAGATCCCAGAGACGGGGGCGCAC-TTTCACCCCTCTCCGGC CATGGGCGGATTCGGACT-CAAACACCCACCGCCCATGATGCTCAT-CAAGAACACGCCT GTGCCCGGAAATAT-CACCAGCTTCTCGGACGTGCCCGTCAGCAGCTTC-ATCACCCAGTA CAGCACCGGGCAGGTCACCGTG-GAGATGGAGTGGGAGCTCAAGAAGGAAAACTC-CAA GAGGTGGAACCCAGAGATCCAGTA-CACAAACAACTACAACGACCCCCAGTTTGTGGAC TTTGCCCCGGACAGCACCGGGGAATA-CAGAAGCACCAGACCTATCGGAACCCGATACC TTACCCGACCCCTTTAA (SEQ ID NO: 6) or by any other sequence encoding the corresponding amino acid sequence of the altered VP1 protein of adeno-associated virus serotype 5 (AAV5) capsid with the amino acid S2A and T711S substitutions.

"Other sequence encoding the corresponding amino acid sequence of the altered VP1 protein of adeno-associated virus serotype 5 (AAV5) capsid with the amino acid S2A and T711S substitutions" means a nucleic sequence that is alternative to the nucleic sequence with SEQ ID NO: 6, as, due to the degeneracy of genetic code, a wide range of different DNA sequences can encode the amino acid sequence disclosed herein as SEQ ID NO: 3. It is well within the skill of a person trained in the art to create these alternative DNA sequences encoding the same amino acid sequences. Such variant DNA sequences are within the scope of the present invention.

In some embodiments, the isolated nucleic acid encoding the altered VP1 protein of adeno-associated virus serotype 5 (AAV5) capsid with the amino acid S2A, S651A and T711S substitutions, which is represented by the nucleic sequence ATGGCTTTTGTTGATCACCCTCCAGATTGGTTG-GAAGAAGTTGGTGAAGGTCTTCGCGA GTTTTTGGGCCTTGAAGCGGGCCCACCGAAAC-CAAAACCCAATCAGCAGCATCAAGAT CAAGCCCGTGGTCTTGTGCTGCCTGGTTATAAC-TATCTCGGACCCGGGAAACGGTCTCGA TCGAG-GAGAGCCTGTCAACAGGGCA-GACGAGGTCGCGCGAGAGCACGACATCTCGTAC AACGAGCAGCTTGAGGCGGGGAGACAACCCC- TACCTCAAGTACAACCACGCGGACGCCG AGTTTCAGGAGAAGCTCGCCGACGACA-CATCCTTCGGGGGGAAACCTCGGAAAGGCAGT CTTTCAGGC-CAAGAAAAGGGTTCTCGAACCTTTTGGCCTGGTT-GAAGAGGGTGCTAAGA CGGCCCCTACCG-GAAAGCGGATAGACGACCACTTTCCAAAAAGAAA-GAAGGCTCGGAC CGAAGAGGACTCCAAGCCTTC-CACCTCGTCAGACGCCGAAGCTGGACCCAGCG-GATCC CAGCAGCTGCAAATCCCAGCC-CAACCAGCCTCAAGTTTGGGAGCTGATACAATGTC-TGC GGGAGGTGGCGGCCCATTGGGCGACAATAAC-CAAGGTGCCGATGGAGTGGGCAATGCC TCGG-GAGATTGGCATTGCGATTCCACGTG-GATGGGGGACAGAGTCGTCACCAAGTCCA CCCGAACCTGGGTGCTGCCCAGCTACAACAAC-CACCAGTACCGAGAGATCAAAAGCGG CTCCGTCGACGGAAGCAACGCCAACGCC-TACTTTGGATACAGCACCCCCTGGGGGTACT TTGACTTTAACCGCTTCCACAGCCACTG-GAGCCCCCGAGACTGGCAAAGACTCATCAAC AAC-TACTGGGGCTTCAGACCCCGGTCCCTCAGAGT-CAAAATCTTCAACATTCAAGTCAA AGAGGTCACGGTGCAGGACTCCACCACCAC-CATCGCCAACAACCTCACCTCCACCGTCC AAGTGTTTACGGACGACGACTACCAGCTGCCC-TACGTCGTCGGCAACGGGACCGAGGG ATGCCTGCCGGCCTTCCCTCCGCAGGTCTT-TACGCTGCCGCAGTACGGTTACGCGACGC TGAACCGCGACAACACAGAAAATCCCACCGAGAG-GAGCAGCTTCTTCTGCCTAGAGTA CTTTCCCAGCAAGATGCT-GAGAACGGGCAACAACTTTGAGTTTACCTA-CAACTTTGAGG AGGTGCCCTTC-CACTCCAGCTTCGCTCCCAGTCAGAACCTCTTCAA-GCTGGCCAACCCG CTGGTGGACCAGTACTTGTACCGCTTCGT-GAGCACAAATAACACTGGCGGAGTCCAGTT CAACAAGAACCTGGCCGGGAGATACGCCAACACC-TACAAAAACTGGTTCCCGGGGCCC ATGGGCCGAACCCAGGGCTG-GAACCTGGGCTCCGGGGT-CAACCGCGCCAGTGTCAGCG CCTTCGCCACGAC-CAATAGGATGGAGCTCGAGGGCGCGAGTTACCAG-GTGCCCCCGCA GCCGAACGGCATGAC-CAACAACCTCCAGGGCAGCAACACCTATGCCCTG-GAGAACACT ATGATCTT-CAACAGCCAGCCGGCGAACCCGGGCACCACCGCC-ACGTACCTCGAGGGCA ACATGCTCAT-CACCAGCGAGAGCGAGACGCAGCCGGT-GAACCGCGTGGCGTACAACGT CGGCGGGCA-GATGGCCACCAACAACCAGAGCTCCACCACTGCC-CCCGCGACCGGCACG TACAACCTCCAG-GAAATCGTGCCCGGCAGCGTGTGGATG-GAGAGGGACGTGTACCTCC AAGGACC-CATCTGGGCCAAGATCCCAGAGACGGGGGCGCAC-TTTCACCCCTCTCCGGC CATGGGCGGATTCGGACT-CAAACACCCACCGCCCATGATGCTCAT-CAAGAACACGCCT GTGCCCGGAAATAT-CACCAGCTTCgCGGACGTGCCCGTCAGCAGCTTCA-TCACCCAGTA CAGCACCGGGCAGGTCACCGTG-GAGATGGAGTGGGAGCTCAAGAAGGAAAACTC-CAA GAGGTGGAACCCAGAGATCCAGTA-CACAAACAACTACAACGACCCCCAGTTTGTGGAC TTTGCCCCGGACAGCACCGGGGAATA- CAGAAGCACCAGACCTATCGGAACCCGATACC TTACCCGACCCCTTTAA (SEQ ID NO: 7) or by any other sequence encoding the corresponding amino acid sequence of the altered VP1 protein of adeno-associated virus serotype 5 (AAV5) capsid with the amino acid S2A, S651A and T711S substitutions.

"Other sequence encoding the corresponding amino acid sequence of the altered VP1 protein of adeno-associated virus serotype 5 (AAV5) capsid with the amino acid S2A, S651A and T711S substitutions" means a nucleic sequence that is alternative to the nucleic sequence with SEQ ID NO: 7, as, due to the degeneracy of genetic code, a wide range of different DNA sequences can encode the amino acid sequence disclosed herein as SEQ ID NO: 4. It is well within the skill of a person trained in the art to create these alternative DNA sequences encoding the same amino acid sequences. Such variant DNA sequences are within the scope of the present invention.

The isolated nucleic acid encoding the above VP1 of wild-type adeno-associated virus serotype 5 (AAV5) capsid is represented by the nucleic sequence
ATGTCTTTTGTTGATCACCCTCCAGATTGGTTG-GAAGAAGTTGGTGAAGGTCTTC GCGAGTTTTTGGGCCTTGAAGCGGGCC-CACCGAAACCAAAACCCAATCAGCAGCATCA AGATCAAGCCCGTGGTCTTGTGCTGCCTGGT-TATAACTATCTCGGACCCGGAAACGGTC TCGATCGAGGAGAGCCTGTCAACAGGGCA-GACGAGGTCGCGCGAGAGCACGACATCTC GTA-CAACGAGCAGCTTGAGGCGGGAGACAACCCC-TACCTCAAGTACAACCACGCGGAC GCCGAGTTTCAGGAGAAGCTCGCCGACGACA-CATCCTTCGGGGGAAACCTCGGAAAGG CAGTCTTTCAGGC-CAAGAAAAGGGTTCTCGAACCTTTTGGCCTGGTT-GAAGAGGGTGCT AAGACGGCCCCTACCG-GAAAGCGGATAGACGACCACTTTCCAAAAAGAAA-GAAGGCTC GGACCGAAGAGGACTCCAAGCCTTC-CACCTCGTCAGACGCCGAAGCTGGACCCAGCGG ATCCCAGCAGCTGCAAATCCCAGCCCAACCAGCCT-CAAGTTTGGGAGCTGATACAATGT CTGCGG-GAGGTGGCGGCCCATTGGGCGACAATAAC-CAAGGTGCCGATGGAGTGGGCAA TGCCTCGGGAGATTGGCATTGCGATTCCACGTG-GATGGGGGACAGAGTCGTCACCAAG TCCACCCGAACCTGGGTGCTGCCCAGCTA-CAACAACCACCAGTACCGAGAGATCAAAA GCGGCTCCGTCGACGGAAGCAACGCCAACGCC-TACTTTGGATACAGCACCCCCTGGGG GTACTTTGACTTTAACCGCTTCCACAGCCACTG-GAGCCCCCGAGACTGGCAAAGACTCATCAACAAC-TACTGGGGCTTCAGACCCCGGTCCCTCAGAGT-CAAAATCTTCAACATTCAA GTCAAAGAGGTCACGGTGCAGGACTCCACCAC-CACCATCGCCAACAACCTCACCTCCA CCGTC-CAAGTGTTTACGGACGACGACTACCAGCTGCCC-TACGTCGTCGGCAACGGGACC GAGGGATGCCTGCCGGCCTTCCCTCCGCAGGTCTT-TACGCTGCCGCAGTACGGTTACGC GACGCT-GAACCGCGACAACACAGAAAATCCCACCGAGAG-GAGCAGCTTCTTCTGCCTA GAGTACTTTCCCAGCAAGATGCT-GAGAACGGGCAACAACTTTGAGTTTACCTA-CAACTT TGAGGAGGTGCCCTTC-CACTCCAGCTTCGCTCCCAGTCAGAACCTCTTCA-AGCTGGCCA ACCCGCTGGTGGACCAGTACTTGTACCGCTTCGT- GAGCACAAATAACACTGGCGGAGTC CAGTT-CAACAAGAACCTGGCCGGGGAGATACGCCAACACC-TACAAAAACTGGTTCCCGG GGCCCATGGGCCGAACCCAGGGCTG-GAACCTGGGCTCCGGGGTCAACCGCGCCAGTGT CAGCGCCTTCGCCACGACCAATAGGATG-GAGCTCGAGGGCGCGAGTTACCAGGTGCCC CCGCAGCCGAACGGCATGAC-CAACAACCTCCAGGGCAGCAACACCTATGCCCTG-GAGA ACACTATGATCTT-CAACAGCCAGCCGGCGAACCCGGGCACCACCGCC-ACGTACCTCGA GGGCAACATGCTCAT-CACCAGCGAGAGCGAGACGCAGCCGGT-GAACCGCGTGGCGTAC AACGTCGGCGGGCA-GATGGCCACCAACAACCAGAGCTCCACCACTGCC-CCCGCGACCG GCACGTACAACCTCCAG-GAAATCGTGCCCGGCAGCGTGTGGATG-GAGAGGGACGTGTA CCTCCAAGGACC-CATCTGGGCCAAGATCCCAGAGACGGGGGCGCAC-TTTCACCCCTCTC CGGCCATGGGCGGATTCGGACT-CAAACACCCACCGCCCATGATGCTCAT-CAAGAACAC GCCTGTGCCCGGAAATAT-CACCAGCTTCTCGGACGTGCCCGTCAGCAGCTTC-ATCACCC AGTACAGCACCGGGCAGGTCACCGTG-GAGATGGAGTGGGAGCTCAAGAAGGAAAACT CCAAGAGGTGGAACCCAGAGATCCAGTA-CACAAACAACTACAACGACCCCCAGTTTGT GGACTTTGCCCCGGACAGCACCGGGGAATA-CAGAACCACCAGACCTATCGGAACCCGA TACCT-TACCCGACCCCTTTAA (SEQ ID NO: 14) or by any other sequence encoding the corresponding amino acid sequence of the VP1 protein of wild-type adeno-associated virus serotype 5 (AAV5) capsid.

"Other sequence encoding the corresponding amino acid sequence of the VP1 protein of wild-type adeno-associated virus serotype 5 (AAV5) capsid" means a nucleic sequence that is alternative to the nucleic sequence with SEQ ID NO: 14, as, due to the degeneracy of genetic code, a wide range of different DNA sequences can encode the amino acid sequence disclosed herein as SEQ ID NO: 1. It is well within the skill of a person trained in the art to create these alternative DNA sequences encoding the same amino acid sequences. Such variant DNA sequences are within the scope of the present invention.

In one aspect, the present invention relates to an isolated nucleic acid encoding the above altered VP2 protein of adeno-associated virus serotype 5 (AAV5) capsid.

In some embodiments, the isolated nucleic acid encoding the altered VP2 protein of adeno-associated virus serotype 5 (AAV5) capsid with the amino acid T575S substitution is represented by the nucleic sequence ACGGCCCCTACCG-GAAAGCGGATAGACGACCACTTTC-CAAAAAGAAAGAAGGCTCGGA CCGAAGAGGACTCCAAGCCTTCCACCTCGTCA-GACGCCGAAGCTGGACCCAGCGGATC CCAGCAGCTGCAAATCCCAGCCCAACCAGCCT-CAAGTTTGGGAGCTGATACAATGTCTG CGG-GAGGTGGCGGCCCATTGGGCGACAATAAC-CAAGGTGCCGATGGAGTGGGCAATGC CTCGGGAGATTGGCATTGCGATTCCACGTG-GATGGGGGACAGAGTCGTCACCAAGTCC ACCCGAACCTGGGTGCTGCCCAGCTACAACAAC-CACCAGTACCGAGAGATCAAAAGCG GCTCCGTCGACGGAAGCAACGCCAACGCC-TACTTTGGATACAGCACCCCCTGGGGGTA CTTTGACTTTAACCGCTTCCACAGCCACTG-
GAGCCCCCGAGACTGGCAAAGACTCATCA ACAAC-
TACTGGGGCTTCAGACCCCGGTCCCTCAGAGT-
CAAAATCTTCAACATTCAAGTC
AAAGAGGTCACGGTGCAGGACTCCACCACCAC-
CATCGCCAACAACCTCACCTCCACCG
TCCAAGTGTTTACGGACGACGAC-
TACCAGCTGCCCTACGTCGTCGGCAACGGGACCGA
GGGATGCCTGCCGGCCTTCCCTCCGCAGGTCTT-
TACGCTGCCGCAGTACGGTTACGCGA     CGCT-
GAACCGCGACAACACAGAAAATCCCACCGAGAG-
GAGCAGCTTCTTCTGCCTAGA
GTACTTTCCCAGCAAGATGCT-
GAGAACGGGCAACAACTTTGAGTTTACCTA-
CAACTTTG                 AGGAGGTGCCCTTC-
CACTCCAGCTTCGCTCCCAGTCAGAACCTCTTCAA-
GCTGGCCAAC
CCGCTGGTGGACCAGTACTTGTACCGCTTCGT-
GAGCACAAATAACACTGGCGGAGTCCA     GTT-
CAACAAGAACCTGGCCGGGAGATACGCCAACACC-
TACAAAAACTGGTTCCCGGGG
CCCATGGGCCGAACCCAGGGCTG-
GAACCTGGGCTCCGGGGT-
CAACCGCGCCAGTGTCA   GCGCCTTCGCCACGAC-
CAATAGGATGGAGCTCGAGGGCGCGAGTTACCAG-
GTGCCCCC                 GCAGCCGAACGGCATGAC-
CAACAACCTCCAGGGCAGCAACACCTATGCCCTG-
GAGAAC                     ACTATGATCTT-
CAACAGCCAGCCGGCGAACCCGGGCACCACCGCC-
ACGTACCTCGAGG                 GCAACATGCTCAT-
CACCAGCGAGAGCGAGACGCAGCCGGT-
GAACCGCGTGGCGTACAA     CGTCGGCGGGCA-
GATGGCCACCAACAACCAGAGCTCCACCACTGCC-
CCCGCGACCGGC                 ACGTACAACCTCCAG-
GAAATCGTGCCCGGCAGCGTGTGGATG-
GAGAGGGACGTGTACC                 TCCAAGGACC-
CATCTGGGCCAAGATCCCAGAGACGGGGGCGCAC-
TTTCACCCCTCTCCG GCCATGGGCGGATTCGGACT-
CAAACACCCACCGCCCATGATGCTCAT-
CAAGAACACGC                 CTGTGCCCGGAAATAT-
CACCAGCTTCTCGGACGTGCCCGTCAGCAGCTTC-
ATCACCCAG   TACAGCACCGGGCAGGTCACCGTG-
GAGATGGAGTGGGAGCTCAAGAAGGAAAACTCC
AAGAGGTGGAACCCAGAGATCCAGTA-
CACAAACAACTACAACGACCCCCAGTTTGTGG
ACTTTGCCCCGGACAGCACCGGGGAATA-
CAGAAGCACCAGACCTATCGGAACCCGATA     CCT-
TACCCGACCCCTTTAA (SEQ ID NO: 15) or by any other
sequence encoding the corresponding amino acid sequence
of the altered VP2 protein of adeno-associated virus sero-
type 5 (AAV5) capsid with the amino acid T575S substitu-
tion.

"Other sequence encoding the corresponding amino acid
sequence of the altered VP2 protein of adeno-associated
virus serotype 5 (AAV5) capsid with the amino acid T575S
substitution" means a nucleic sequence that is alternative to
the nucleic sequence with SEQ ID NO: 15, as, due to the
degeneracy of genetic code, a wide range of different DNA
sequences can encode the amino acid sequence disclosed
herein as SEQ ID NO: 9. It is well within the skill of a person
trained in the art to create these alternative DNA sequences
encoding the same amino acid sequences. Such variant DNA
sequences are within the scope of the present invention.

In some embodiments, the isolated nucleic acid encoding
the altered VP2 protein of adeno-associated virus serotype 5
(AAV5) capsid with the amino acid S515A and T575S
substitutions has any nucleic acid sequence that encodes the amino acid sequence disclosed herein as SEQ ID NO: 10. It
is well within the skill of a person trained in the art to create
these alternative DNA sequences encoding the same amino
acid sequences. Such variant DNA sequences are within the
scope of the present invention.

The isolated nucleic acid encoding the above VP2 of
wild-type adeno-associated virus serotype 5 (AAV5) capsid
is represented by the nucleic sequence ACGGCCCC-
TACCGGAAAGCGGATAGACGACCACTTTC-
CAAAAAGAAAGAAGGCTCGGA
CCGAAGAGGACTCCAAGCCTTCCACCTCGTCA-
GACGCCGAAGCTGGACCCAGCGGATC
CCAGCAGCTGCAAATCCCAGCCCAACCAGCCT-
CAAGTTTGGGAGCTGATACAATGTCTG     CGG-
GAGGTGGCGGCCCATTGGGCGACAATAAC-
CAAGGTGCC                 GATGGAGTGGGCAATGC
CTCGGGAGATTGGCATTGCGATTCCACGTG-
GATGGGGGACAGAGTCGTCACCAAGTCC
ACCCGAACCTGGGTGCTGCCCAGCTACAACAAC-
CACCAGTACCGAGAGATCAAAAGCG
GCTCCGTCGACGGAAGCAACGCCAACGCC-
TACTTTGGATACAGCACCCCCTGGGGGTA
CTTTGACTTTAACCGCTTCCACAGCCACTG-
GAGCCCCCGAGACTGGCAAAGACTCATCA ACAAC-
TACTGGGGCTTCAGACCCCGGTCCCTCAGAGT-
CAAAATCTTCAACATTCAAGTC
AAAGAGGTCACGGTGCAGGACTCCACCACCAC-
CATCGCCAACAACCTCACCTCCACCG
TCCAAGTGTTTACGGACGACGAC-
TACCAGCTGCCCTACGTCGTCGGCAACGGGACCGA
GGGATGCCTGCCGGCCTTCCCTCCGCAGGTCTT-
TACGCTGCCGCAGTACGGTTACGCGA     CGCT-
GAACCGCGACAACACAGAAAATCCCACCGAGAG-
GAGCAGCTTCTTCTGCCTAGA
GTACTTTCCCAGCAAGATGCT-
GAGAACGGGCAACAACTTTGAGTTTACCTA-
CAACTTTG                 AGGAGGTGCCCTTC-
CACTCCAGCTTCGCTCCCAGTCAGAACCTCTTCAA-
GCTGGCCAAC
CCGCTGGTGGACCAGTACTTGTACCGCTTCGT-
GAGCACAAATAACACTGGCGGAGTCCA     GTT-
CAACAAGAACCTGGCCGGGAGATACGCCAACACC-
TACAAAAACTGGTTCCCGGGG
CCCATGGGCCGAACCCAGGGCTG-
GAACCTGGGCTCCGGGGT-
CAACCGCGCCAGTGTCA   GCGCCTTCGCCACGAC-
CAATAGGATGGAGCTCGAGGGCGCGAGTTACCAG-
GTGCCCCC                 GCAGCCGAACGGCATGAC-
CAACAACCTCCAGGGCAGCAACACCTATGCCCTG-
GAGAAC                     ACTATGATCTT-
CAACAGCCAGCCGGCGAACCCGGGCACCACCGCC-
ACGTACCTCGAGG                 GCAACATGCTCAT-
CACCAGCGAGAGCGAGACGCAGCCGGT-
GAACCGCGTGGCGTACAA     CGTCGGCGGGCA-
GATGGCCACCAACAACCAGAGCTCCACCACTGCC-
CCCGCGACCGGC                 ACGTACAACCTCCAG-
GAAATCGTGCCCGGCAGCGTGTGGATG-
GAGAGGGACGTGTACC                 TCCAAGGACC-
CATCTGGGCCAAGATCCCAGAGACGGGGGCGCAC-
TTTCACCCCTCTCCG GCCATGGGCGGATTCGGACT-
CAAACACCCACCGCCCATGATGCTCAT-
CAAGAACACGC                 CTGTGCCCGGAAATAT-
CACCAGCTTCTCGGACGTGCCCGTCAGCAGCTTCA-
TCACCCAG     TACAGCACCGGGCAGGTCACCGTG-
GAGATGGAGTGGGAGCTCAAGAAGGAAAACTCC
AAGAGGTGGAACCCAGAGATCCAGTA-
CACAAACAACTACAACGACCCCCAGTTTGTGG ACTTTGCCCCGGACAGCACCGGGGAATACAGAAC-CACCAGACCTATCGGAACCCGATA CCT-TACCCGACCCCTTTAA (SEQ ID NO: 16) or by any other sequence encoding the corresponding amino acid sequence of the VP2 protein of wild-type adeno-associated virus serotype 5 (AAV5) capsid.

"Other sequence encoding the corresponding amino acid sequence of the VP2 protein of wild-type adeno-associated virus serotype 5 (AAV5) capsid" means a nucleic sequence that is alternative to the nucleic sequence with SEQ ID NO: 16, as, due to the degeneracy of genetic code, a wide range of different DNA sequences can encode the amino acid sequence disclosed herein as SEQ ID NO: 8. It is well within the skill of a person trained in the art to create these alternative DNA sequences encoding the same amino acid sequences. Such variant DNA sequences are within the scope of the present invention.

In one aspect, the present invention relates to an isolated nucleic acid encoding the above altered VP3 protein of adeno-associated virus serotype 5 (AAV5) capsid.

In some embodiments, the isolated nucleic acid encoding the altered VP3 protein of adeno-associated virus serotype 5 (AAV5) capsid with the amino acid T519S substitution is represented by the nucleic sequence ATGTCTGCGG-GAGGTGGCGGCCCATTGGGCGACAATAAC-CAAGGTGCCGATGGAGTGG GCAATGCCTCGG-GAGATTGGCATTGCGATTCCACGTGGATGGGGGAC-AGAGTCGTCAC CAAGTC-CACCCGAACCTGGGTGCTGCCCAGCTACAACAAC-CACCAGTACCGAGAGATC AAAAGCGGCTCCGTCGACGGAAGCAACGC-CAACGCCTACTTTGGATACAGCACCCCCT GGGGGTACTTTGACTTTAACCGCTTCCACAGC-CACTGGAGCCCCCGAGACTGGCAAAG ACTCAT-CAACAACTACTGGGGCTTCA-GACCCCGGTCCCTCAGAGTCAAAATCTTCAACA TTCAAGTCAAAGAGGTCACGGTGCAGGACTCCAC-CACCACCATCGCCAACAACCTCAC CTCCACCGTC-CAAGTGTTTACGGACGACGACTACCAGCTGCCC-TACGTCGTCGGCAACG GGACCGAGG-GATGCCTGCCGGCCTTCCCTCCGCAGGTCTT-TACGCTGCCGCAGTACGGT TACGCGACGCT-GAACCGCGACAACACAGAAAATCCCACCGAGAGG-AGCAGCTTCTTCT GCCTAGAGTACTTTCCCAGCAA-GATGCTGAGAACGGGCAACAACTTTGAGTTTACC-TAC AACTTTGAGGAGGTGCCCTTC-CACTCCAGCTTCGCTCCCAGTCAGAACCTCTTCAA-GCT GGC-CAACCCGCTGGTGGACCAGTACTTGTACCGCTTC-GTGAGCACAAATAACACTGGC GGAGTCCAGTT-CAACAAGAACCTGGCCGGGAGATACGCCAACACC-TACAAAAACTGGT TCCCGGGGCC-CATGGGCCGAACCCAGGGCTG-GAACCTGGGCTCCGGGGTCAACCGCGC CAGTGTCAGCGCCTTCGCCACGACCAATAGGATG-GAGCTCGAGGGCGCGAGTTACCAG GTGCCCCCGCAGCCGAACGGCATGAC-CAACAACCTCCAGGGCAGCAACACCTATGCCC TGGAGAACACTATGATCTT-CAACAGCCAGCCGGCGAACCCGGGCACCACCGC-CACGTA CCTCGAGGGCAACATGCTCAT-CACCAGCGAGAGCGAGACGCAGCCGGTGAACCG-CGTG GCGTACAACGTCGGCGGGCAGATGGCCAC-CAACAACCAGAGCTCCACCACTGCCCCCG CGACCGGCACGTACAACCTCCAG-GAAATCGTGCCCGGCAGCGTGTGGATG- GAGAGGGA CGTGTACCTCCAAGGACC-CATCTGGGCCAAGATCCCAGAGACGGGGGCGCAC-TTTCAC CCCTCTCCGGCCATGGGCGGATTCGGACT-CAAACACCCACCGCCCATGATGCTCATCAA GAACACGCCTGTGCCCGGAAATAT-CACCAGCTTCTCGGACGTGCCCGTCAGCAGCTTCA TCACCCAGTACAGCACCGGGCAGGTCACCGTG-GAGATGGAGTGGGAGCTCAAGAAGGA AAACTC-CAAGAGGTGGAACCCAGAGATCCAGTA-CACAAACAACTACAACGACCCCCAG TTTGTGGACTTTGCCCCGGACAGCACCGGG-GAATACAGAAGCACCAGACCTATCGGAA CCCGATACCTTACCCGACCCCTTTAA (SEQ ID NO: 17) or by any other sequence encoding the corresponding amino acid sequence of the altered VP3 protein of adeno-associated virus serotype 5 (AAV5) capsid with the amino acid T519S substitution.

"Other sequence encoding the corresponding amino acid sequence of the altered VP3 protein of adeno-associated virus serotype 5 (AAV5) capsid with the amino acid T519S substitution" means a nucleic sequence that is alternative to the nucleic sequence with SEQ ID NO: 17, as, due to the degeneracy of genetic code, a wide range of different DNA sequences can encode the amino acid sequence disclosed herein as SEQ ID NO: 12. It is well within the skill of a person trained in the art to create these alternative DNA sequences encoding the same amino acid sequences. Such variant DNA sequences are within the scope of the present invention.

In some embodiments, the isolated nucleic acid encoding the altered VP3 protein of adeno-associated virus serotype 5 (AAV5) capsid with the amino acid S459A and T519S substitutions has any nucleic acid sequence that encodes the amino acid sequence disclosed herein as SEQ ID NO: 13. It is well within the skill of a person trained in the art to create these alternative DNA sequences encoding the same amino acid sequences. Such variant DNA sequences are within the scope of the present invention.

The isolated nucleic acid encoding the above VP3 of wild-type adeno-associated virus serotype 5 (AAV5) capsid is represented by the nucleic sequence ATGTCTGCGG-GAGGTGGCGGCCCATTGGGCGACAATAAC-CAAGGTGCCGATGGAGTGG GCAATGCCTCGG-GAGATTGGCATTGCGATTCCACGTGGATGGGGGAC-AGAGTCGTCAC CAAGTC-CACCCGAACCTGGGTGCTGCCCAGCTACAACAAC-CACCAGTACCGAGAGATC AAAAGCGGCTCCGTCGACGGAAGCAACGC-CAACGCCTACTTTGGATACAGCACCCCCT GGGGGTACTTTGACTTTAACCGCTTCCACAGC-CACTGGAGCCCCCGAGACTGGCAAAG ACTCAT-CAACAACTACTGGGGCTTCA-GACCCCGGTCCCTCAGAGTCAAAATCTTCAACA TTCAAGTCAAAGAGGTCACGGTGCAGGACTCCAC-CACCACCATCGCCAACAACCTCAC CTCCACCGTC-CAAGTGTTTACGGACGACGACTACCAGCTGCCC-TACGTCGTCGGCAACG GGACCGAGG-GATGCCTGCCGGCCTTCCCTCCGCAGGTCTT-TACGCTGCCGCAGTACGGT TACGCGACGCT-GAACCGCGACAACACAGAAAATCCCACCGAGAG-GAGCAGCTTCTTCT GCCTAGAGTACTTTCCCAGCAAGATGCT-GAGAACGGGCAACAACTTTGAGTTTACCTAC AACTTTGAGGAGGTGCCCTTC-CACTCCAGCTTCGCTCCCAGTCAGAACCTCTT-CAAGCT GGCCAACCCGCTGGT- GGACCAGTACTTGTACCGCTTCG-
TGAGCACAAATAACACTGGC GGAGTCCAGTT-
CAACAAGAACCTGGCCGGGAGATACGCCAACACC-
TACAAAAACTGGT
TCCCGGGGCCCATGGGCCGAACCCAGGGCTG-
GAACCTGGGCTCC-
GGGGTCAACCGCGC CAGTGTCAGCGCCTTCGC-
CACGACCAATAGGATGGAGCTCGAGGGCGCGAGT-
TACCAG GTGCCCCGCAGCCGAACGGCATGAC-
CAACAACCTCCAGGGCAGCAACACCTATGCCC
TGGAGAACACTATGATCTT-
CAACAGCCAGCCGGCGAACCCGGGCACCACCGC-
CACGTA CCTCGAGGGCAACATGCTCAT-
CACCAGCGAGAGCGAGACGCAGCCGGTGAACCG-
CGTG GCGTACAACGTCGGCGGGCAGATGGCCAC-
CAACAACCAGAGCTCCACCACTGCCCCCG
CGACCGGCACGTACAACCTCCAG-
GAAATCGTGCCCGGCAGCGTGTGGATG-
GAGAGGGA CGTGTACCTCCAAGGACC-
CATCTGGGCCAAGATCCCAGAGACGGGGGCGCAC-
TTTCAC CCCTCTCCGGCCATGGGCGGATTCGGACT-
CAAACACCCACCGCCCATGATGCTCATCAA
GAACACGCCTGTGCCCGGAAATAT-
CACCAGCTTCTCGGACGTGCCCGTCAGCAGCTTCA
TCACCCAGTACAGCACCGGGCAGGTCACCGTG-
GAGATGGAGTGGGAGCTCAAGAAGGA AAACTC-
CAAGAGGTGGAACCCAGAGATCCAGTA-
CACAAACAACTACAACGACCCCCAG
TTTGTGGACTTTGCCCCGGACAGCACCGGG-
GAATACAGAACCACCAGACCTATCGGAA CCCGA-
TACCTTACCCGACCCCTTTAA (SEQ ID NO: 18) or by
any other sequence encoding the corresponding amino acid
sequence of the VP3 protein of wild-type adeno-associated
virus serotype 5 (AAV5) capsid.

"Other sequence encoding the corresponding amino acid
sequence of the VP3 protein of wild-type adeno-associated
virus serotype 5 (AAV5) capsid" means a nucleic sequence
that is alternative to the nucleic sequence with SEQ ID NO:
18, as, due to the degeneracy of genetic code, a wide range
of different DNA sequences can encode the amino acid
sequence disclosed herein as SEQ ID NO: 11. It is well
within the skill of a person trained in the art to create these
alternative DNA sequences encoding the same amino acid
sequences. Such variant DNA sequences are within the
scope of the present invention.

In one aspect, the present invention relates to an isolated
nucleic acid encoding the above capsid, which is used for
highly-efficient transduction of target cells.

In some embodiments, the isolated nucleic acid encoding
the above capsid includes any of the above nucleic acid
sequences.

Vector Based on Recombinant Adeno-Associated Virus
Serotype 5 (rAAV5)

In one aspect, the present invention relates to a vector
based on recombinant adeno-associated virus serotype 5
(rAAV5) for delivery to a subject of a heterologous nucleic
acid sequence, which includes:

1) the above capsid, and 2) a heterologous nucleic acid sequence comprising regu-
      latory sequences that promote the expression of the
      target product encoded by the heterologous nucleic acid
      sequence, in target cells.

The rAAV vector of the invention does not comprise
nucleotide sequences of genes encoding non-structural pro-
teins (Rep) and structural proteins (Cap).

The capsid is characterized in detail in the above section
of the description.

In some embodiments, the vector based on rAAV5 has an
expression product of the heterologous nucleic acid
sequence, which is a therapeutic polypeptide or a reporter
polypeptide.

In some embodiments, the vector based on rAAV5 com-
prises a heterologous nucleic acid sequence encoding a
product that is a therapeutic polypeptide, wherein the thera-
peutic polypeptide is a coagulation factor selected from the
group consisting of Factor VIII, Factor IX, or a functional
variant thereof.

In some embodiments, the vector based on rAAV5 com-
prises a heterologous nucleic acid sequence encoding a
product that is Factor VIII or a functional variant thereof.

In some embodiments, the vector based on rAAV5 com-
prises a heterologous nucleic acid sequence encoding a
product that is Factor IX or a functional variant thereof.

Pharmaceutical Composition

In one aspect, the present invention relates to a pharma-
ceutical composition for the delivery of a gene product to a
subject in need thereof, which comprises:

a) the above vector based on rAAV5; and b) a pharmaceutically acceptable excipient.

In some embodiments, the pharmaceutical composition is
used for the delivery of a gene product to a human in need
thereof.

In particular embodiments, the present invention relates to
a pharmaceutical composition comprising the rAAV5 viral
particle of the invention in a pharmaceutically acceptable
carrier or other medicinal agents, pharmaceutical agents,
carriers, adjuvants, diluents, etc. For injection, the carrier
will typically be a liquid carrier. For other methods of
administration, the carrier may be either solid or liquid, such
as sterile pyrogen-free water or sterile pyrogen-free phos-
phate-buffered saline solution. For inhalation administra-
tion, the carrier is respirable, and preferably is in a solid or
liquid particulate form. As an injection medium, it is pre-
ferred to use water that contains the additives that are
common for injection solutions, such as stabilizing agents,
salts or saline, and/or buffers.

In other embodiments, the present invention relates to a
pharmaceutical composition comprising a cell, in which
vector based on rAAV5 is integrated into the genome, in a
pharmaceutically acceptable carrier or other medicinal
agents, pharmaceutical agents, carriers, adjuvants, diluents,
etc.

"Pharmaceutical composition" means a composition com-
prising the above vector based on rAAV5 of the invention
and at least one of components selected from the group
consisting of pharmaceutically acceptable and pharmaco-
logically compatible excipients, such as fillers, solvents,
diluents, carriers, auxiliary, distributing agents, delivery
agents, preservatives, stabilizers, emulsifiers, suspending
agents, thickeners, prolonged delivery controllers, the
choice and proportions of which depend on the type and
route of administration and dosage. Pharmaceutical compo-
sitions of the present invention and methods for preparation
thereof will be undoubtedly apparent to those skilled in the
art. Pharmaceutical compositions should preferably be
manufactured in compliance with the GMP (Good Manu-
facturing Practice) requirements. A composition may com-
prise a buffer composition, tonicity agents, stabilizers and
solubilizers.

"Pharmaceutically acceptable" means a material that does
not have biological or other negative side effects, for
example, the material can be administered to a subject
without causing any undesirable biological effects. Thus,
such pharmaceutical compositions may be used, for example, in transfection of a cell ex vivo or in administration in vivo of a viral particle or a cell directly to a subject.

The term "excipient" is used herein to describe any ingredient other than the above ingredients of the invention. These are substances of inorganic or organic nature which are used in the pharmaceutical manufacturing in order to give drug products the necessary physicochemical properties.

"Stabilizer" refers to an excipient or a mixture of two or more excipients that provide the physical and/or chemical stability of the active agent.

The term "buffer", "buffer composition", "buffering agent" refers to a solution, which is capable of resisting changes in pH by the action of its acid-base conjugate components, which allows the vector based on rAAV5 product to resist changes in pH. Generally, the pharmaceutical composition preferably has a pH in the range from 4.0 to 8.0. Examples of buffers that can be used include, but are not limited to, acetate, phosphate, citrate, histidine, succinate, etc. buffer solutions.

A pharmaceutical composition is "stable" if the active agent retains physical stability and/or chemical stability and/or biological activity thereof during the specified shelf life at storage temperature, for example, of 2-8° C. Preferably, the active agent retains both physical and chemical stability, as well as biological activity. Storage period is adjusted based on the results of stability test in accelerated or natural aging conditions.

A pharmaceutical composition of the invention can be manufactured, packaged, or widely sold in the form of a single unit dose or a plurality of single unit doses in the form of a ready formulation. The term "single unit dose" as used herein refers to a discrete quantity of a pharmaceutical composition containing a predetermined quantity of an active ingredient. The quantity of the active ingredient typically equals the dose of the active ingredient to be administered in a subject, or a convenient portion of such dose, for example, half or a third of such dose.

Method for Delivery of Gene Product

In one aspect, the present invention relates to a method for the delivery of a gene product to a subject in need thereof, which comprises administering to the subject the above vector based on rAAV5 or the above pharmaceutical composition.

In some embodiments, the method for the delivery of a gene product is used for the delivery of a gene product to a human in need thereof.

Any method for administering vector based on rAAV5, which is recognized in the art, can be suitably used for the above vector based on rAAV5 of the present invention.

The rAAV5-based recombinant viral vectors are preferably administered to a cell in a biologically-effective amount. A "biologically-effective" amount of the viral vector is an amount that is sufficient to cause infection (or transduction) and expression of the heterologous nucleic acid sequence in the cell. If the virus is administered to a cell in vivo (e.g. the virus is administered to a subject, as described below), a "biologically-effective" amount of the viral vector is an amount that is sufficient to cause the transduction and expression of the heterologous nucleic acid sequence in a target cell.

The cell for administering the rAAV5 viral vector of the invention may be a cell of any type, including but not limited to neural cells (including cells of the peripheral and central nervous systems, in particular, brain cells), lung cells, epithelial cells (e.g. gut and respiratory epithelial cells), muscle cells, pancreatic cells (including islet cells), hepatic cells, myocardial cells, bone cells (e.g. bone marrow stem cells), hematopoietic stem cells, spleen cells, keratinocytes, fibroblasts, endothelial cells, prostate cells, germ cells, and the like.

Alternatively, the cell for administering the rAAV5 viral vector may be any progenitor cell. As a further alternative, the cells can be stem cells (e.g. neural stem cells, liver stem cells). Furthermore, the cells can be from any species of origin, as specified above.

Use

In one aspect, the present invention relates to the use of the above vector based on rAAV5 or the above pharmaceutical composition for the treatment of a disease in a subject in need thereof.

In some embodiments, the use is used for the treatment of a disease in a human in need thereof.

Administration of the vector based on rAAV5 of the present invention to a human subject or an animal in need thereof can be by any means known in the art for administering viral vectors.

Exemplary modes of administration include local, oral, rectal, transmucosal, transdermal, inhalation, parenteral administration (e.g. intravenous, subcutaneous, intradermal, intramuscular, and intraarticular administration), and the like, as well as direct tissue or organ injection, and, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for the preparation of solution or suspensions in liquid prior to injection, or as emulsions. Alternatively, one may administer the vector based on rAAV5 in a local rather than systemic manner, for example in a depot or sustained-release formulation.

In some embodiments of the use, the disease is selected from the group comprising: blood diseases; central nervous system diseases; metabolic diseases; muscle diseases; hereditary diseases.

In some embodiments of the use, the disease is a blood disease.

In some embodiments of the use, the disease is a muscle disease.

In some embodiments of the use, the disease is a hereditary disease.

In particular embodiments of the present invention, the nucleotide sequence of interest is delivered by the vector based on rAAV5 to the liver of the subject. Administration to the liver may be performed by any method known in the art, including, but not limited to intravenous administration, intraportal administration, intrabiliary administration, intraarterial administration, and direct injection into the liver parenchyma.

Preferably, the cells (e.g. liver cells) are infected with the vector based on rAAV5 encoding a peptide or protein, the cells express the encoded peptide or protein and secrete it into the blood circulatory system in a therapeutically effective amount (as described below). Alternatively, the vector is delivered to and expressed by another cell or tissue, including but not limited to, brain, pancreas, spleen or muscles.

A "therapeutically-effective amount" is understood to mean an amount that is sufficient to alleviate (e.g. mitigate, decrease, reduce) at least one of the symptoms associated with a disease state. Alternatively stated, a "therapeutically-effective" amount is an amount that is sufficient to provide some improvement in the condition of the subject.

In some embodiments of the use, the expression product of the heterologous nucleic acid sequence is Factor IX or a functional variant thereof.

In some embodiments of the use, the expression product of the heterologous nucleic acid sequence is Factor VIII or a functional variant thereof.

In other preferred embodiments, the vector based on rAAV5 of the invention is administered intramuscularly, more preferably by intramuscular injection or by local administration (as described above). In other preferred embodiments, the parvovirus particles of the present invention are administered to the lungs.

The vector based on rAAV5 disclosed in the invention may be administered to the lungs of a subject by any suitable means, but is preferably administered in the form of an aerosol suspension of respirable particles comprised of the vector based on rAAV5 of the invention, which the subject inhales. The respirable particles may be liquid or solid. Aerosols of liquid particles comprising the parvovirus rAAV5 vectors of the invention may be produced by any suitable means, such as with a pressure-driven aerosol nebulizer or an ultrasonic nebulizer, as is known to those skilled in the art. Aerosols of solid particles comprising the viral rAAV5 vectors of the invention may also be produced with any solid particulate medicament aerosol generator by techniques known in the pharmaceutical art.

Dosages of the parvovirus rAAV5 particles of the invention will depend on the mode of administration, the disease or condition to be treated, the subject's condition, the particular viral vector, and the gene to be delivered and can be determined in a routine manner. Exemplary doses for achieving therapeutic effects are viral titers of at least about $10^5$, $10^6$, $10'$, $10^8$, $10^9$, $10^{10}$, $10^{11}$, $10^{12}$, $10^{13}$, $10^{14}$, $10^{15}$, $10^{16}$ transducting units or more, preferably about $10^8$ to $10^{13}$ transducting units, yet more preferably $10^{12}$ transducing units.

Thus, the parvovirus vectors based on rAAV5, reagents, and methods of the present invention can be used to direct a nucleic acid to either dividing or non-dividing cells, and to stably express the heterologous nucleic acid therein. Using this vector system, it is now possible to introduce into cells under in vivo conditions the genes that encode proteins that affect cell physiology. The vectors of the present invention can thus be useful in gene therapy for disease states.

In general, the present invention may be employed to deliver any foreign nucleic acid with a biological effect to treat or ameliorate the symptoms associated with any disorder related to gene expression. Examplary disease states include, but are not limited to: cystic fibrosis (and other lung diseases), hemophilia A, hemophilia B, thalassemia, anemia and other blood coagulation disorders, AIDs, Alzheimer's disease, Parkinson's disease, Huntington's disease, amyotrophic lateral sclerosis, epilepsy, and other neurological disorders, diabetes mellitus, muscular dystrophies (e.g. Duchenne, Becker), Gaucher's disease, Hurler's disease, adenosine deaminase deficiency, glycogen storage diseases and other metabolic defects, diseases of solid organs (e.g. brain, liver, kidney, heart), and the like.

Gene transfer has substantial potential use in understanding and providing therapy for disease states. There are a number of hereditary diseases for which defective genes are known and have been cloned. In some cases, the function of these cloned genes is known. In general, the above disease states fall into two classes: deficiency states, typically enzyme deficiency, which are generally inherited in a recessive manner, and unbalanced states, sometimes involving at least regulatory or structural proteins, which are inherited in a dominant manner. For deficiency state diseases, gene transfer could be used to bring a normal gene into affected tissues for replacement therapy. For unbalanced disease states, gene transfer could be used to create a disease state in a model system, which could then be used in efforts to counteract the disease state. Thus, the methods of the present invention permit to treat genetic diseases. According to the invention, a disease state is treated by partially or wholly remedying the deficiency or imbalance that causes the disease or makes it more severe. The use of site-specific integration of nucleic sequences to induce mutations or to correct deficiencies is also possible.

Method for Producing rAAV5-Based Vector

In one aspect, the present invention relates to a method for the production of the above vector based on rAAV5, which comprises the transfection of producer cells with the above nucleic acid comprising a sequence encoding a capsid including an altered VP1 capsid protein of adeno-associated virus serotype 5 (AAV5).

In some embodiments of the method for producing the vector based on rAAV5, used is the above nucleic acid which comprises a sequence encoding the above altered VP1 protein of adeno-associated virus serotype 5 (AAV5) capsid, a VP2 protein of AAV5 capsid or an altered variant thereof, and a VP3 protein of AAV5 capsid or an altered variant thereof.

Altered variants of the VP2 protein of the wild-type AAV5 capsid and the VP3 protein of AAV5 capsid protein are understood to mean the variants of the VP2 protein of the wild-type AAV5 capsid and VP3 protein of the wild-type AAV5 capsid, which include one or more amino acid substitutions.

Particularly preferred embodiments include substitutions that are conservative in nature, i.e. substitutions which that take place within a family of amino acids that are joined in their side chains. In particular, amino acids are typically divided into four families: (1) acidic amino acids are aspartate and glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. Phenylalanine, tryptophan, and tyrosine are sometimes classified as aromatic amino acids. For example, it is reasonably predictable that an isolated substitution of leucine for isoleucine or valine, an aspartate for a glutamate, a threonine for a serine, or a similar conservative substitution of an amino acid for a structurally related amino acid, will not have a major effect on the biological activity. For example, the polypeptide of interest may include up to about 5-10 conservative or non-conservative amino acid substitutions, or even up to about 15-25 or 50 conservative or non-conservative amino acid substitutions, or any integer between 5-50, so long as the desired function of the molecule remains intact.

In some embodiments of the method for producing the vector based on rAAV5, used is the above nucleic acid which comprises a sequence encoding the above altered VP1 protein of adeno-associated virus serotype 5 (AAV5) capsid, the VP2 protein of the wild-type AAV5 capsid and VP3 protein of the wild-type AAV5 capsid The altered variants of the VP2 and VP3 proteins of AAV5 capsids, as well as nucleic acids encoding them, are disclosed in detail in the corresponding sections of the description.

EXAMPLES

The following examples are provided for better understanding of the invention. These examples are for purposes of illustration only and are not to be construed as limiting the scope of the invention in any manner.

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended embodiments.

Materials and General Methods

Recombinant DNA Techniques

DNA manipulations were carried out by standard techniques as described by Sambrook J. et al, Molecular cloning: A laboratory manual; Cold Spring Harbor Laboratory Press, Cold Spring Harbor, N.Y., 1989. The molecular biological reagents were used according to the manufacturer instructions.

Gene Synthesis

Desired gene segments were prepared from oligonucleotides made by chemical synthesis. The gene segments of 300-4000 bp long, which were flanked by singular restriction sites, were assembled by annealing and ligation of oligonucleotides including PCR amplification and subsequently cloned via the specified restriction sites. The DNA sequences of the subcloned gene fragments were confirmed by DNA sequencing.

DNA Sequence Determination

DNA sequences were determined by Sanger sequencing.

DNA and protein sequence analysis and sequence data management

The Infomax's Vector NTI Advance suite version 8.0 and SnapGene Viewer were used for sequence creation, mapping, analysis, annotation and illustration.

Example 1. Production of Libraries of AAV5 Capsid Variants

Figure 1:
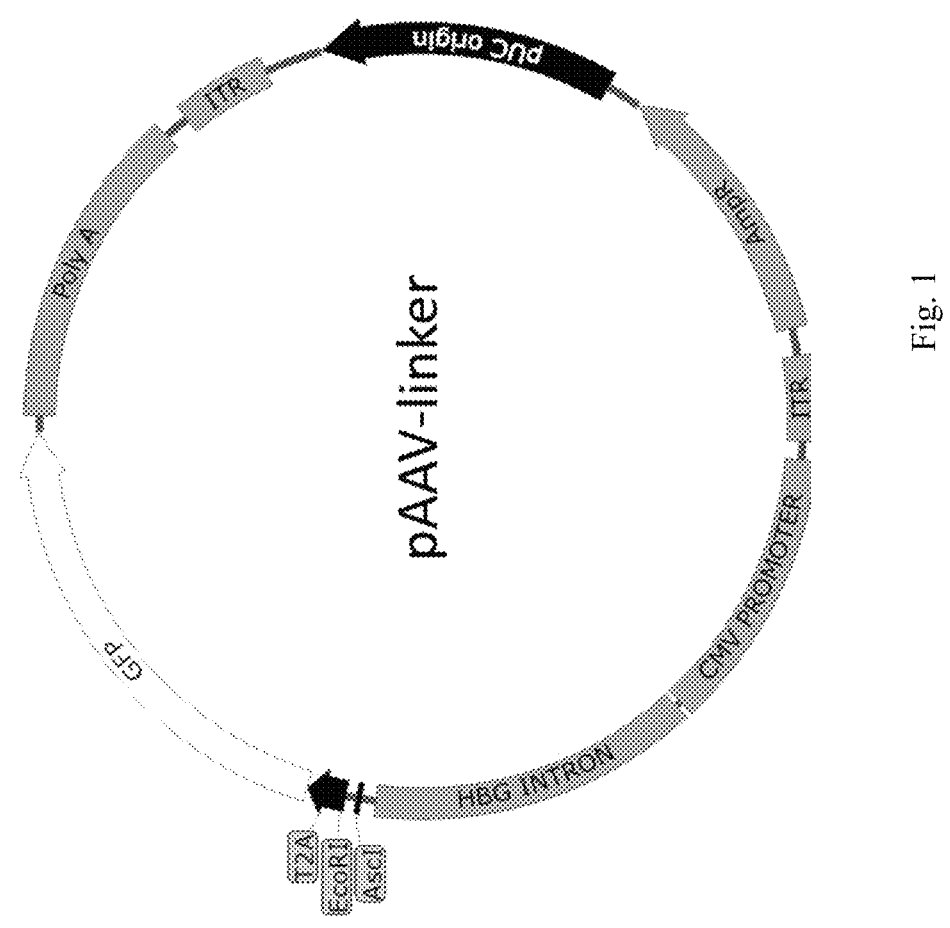
FIG. 1. Circular scheme of plasmid pAAV-linker intended for cloning the libraries of random variants of capsid gene of AAV serotype 5.

Libraries of AAV5 capsid variants were produced by random mutagenesis of the Cap gene sequence (Davidsson M. et al., 2016). Briefly, the wild-type sequence of the Cap gene of serotype 5 (GenBank ID AF085716.1) was assembled de novo, the synthesized wild-type AAV5 capsid gene was thereafter fragmented using uracil-DNA glycosylase, the resulting fragments were assembled to a full-length Cap gene using DNA polymerase not having a proofreading activity (as a result, random mutations emerged in the sequence). The full-length mutant variants were cloned into the carrier plasmid pAAV-linker (FIG. 1) at AscllEcoRl restriction sites in a common reading frame with green fluorescent protein (GFP), thereby producing a diverse random library of AAV5 capsids, which library was thereafter used to select capsid variants having increased transduction activity.

Positive selection of viral particles having increased transduction activity was performed in vitro on CHO-K1-S cells. Thereby, for transduction, we used particles that were purified using ultracentrifugation in a iodixanol gradient. After 48 hours, the cells were harvested and genomic DNA was isolated for subsequent amplification of the viral genome sequences capable of efficient transduction. The resulting sequences were thereafter re-cloned and re-produced for subsequent selection iterations to enrich the library with variants having the highest transduction efficiency. After 5 rounds of selection, the capsid genes of 30 clones were sequenced to determine the most successful mutations and combinations thereof. The sequencing results showed that the predominant combinations of mutations were S2A, T711S in AAV5 VP1 and capsid variants containing S2A, T711S, S651A in AAV5 VP1, which were about 20% of the clones. Capsid variants comprising the mutation S651A in AAV5 VP1 were also selected. These capsid variants were cloned into vectors for producing viral particles and further used for visualizing and comparing the transduction profiles relative to wild-type AAV5.

Example 2. Production and Subsequent Selection of Recombinant Viral Particles from Resulting Sequence Library To produce and subsequently select recombinant viral particles from the resulting sequence library, a series of plasmids was developed as follows: a carrier plasmid, a plasmid comprising the Rep gene sequence, as well as a construct comprising adenoviral genes that are required for the replication of viral particles.

The carrier plasmid pAAV-linker (FIG. 1), intended for cloning the libraries of random variants of the capsid gene of AAV serotype 5 into one reading frame with the reporter protein, was produced by substituting the sequence of a modified green fluorescent protein in the original construct pAAV-GFP Control plasmid (VPK-402) from CellBiolab (USA), using the restrictase-ligase method of cloning at HindIII/EcoRI sites, for the sequence T2A-GFP synthesized de novo with the addition of an EcoRI restriction site from the 5' end and a HindIII restriction site from the 3' end.

The plasmid pAAV-Rep comprising the Rep gene sequence (FIG. 2) was produced by de novo cloning of the synthesized sequence of the AAV serotype 2 Rep gene (GenBank ID AF043303.1) at Pcil/Psil restriction sites (New England Biolabs, USA) with subsequent treatment with T4 DNA Polymerase (New England Biolabs, USA) to generate blunt ends into the plasmid pGem-T Easy (Promega, USA) also treated with Pcil/Psil restriction enzymes (New England Biolabs, USA).

The adenoviral genes for producing the recombinant viral particles were sourced from the construct pHelper (FIG. 3) from the commercial kit AAV-2 Packaging System (VPK-402) from CellBiolab (USA), comprising AmpR—a beta-lactamase gene that provides resistance to ampicillin, Ori—a replication origin in bacteria, Adeno E2A—a helper adenovirus gene sequence involved in viral DNA replication, Adeno E4-a helper adenovirus gene sequence involved in viral DNA replication, Adeno VARNA—a helper adenovirus gene sequence responsible for the translation of both early and late viral genes Example 3. Method for Producing Vectors Based on Altered Adeno-Associated Virus Serotype 5 (rAAV)

To produce rAAV particles with an altered serotype 5 capsid, producer cells were transfected simultaneously with 3 plasmids as follows:
1) With a plasmid comprising adenovirus nucleotide sequences encoding proteins and RNAs required for assembly of rAAV particles (helper plasmid);
2) With a plasmid comprising the natural nucleotide sequence of the Rep gene of adeno-associated virus serotype 2, as well as the sequence of an altered Cap gene, which is selected from the group comprising: the nucleotide sequence of SEQ ID NOs: 5, 6 or 7 or any other nucleotide sequence encoding the VP1 protein with the amino acid sequences of SEQ ID Nos: 2, 3 or 4, and the VP2 and VP3 proteins from alternative reading frames of the nucleotide sequence being used, wherein the VP2 can have any of the amino acid sequences of SEQ ID Nos: 8, 9, or 10;

and the VP3 can have any of the amino acid sequences of SEQ ID Nos: 11, 12, or 13;

3) With a plasmid comprising the heterologous genome of the rAAV particle, encoding a target gene intended for delivery into patient's cells.

This set of genes provides assembly of the rAAV viral particles and encapsidation therein of the target genome within 72 hours. 72 hours following transfection, the producer cells are lysed to release rAAV particles for purification by subsequent filtration and chromatography steps. The titer of the purified rAAV particles is verified by enzyme linked immunosorbent assay and quantitative PCR.

Example 4. Increasing the Efficiency of Cell Transduction with rAAV5-Based Products in the Presence of Mutations S2A, S651A, T711S in VP1 Protein of the Wild-Type AAV5 Capsid Experimental Design:

CHO-K1-S cells were plated into the wells of 12-well plates. Seeding was made into the following growth medium: DMEM/F12 supplemented with glutamine, glucose content was 4.5 g/l, 5% bovine serum. Cell seeding density was 10,000 cell/cm2. During the transduction run, pre-prepared cells were transduced at MOI of 100,000 vg/cell. All samples were run in triplicates. Intact cells were used as a negative control.

Analysis of transduction efficiency was performed using the Guava EasyCyteflow cytometer and the GuavaSoft software.

The inventors have surprisingly found that the presence of one or more mutations selected from the group comprising S2A, S651A or T711S in VP1 protein of the wild-type AAV5 capsid caused a significant increase in the efficiency of transgene delivery by the rAAV vectors with the above mutations. For example, the flow cytometry method showed a change in the amount of GFP-positive cells 48 hours post transduction of the CHO-K1-S line with the rAAV-based products containing the VP1 protein of the wild-type AAV5 capsid or the VP1 protein of the wild-type AAV5 capsid bearing one or more mutations selected from the group comprising: S2A, S651A, T711S (FIG. 4.).

When the mutation S651A (AAV5-01Mut-GFP) was present, the amount of GFP-expressing cells increased 2.2-fold from 22.54% to 49.45% as compared to control AAV5 with a wild-type VP1 capsid protein (AAV5-NullMut-GFP).

When both the mutations S2A and T711S (AAV5-02Mut-GFP) were simultaneously present, the amount of GFP-expressing cells increased 2.6-fold from 22.54% to 58.51% as compared to control AAV5 with a wild-type VP1 capsid protein (AAV5-NullMut-GFP).

When the mutations S2A, S651A and T711S (AAV5-03Mut-GFP) were simultaneously present, the amount of GFP-expressing cells increased 1.7-fold from 22.54% to 38.27% as compared to control AAV5 with a wild-type VP1 capsid protein (AAV5-NullMut-GFP).

Example 5. Increasing the Production of Target Protein Encoded by Transgene Following Cell Transduction with rAAV5-Based Products in the Presence of Mutations S2A, S651A, T711S in the VP1 Protein of the Wild-Type AAV5 Capsid Experimental Design:

CHO-K1-S cells were plated into the wells of 12-well plates. Seeding was made into the following growth medium: DMEM/F12 supplemented with glutamine, glucose content was 4.5 g/l, 5% bovine serum. Cell seeding density was 10,000 cell/cm2. During the transduction run, pre-prepared cells were transduced at MOI of 100,000 vg/cell. All samples were run in triplicates. Intact cells were used as a negative control.

The amount of FIX protein in the culture liquid 7 days post transduction was assessed using the Human Factor IX ELISA Kit. We used a 1:25 dilution of the samples. The procedure was carried out according to the manufacturer's instructions.

The inventors have surprisingly found that the presence of one or more mutations selected from the group comprising S2A, S651A, T711S in the VP1 protein of the wild-type AAV5 capsid caused a significant increase in the production of hFIX protein post transduction of the CHO-K1-S cells with the vectors based on rAAV with the above mutations. For example, the enzyme-linked immunosorbent assay (ELISA) method showed an increase in the amount of hFIX protein in the culture medium 7 days post transduction of the CHO-K1-S cells with the rAAV products with a wild-type AAV5 VP1 capsid protein or the VP1 protein of the wild-type AAV5 capsid bearing one or more mutations selected from the group comprising: S2A, S651A, T711S (FIG. 5.).

When the mutation S651A (AAV5-01Mut-FIX) was present, the amount of protein being produced increased 4.6-fold from 0.17 ng/ml to 0.74 ng/ml as compared to control AAV5 with a wild-type VP1 capsid protein (AAV5-NullMut-GFP).

When both the mutations S2A and T711S (AAV5-02Mut-GFP) were simultaneously present, the amount of protein being produced increased 7.1-fold from 0.17 ng/ml to 1.24 ng/ml as compared to control AAV5 with a wild-type VP1 capsid protein (AAV5-NullMut-GFP).

When the mutations S2A, S651A and T711S (AAV5-03Mut-GFP) were simultaneously present, the amount of protein being produced increased 3.3-fold from 0.17 ng/ml to 0.57 ng/ml as compared to control AAV5 with a wild-type VP1 capsid protein (AAV5-NullMut-GFP).

The invention claimed is:

1. An isolated altered VP1 protein of adeno-associated virus serotype 5 (AAV5) capsid for transduction of target cells, comprising the amino acid sequence of the VP1 protein of a wild-type AAV5 capsid, encoded by the Cap gene, comprising one or more substitutions selected from the group comprising:

a S2A and T711S substitution, or a S2A, S651A and T711S substitution, wherein the amino acid sequence of the VP1 protein of a wild-type AAV5 capsid has the amino acid sequence of SEQ ID NO: 1.

2. The isolated altered VP1 protein of the AAV5 capsid of claim 1, which comprises the S2A and T711S substitutions.

3. The isolated altered VP1 protein of the AAV5 capsid of claim 2, which has the amino acid sequence of SEQ ID NO: 3.

4. The isolated altered VP1 protein of the AAV5 capsid of claim 1, which comprises the substitutions S2A, S651A and T711S.

5. The isolated altered AAV5 VP1 capsid protein of claim 4, which has the amino acid sequence of SEQ ID NO: 4.

6. An isolated nucleic acid encoding the altered VP1 protein of adeno-associated virus serotype 5 (AAV5) capsid of claim 1, which is used for transduction of target cells.

7. The isolated nucleic acid of claim 6 encoding an altered VP1 protein of adeno-associated virus serotype 5 (AAV5) capsid comprising:

(i) the nucleic sequence of SEQ ID NO: 6; or (ii) the nucleic sequence of SEQ ID NO: 7.

8. An isolated capsid for transduction of target cells comprising the altered VP1 protein of adeno-associated virus serotype 5 (AAV5) capsid of claim 1.

9. The isolated capsid of claim 8 comprising the altered VP1 protein of adeno-associated virus serotype 5 (AAV5) capsid, a VP2 protein of AAV5 capsid or an altered variant thereof, and a VP3 protein of AAV5 capsid or an altered variant thereof.

10. The isolated capsid of claim 9 comprising:

(i) the VP2 protein of a wild-type AAV5 capsid; or (ii) the altered VP2 protein of adeno-associated virus serotype 5 (AAV5) capsid.

11. The isolated capsid of claim 10, comprising the VP2 protein of a wild-type AAV5 capsid protein having the amino acid sequence of SEQ ID NO: 8.

12. The isolated capsid of claim 10, comprising the altered VP2 protein of AAV5 capsid, comprising the amino acid sequence of the VP2 protein of a wild-type AAV5 capsid, encoded by the Cap gene, comprising one or more substitutions selected from the group comprising:

a T575S substitution, or a S515A, and a T575S substitution, wherein the amino acid sequence of the VP2 protein of a wild-type AAV5 capsid has the amino acid sequence of SEQ ID NO: 8.

13. The isolated capsid of claim 12, comprising the altered VP2 protein of AAV5 capsid comprising the T575S substitution and having the amino acid sequence of SEQ ID NO: 9 or the S515A and T575S substitutions and having the amino acid sequence of SEQ ID NO: 10.

14. The isolated capsid of claim 9 comprising:

(i) the VP3 protein of a wild-type AAV5 capsid; or (ii) the altered VP3 protein of adeno-associated virus serotype 5 (AAV5) capsid.

15. The isolated capsid of claim 14, comprising the VP3 protein of a wild-type AAV5 capsid having the amino acid sequence of SEQ ID NO: 11.

16. The isolated capsid of claim 14, comprising the altered VP3 protein of AAV5 capsid, comprising the amino acid sequence of the VP3 protein of a wild-type AAV5 capsid, encoded by the Cap gene, comprising one or more substitutions selected from the group comprising:

a T519S substitution, or a S459A, and a T519S substitution, wherein the amino acid sequence of the VP3 protein of a wild-type AAV5 capsid has the amino acid sequence of SEQ ID NO: 11.

17. The isolated capsid of claim 16 comprising the altered VP3 protein of AAV5 capsid comprising the T519S substitution and having the amino acid sequence of SEQ ID NO: 12; or comprising the S459A and T519S substitutions and having the amino acid sequence of SEQ ID NO: 13.

18. An isolated nucleic acid encoding the capsid of claim 8, for transduction of target cells.

19. A vector based on recombinant adeno-associated virus serotype 5 (rAAV5) for delivery to a subject of a heterologous nucleic acid sequence, which comprises:

1) the capsid of claim 8, and 2) a heterologous nucleic acid sequence comprising regulatory sequences that promote the expression of a product encoded by the heterologous nucleic acid sequence, in target cells.

20. The vector based on rAAV5 of claim 19, wherein the expression product of the heterologous nucleic acid sequence is a therapeutic polypeptide or a reporter polypeptide.

21. The vector based on rAAV5 of claim 20, wherein the therapeutic polypeptide is a coagulation factor selected from the group consisting of Factor VIII, Factor IX, or a functional variant thereof.

22. The vector based on rAAV5 of claim 21, wherein the therapeutic peptide is Factor VIII or a functional variant thereof; or wherein the therapeutic peptide is Factor IX or a functional variant thereof.

23. A pharmaceutical composition for the delivery of a gene product to a subject in need thereof, comprising:

a) the vector based on rAAV5 of claim 19; and b) a pharmaceutically acceptable excipient.

24. The pharmaceutical composition of claim 23, wherein the subject is a human subject.

25. A method for the delivery of a gene product to a subject in need thereof, comprising administering to the subject the vector based on rAAV5 of claim 19 or a pharmaceutical composition for the delivery of a gene product to a subject in need thereof, comprising the vector based on rAAV5 and a pharmaceutically acceptable excipient.

26. The method for the delivery of a gene product of claim 25, wherein the subject is a human subject.

27. A method of obtaining of the vector based on rAAV5 of claim 19 comprising the transfection of producer cells with a nucleic acid encoding the capsid, which is used for transduction of target cells.

* * * * *